United States Patent
Carson et al.

(10) Patent No.: US 9,688,710 B2
(45) Date of Patent: Jun. 27, 2017

(54) INHIBITORS OF SODIUM GLUCOSE COTRANSPORTER 1

(71) Applicant: LEXICON PHARMACEUTICALS, INC., The Woodlands, TX (US)

(72) Inventors: Kenneth Gordon Carson, Princeton, NJ (US); Nicole Cathleen Goodwin, Pennington, NJ (US); Bryce Alden Harrison, Hamilton, NJ (US); David Brent Rawlins, Morrisville, PA (US); Eric Strobel, Warrington, PA (US); Brian Zambrowicz, The Woodlands, TX (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 14/943,505

(22) Filed: Nov. 17, 2015

(65) Prior Publication Data
US 2016/0326205 A1 Nov. 10, 2016

Related U.S. Application Data

(63) Continuation of application No. 14/082,786, filed on Nov. 18, 2013, now Pat. No. 9,200,025.

(60) Provisional application No. 61/728,373, filed on Nov. 20, 2012.

(51) Int. Cl.
*C07H 15/14* (2006.01)
*C07D 309/10* (2006.01)
*C07H 5/00* (2006.01)

(52) U.S. Cl.
CPC ........... *C07H 15/14* (2013.01); *C07D 309/10* (2013.01); *C07H 5/00* (2013.01)

(58) Field of Classification Search
None
See application file for complete search history.

(56) References Cited

U.S. PATENT DOCUMENTS

| 7,781,577 B2 * | 8/2010 | Harrison | C07D 211/46 536/29.1 |
|---|---|---|---|
| 7,846,945 B2 | 12/2010 | Harrison | |
| 8,217,156 B2 | 7/2012 | De Paul | |
| 9,200,025 B2 | 12/2015 | Carson | |
| 2005/0272669 A1 | 12/2005 | Fushimi | |
| 2008/0113922 A1 * | 5/2008 | Harrison | C07D 211/46 514/23 |
| 2009/0118201 A1 | 5/2009 | Chen | |
| 2010/0022460 A1 | 1/2010 | Kakinuma | |
| 2011/0218159 A1 | 9/2011 | Brown | |

FOREIGN PATENT DOCUMENTS

| WO | WO2011/023755 | 3/2011 |
|---|---|---|
| WO | WO2011/070592 | 6/2011 |

OTHER PUBLICATIONS

Calvo, Moises Blanco et al., Int. J. Endocrinol. (2011) article ID 205357.
Handlon, A.L., *Expert Opin. Therapeutic Patents* 15(11):1531-1540 (2005).
Search Report and Written Opinion for Corresponding International Application PCT/US2013/070556, mailed Feb. 19, 2014.

* cited by examiner

*Primary Examiner* — Layla Berry
(74) *Attorney, Agent, or Firm* — Max Bachrach

(57) ABSTRACT

Inhibitors of sodium glucose cotransporter 1 (SGLT1), compositions comprising them, and methods of their use to treat diseases and disorders such as diabetes are disclosed. Particular compounds are of the formula:

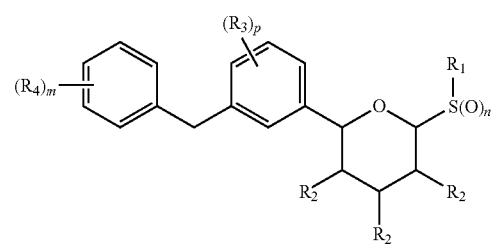

the various substituents of which are defined herein.

8 Claims, 6 Drawing Sheets

INHIBITORS OF SODIUM GLUCOSE COTRANSPORTER 1

This application claims priority to U.S. patent application Ser. No. 14/082,786, filed Nov. 18, 2013, which claims priority to provisional patent application No. 61/728,373, filed Nov. 20, 2012, the entireties of which are incorporated herein by reference.

1. FIELD OF THE INVENTION

This invention relates to compounds that can be used to inhibit sodium glucose cotransporter 1 (SLGT1), compositions comprising them, and methods of their use.

2. BACKGROUND

Type 2 diabetes mellitus is a chronic disease characterized by hyperglycemia caused by hepatic glucose production, a deficiency in insulin secretion, and/or peripheral insulin resistance. In recent years, considerable effort has been directed towards discovering ways of treating the disease. One relatively new approach is inhibition of the sodium glucose cotransporter (SLGT), which lowers blood glucose levels by removing glucose from the bloodstream.

Under normal conditions, plasma glucose is filtered in the kidney glomerulus and in healthy individuals is almost completely reabsorbed. Obermeier, M., et al., *Drug Metabolism Disposition* 38(3):405-414, 406 (2010). That reabsorption is mediated by two sodium-dependent glucose cotransporters: SGLT1 and SGLT2. SGLT1 is expressed in the gut, heart, and kidney, while SGLT2 is expressed primarily in the proximal tubule of the nephron. Id. Although compounds that inhibit both transporters have been described, research has largely focused on discovering selective SGLT2 inhibitors. This is due, in part, to the discovery that a defective SGLT1 transporter in the gut is responsible for some glucose and galactose malabsorption disorders, and the belief that inhibition of SGLT1 would therefore be attended by unacceptable adverse effects. Id. Thus, most SGLT inhibitors currently in clinical trials, including dapagliflozin, canagliflozin, and empagliflozin, are selective SGLT2 inhibitors.

Recent clinical trial results do suggest, however, that inhibition of SGLT1 can provide benefits that extend beyond those provided merely by the inhibition of glucose reabsorption. See, e.g., U.S. patent application publication no. US-2011-0218159. In particular, it is believed that inhibition of SGLT1 can increase glucagon-like peptide-1 (GLP-1) levels. See, e.g., Moriya, R., et al., *Am J Physiol Endocrinol Metab* 297: E1358-E1365 (2009). A number of well-known diabetes drugs, including sitagliptin, vildagliptin and saxagliptin, work by inhibiting dipeptidyl peptidase IV (DPP-4), which is the enzyme responsible for GLP-1 degradation.

3. SUMMARY OF THE INVENTION

This invention is based on the discovery of novel and potent inhibitors of sodium glucose cotransporter 1 (SGLT1). Particular inhibitors are selective inhibitors of SGLT1. Particular inhibitors have low systemic exposure.

This invention is directed, in part, to compositions comprising and methods of using compounds of the formula:

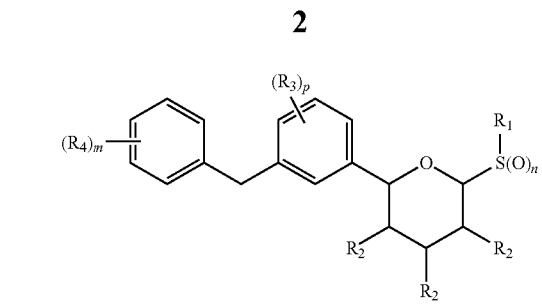

and pharmaceutically acceptable salts, dimers or trimers thereof, wherein: $R_1$ is hydrogen or optionally substituted $C_{1-10}$-alkyl, $C_{1-5}$-cycloalkyl, or 5-membered heterocycle, which optional substitution is with one or more $R_{1A}$; each $R_{1A}$ is independently amino, ester, amide, thiol, carboxylic acid, cyano, halo, hydroxyl, or optionally substituted $C_{1-4}$-alkoxy, $C_{1-5}$-cycloalkyl, or 5-membered heterocycle, which optional substitution is with one or more $R_{1B}$; each $R_{1B}$ is independently $C_{1-4}$-alkyl, halo, or hydroxyl; n is 0, 1, or 2; each $R_2$ is independently F or $OR_{2A}$, wherein each $R_{2A}$ is independently hydrogen, $C_{1-4}$-alkyl, or acyl; each $R_3$ is independently halo, hydroxyl, or optionally substituted $C_{1-10}$-alkyl or $C_{1-10}$-alkoxy, which optional substitution is with one or more $R_{3A}$; each $R_{3A}$ is independently amino, ester, amide, thiol, carboxylic acid, cyano, halo, hydroxyl, or optionally substituted $C_{1-4}$-alkoxy, $C_{1-5}$-cycloalkyl, or 5-membered heterocycle, which optional substitution is with one or more $R_{3B}$; each $R_{3B}$ is independently $C_{1-4}$-alkyl, amino, cyano, halo, or hydroxyl; p is 0, 1, or 2; each $R_4$ is independently $R_{4A}$, $-N(R_{4A})(R_{4B})$, $-OR_{4A}$, $-SR_{4A}$, $-S(O)R_{4A}$, or $-S(O)_2R_{4A}$; $R_{4A}$ is optionally substituted $C_{4-20}$-alkyl or 4-20-membered heteroalkyl, which optional substitution is with one or more $R_{4C}$, and which is optionally attached to another $R_{4A}$ moiety to provide a dimer or trimer; $R_{4B}$ is hydrogen or $R_{4A}$; each $R_{4C}$ is independently amino, amido, azo, carbonyl, carboxyl, cyano, formyl, guanidino, halo, hydroxyl, imido, imino, isothiocyanate, nitrile, nitro, nitroso, nitroxy, oxo, sulfanyl, sulfinyl, sulfonyl, thial, thiocyanate, thione, thiourea, urea, or $X_1$, $X_1$-$L_1$-$X_2$, or $X_1$-$L_1$-$X_2$-$L_2$-$X_3$, wherein each of $X_1$, $X_2$ and $X_3$ is independently optionally substituted $C_{1-4}$-alkyl, $C_{1-6}$-cycloalkyl, 5- or 6-membered heterocycle, or aryl, which optional substitution is with one or more $R_{4D}$, and each of $L_1$ and $L_2$ is independently optionally substituted $C_{1-6}$-alkyl or 1-10-membered heteroalkyl, which optional substitution is with one or more of $R_{4E}$; each $R_{4D}$ is independently $R_{4E}$ or $C_{1-6}$-alkyl optionally substituted with one or more of $R_{4E}$; each $R_{4E}$ is independently amino, amido, azo, carbonyl, carboxyl, cyano, formyl, guanidino, halo, hydroxyl, imido, imino, isothiocyanate, nitrile, nitro, nitroso, nitroxy, oxo, sulfanyl, sulfinyl, sulfonyl, thial, thiocyanate, thione, or urea; and m is 1, 2 or 3.

Particular compounds are of the formula:

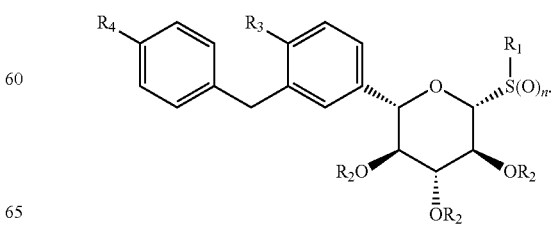

Some are of the formula:

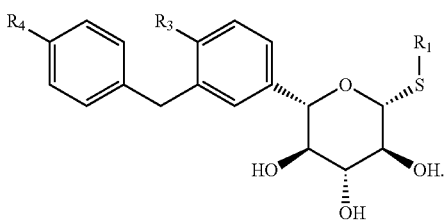

This invention is further directed to pharmaceutical compositions comprising the compounds disclosed herein and methods of their use to treat and/or manage cardiovascular diseases and disorders, metabolic diseases and disorders, bowel diseases and disorders, and certain types of cancer.

4. BRIEF DESCRIPTION OF THE FIGURES

Certain aspects of this invention may be understood with reference to the figures.

Figures 5A, 5B:
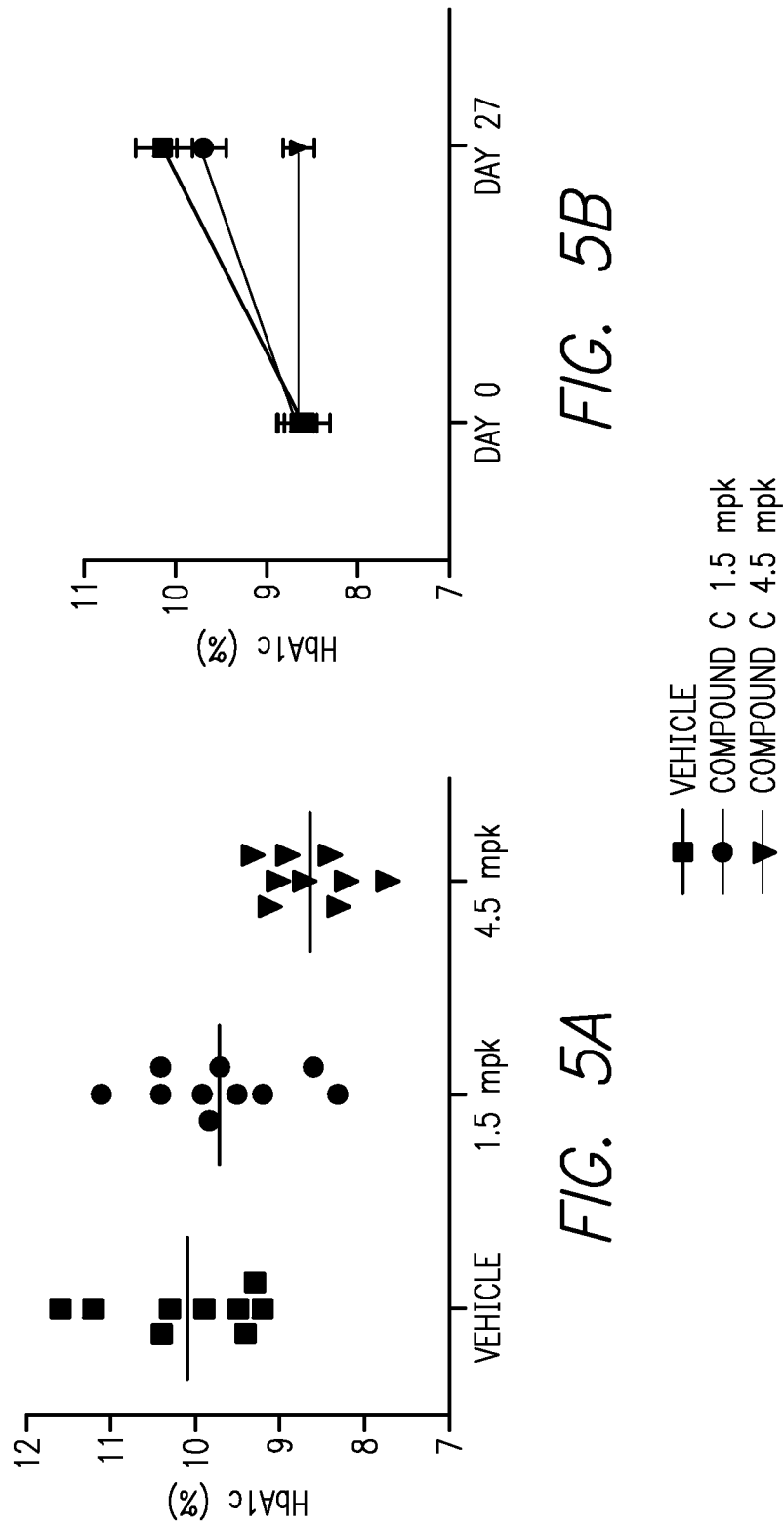

FIG. 5A shows the compound's effect on the mice's HbA1c levels after 26 days of dosing. FIG. 5B shows the change in the mice's HbA1c levels between days 0 and 27.

Figure 6:
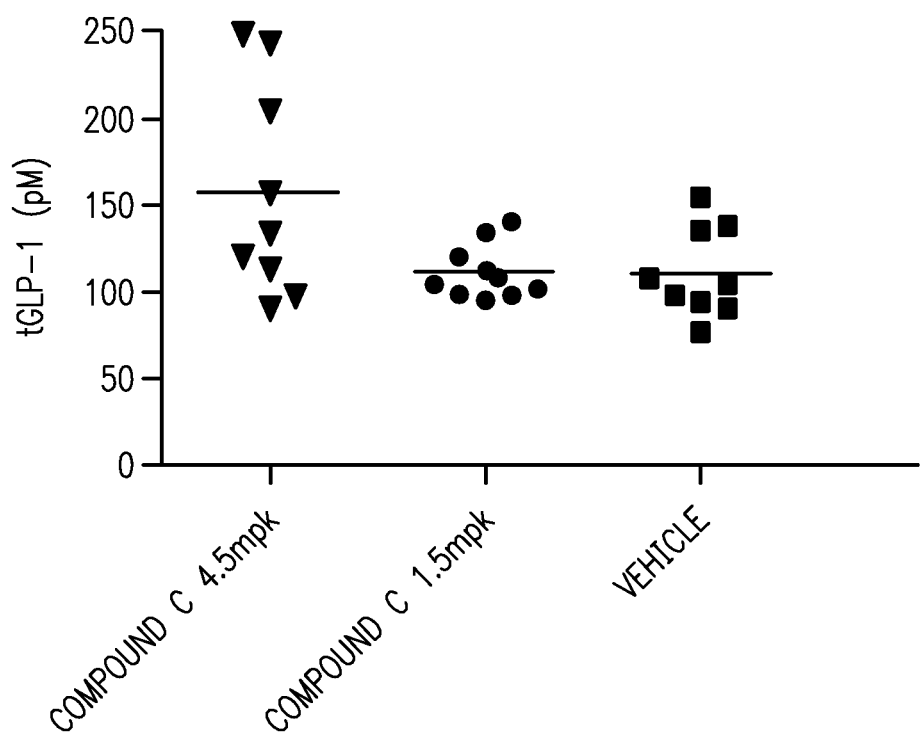

FIG. 6 shows the compound's effect on the mice's postprandial tGLP-1 after 29 days of dosing.

5. DETAILED DESCRIPTION

This invention is based on the discovery of novel and potent inhibitors of sodium glucose cotransporter 1 (SGLT1).

5.1. Definitions

Unless otherwise indicated, the term "alkyl" means a straight chain or branched hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "aryl" means an aromatic ring or an aromatic or partially aromatic ring system composed of carbon and hydrogen atoms. An aryl moiety may comprise multiple rings bound or fused together. Particular aryl moieties comprise from six to twelve carbon atoms in their rings, and are referred to as "$C_{6-12}$-aryl." Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the terms "halogen" and "halo" encompass fluorine, chlorine, bromine, and iodine.

Unless otherwise indicated, the term "heteroalkyl" refers to an alkyl moiety in which at least one of its carbon atoms has been replaced with a heteroatom (e.g., N, O or S). Particular heteroalkyl moieties are 1-4-membered, 1-10-membered and 4-20-membered, wherein the number of "members" is the number of carbon or heteroatoms making up the chain (in this case, 1-4, 1-10, or 4-20, respectively.) Examples comprise acetate, amine, amide, and ketone moieties.

Unless otherwise indicated, the term "heteroaryl" means an aryl moiety wherein at least one of its carbon atoms has been replaced with a heteroatom (e.g., N, O or S). Examples include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "locally acting" refers to compounds that have poor systemic exposure. Particular locally acting compounds have a maximum plasma concentration ($C_{max}$) of less than 250, 100, 50, or 10 nM when orally administered at a dose of 10 mg/kg to a mouse, rat or human. Systemic exposure (e.g., $C_{max}$) can be measured by methods well known in the art, including liquid chromatography mass spectrometry.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences*, 18$^{th}$ ed. (Mack Publishing, Easton Pa.: 1990) and *Remington: The Science and Practice of Pharmacy*, 19$^{th}$ ed. (Mack Publishing, Easton Pa.: 1995).

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or prevent its recurrence. A "prophylactically effective amount" of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the term "SGLT1 IC$_{50}$" is the IC$_{50}$ of a compound determined using the in vitro human SGLT1 inhibition assay described in the Examples, below.

Unless otherwise indicated, the term "SGLT1 inhibitor" refers to a compound that has an SGLT1 IC$_{50}$ of less than 100 nM. Particular SGLT1 inhibitors have an SGLT1 IC$_{50}$ of less than 50, 25 or 10 nM.

Unless otherwise indicated, the term "SGLT2 IC$_{50}$" is the IC$_{50}$ of a compound determined using the in vitro human SGLT2 inhibition assay described in the Examples, below.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, alcohol, aldehylde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-). In a particular embodiment, the term substituted refers to a derivative of that structure or moiety wherein one or more of its hydrogen atoms is substituted with alcohol, alkoxy, alkyl (e.g., methyl, ethyl, propyl, t-butyl), amide (—C(O)NH-alkyl- or -alkylNHC(O)alkyl), amidinyl (—C(NH)NH-alkyl or —C(NR)NH$_2$), amine (primary, secondary and tertiary such as alkylamino, arylamino, arylalkylamino), aryl, carbamoyl (—NHC(O)O-alkyl- or —OC(O)NH-alkyl), carbamyl (e.g., CONH$_2$, as well as CONH-alkyl, CONH-aryl, and CONH-arylalkyl), halo, haloalkyl (e.g., —CCl$_3$, —CF$_3$, —C(CF$_3$)$_3$), heteroalkyl, imine (primary and secondary), isocyanate, isothiocyanate, thiol (e.g., sulfhydryl, thioether) or urea (—NHCONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

5.2. Compounds

This invention is directed, in part, to compositions comprising and methods of using compounds of the formula:

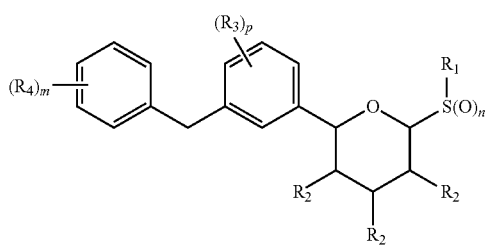

and pharmaceutically acceptable salts, dimers or trimers thereof, wherein: $R_1$ is hydrogen or optionally substituted $C_{1-10}$-alkyl, $C_{1-5}$-cycloalkyl, or 5-membered heterocycle, which optional substitution is with one or more $R_{1A}$; each $R_{1A}$ is independently amino, ester, amide, thiol, carboxylic acid, cyano, halo, hydroxyl, or optionally substituted $C_{1-4}$-alkoxy, $C_{1-5}$-cycloalkyl, or 5-membered heterocycle, which optional substitution is with one or more $R_{1B}$; each $R_{1B}$ is independently $C_{1-4}$-alkyl, halo, or hydroxyl; n is 0, 1, or 2; each $R_2$ is independently F or $OR_{2A}$, wherein each $R_{2A}$ is independently hydrogen, $C_{1-4}$-alkyl, or acyl; each $R_3$ is independently halo, hydroxyl, or optionally substituted $C_{1-10}$-alkyl or $C_{1-10}$-alkoxy, which optional substitution is with one or more $R_{3A}$; each $R_{3A}$ is independently amino, ester, amide, thiol, carboxylic acid, cyano, halo, hydroxyl, or optionally substituted $C_{1-4}$-alkoxy, $C_{1-5}$-cycloalkyl, or 5-membered heterocycle, which optional substitution is with one or more $R_{3B}$; each $R_{3B}$ is independently $C_{1-4}$-alkyl, amino, cyano, halo, or hydroxyl; p is 0, 1, or 2; each $R_4$ is independently $R_{4A}$, $-N(R_{4A})(R_{4B})$, $-OR_{4A}$, $-SR_{4A}$, $-S(O)R_{4A}$, or $-S(O)_2R_{4A}$; $R_{4A}$ is optionally substituted $C_{4-20}$-alkyl or 4-20-membered heteroalkyl, which optional substitution is with one or more $R_{4C}$, and which is optionally attached to another $R_{4A}$ moiety to provide a dimer or trimer; $R_{4B}$ is hydrogen or $R_{4A}$; each $R_{4C}$ is independently amino, amido, azo, carbonyl, carboxyl, cyano, formyl, guanidino, halo, hydroxyl, imido, imino, isothiocyanate, nitrile, nitro, nitroso, nitroxy, oxo, sulfanyl, sulfinyl, sulfonyl, thial, thiocyanate, thione, thiourea, urea, or $X_1$, $X_1$-$L_1$-$X_2$, or $X_1$-$L_1$-$X_2$-$L_2$-$X_3$, wherein each of $X_1$, $X_2$ and $X_3$ is independently optionally substituted $C_{1-4}$-alkyl, $C_{1-6}$-cycloalkyl, 5- or 6-membered heterocycle, or aryl, which optional substitution is with one or more $R_{4D}$, and each of $L_1$ and $L_2$ is independently optionally substituted $C_{1-6}$-alkyl or 1-10-membered heteroalkyl, which optional substitution is with one or more of $R_{4E}$; each $R_{4D}$ is independently $R_{4E}$ or $C_{1-6}$-alkyl optionally substituted with one or more of $R_{4E}$; each $R_{4E}$ is independently amino, amido, azo, carbonyl, carboxyl, cyano, formyl, guanidino, halo, hydroxyl, imido, imino, isothiocyanate, nitrile, nitro, nitroso, nitroxy, oxo, sulfanyl, sulfinyl, sulfonyl, thial, thiocyanate, thione, or urea; and m is 1, 2 or 3.

One embodiment of the invention encompasses compounds of the formula:

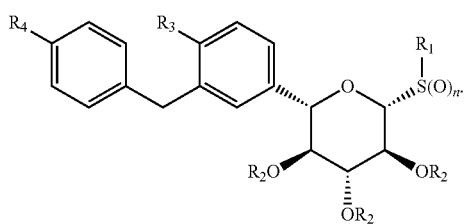

and pharmaceutically acceptable salts thereof. Particular compounds are of the formula:

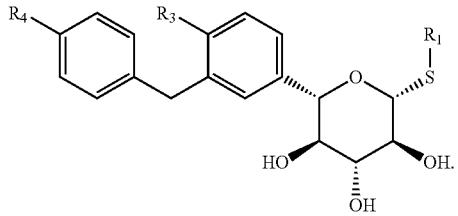

Referring to the formulae shown herein, particular compounds of the invention are monomers.

Referring to the formulae shown herein, in particular compounds of the invention, $R_1$ is optionally substituted $C_{1-4}$-alkyl (e.g., methyl, ethyl, propyl).

Referring to the formulae shown herein, in particular compounds of the invention, n is 0. In others, n is 1. In others, n is 2.

Referring to the formulae shown herein, in particular compounds of the invention, $R_2$ is $OR_{2A}$. In one embodiment, at least one $R_{2A}$ is hydrogen. In one embodiment, at least one $R_{2A}$ is acyl.

Referring to the formulae shown herein, in particular compounds of the invention, $R_3$ is optionally substituted $C_{1-4}$-alkyl (e.g., methyl, ethyl, propyl). In others, $R_3$ is halo (e.g., chloro). In others, $R_3$ is optionally substituted $C_{1-4}$-alkoxy.

Referring to the formulae shown herein, in particular compounds of the invention, p is 1.

Referring to the formulae shown herein, in particular compounds of the invention, $R_4$ is $R_{4A}$. In others, $R_4$ is $-OR_{4A}$. In one embodiment, $R_{4A}$ is optionally substituted $C_{4-10}$-alkyl. In another, $R_{4A}$ is optionally substituted 4-10-membered heteroalkyl. In particular embodiments of the invention, $R_{4A}$ is: $-C_{1-10}$-alkyl-$N(R_{4C})_2$; $-C_{1-10}$-alkyl-$N(R_{4C})C(O)R_{4C}$; $-C_{1-10}$-alkyl-$C(O)N(R_{4C})_2$; $-C_{1-10}$-alkyl-$C(O)N(R_{4C})$—$C_{0-6}$-alkyl-$C(O)R_{4C}$; $-C_{1-10}$-alkyl-$C(O)N(R_{4C})$—$C_{0-6}$-alkyl-$C(O)N(R_{4C})_2$; $-C_{1-10}$-alkyl-$N(R_{4C})C(O)$—$C_{0-6}$-alkyl-$N(R_{4C})_2$; or $-C_{1-10}$-alkyl-$N(R_{4C})C(O)$—$C_{0-6}$-alkyl-$N(R_{4C})C(O)R_{4C}$.

Particular compounds of the invention are SGLT1 inhibitors, and have an SGLT1 $IC_{50}$ of less than 50, 25 or 10 nM.

Particular compounds of the invention act locally in the gut, and have low systemic exposure. Low systemic exposure can afford benefits including fewer off-target adverse effects and reduced inhibition of SGLT2.

Examples of low systemic exposure include a maximum concentration ($C_{max}$) of less than 3000 nM when orally administered to mice at a dose of 150 mg/kg; a $C_{max}$ of less than 500 nM when orally administered to mice at a dose of 50 mg/kg; or a $C_{max}$ of less than 100 nM when orally administered to mice at a dose of 15 mg/kg. In a particular embodiment of the invention, a compound of the invention has a plasma $C_{max}$ of less than 250, 100, 50, or 10 nM when orally administered at a dose of 10 mg/kg to a mouse, rat or human. Exposure is determined by measuring plasma drug content using liquid chromatography-mass spectrometry, a technique well known in the art.

5.3. Synthesis

Compounds of the invention can be prepared by methods known in the art, by the general and specific methods described herein, and by adaptation or modification of these methods, which may be readily accomplished by those of ordinary skill in the art.

Scheme 1 represents one general approach as applied to a particular subset of compounds of the invention.

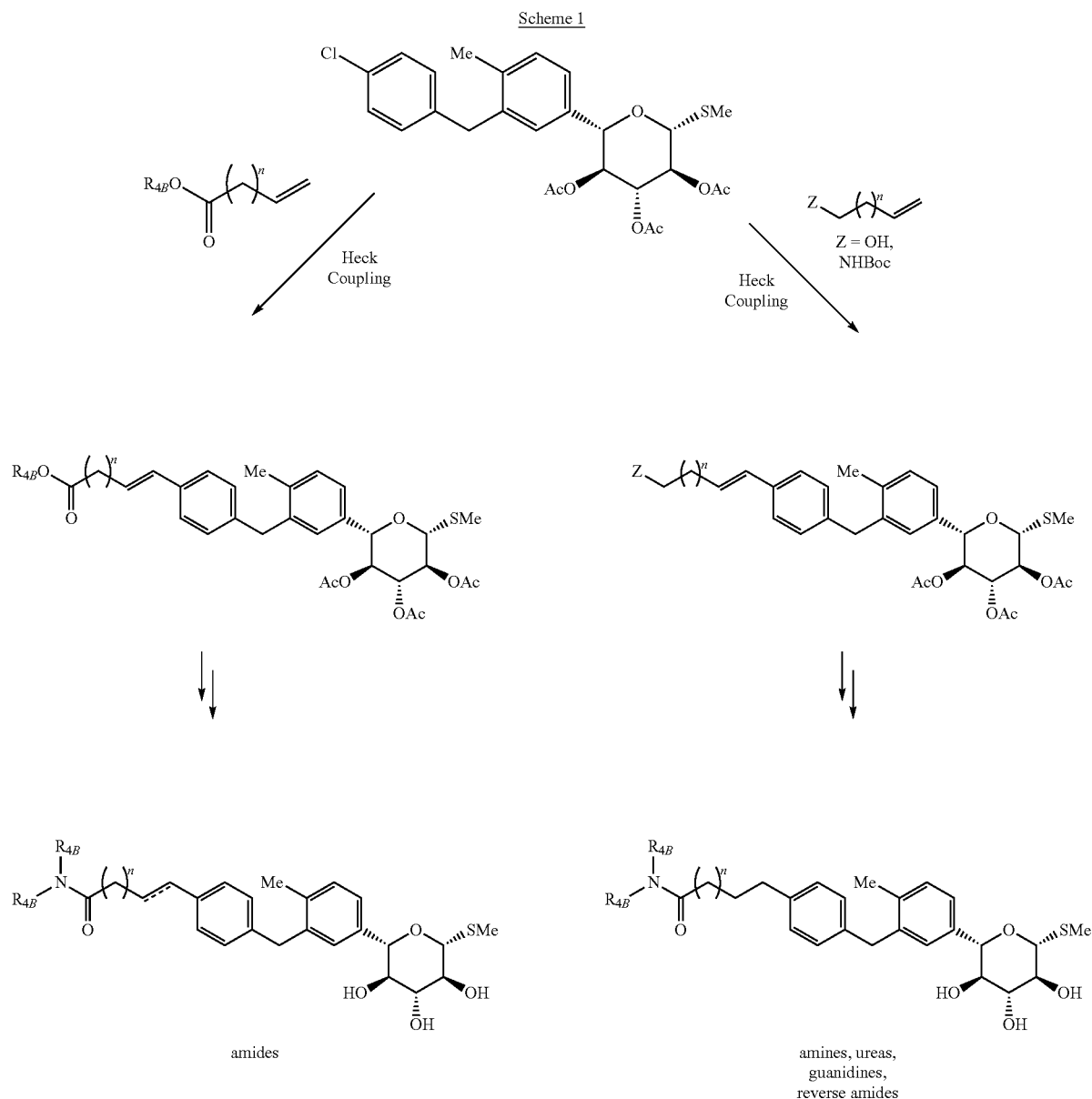
Scheme 1
Another general approach is represented by Scheme 2:
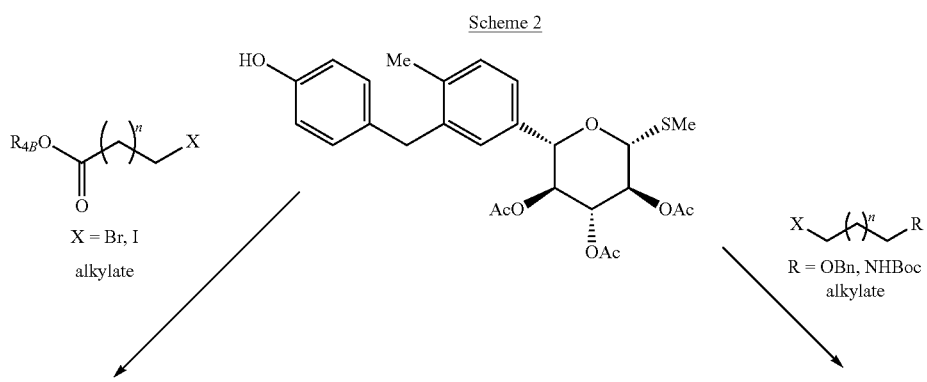
Scheme 2

11

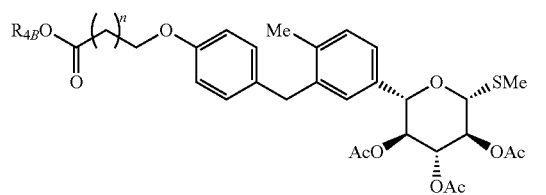

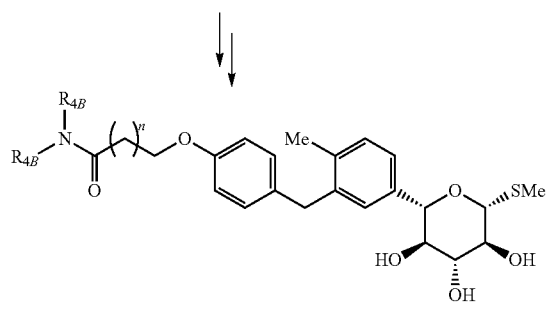

amides

12

-continued

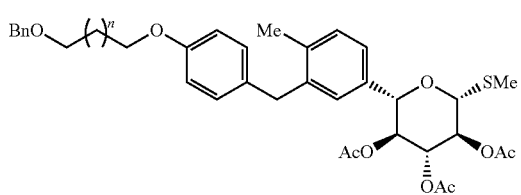

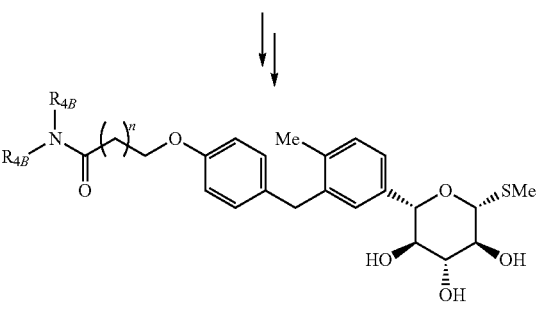

amines, ureas,
guanidines,
reverse amides

Referring to schemes 1 and 2, a general procedure for the Heck reaction of an aryl chloride is shown below, with reference to a specific compound disclosed in the Examples:

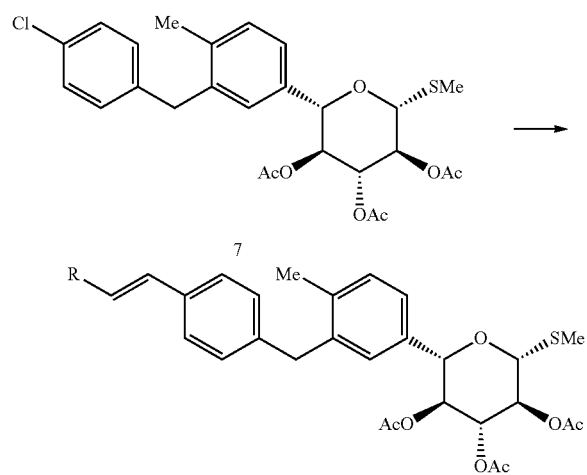

Here, a microwave vial is charged with (2S,3S,4R,5S,6R)-2-(3-(4-chlorobenzyl)-4-methylphenyl)-6-(methylthio)tetrahydro-2H-pyran-3,4,5-triyltriacetate (7, 1.0 equivalents), Heck olefin substrate (3.0 equivalents), Pd$_2$dba$_3$ (0.2 equivalents), tri(tert-butyl)phosphonium tetrafluoroborate (0.8 equivalents), dicyclohexylmethylamine (3.0 equiv), and N-methylpyrrolidinone (0.1 M). The reaction is heated in a microwave at 160° C. for 20 minutes. The reaction is filtered over Celite with excess EtOAc. The organic layer is washed with H$_2$O, saturated aqueous NaHSO$_4$, and brine. It is dried with mgSO$_4$ and concentrated in vacuo. Flash chromatography provides the Heck adduct.

A general procedure for the alkylation of a phenol is shown below, with reference to a specific compound disclosed in the Examples:

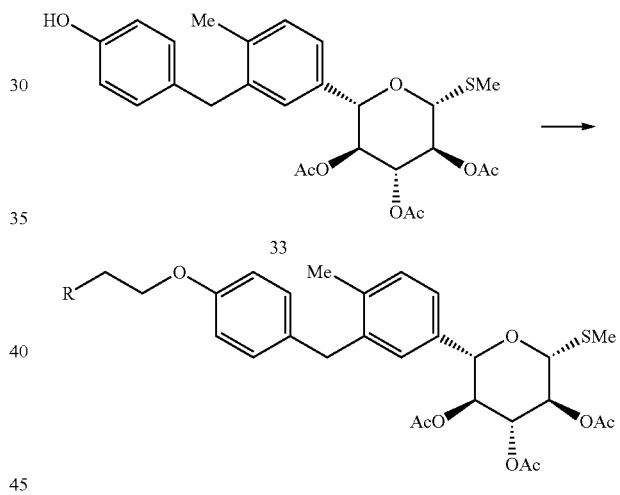

Here, to a mixture of (2S,3S,4R,5S,6R)-2-(3-(4-hydroxybenzyl)-4-methylphenyl)-6-(methylthio)tetrahydro-2H-pyran-3,4,5-triyltriacetate (33, 1 equivalents) and K$_2$CO$_3$ (5 equivalents) in DMF under nitrogen is added alkyl halide (1.5 equivalents). The reaction is stirred overnight at room temperature, then diluted with Et$_2$O. The organic layer is washed with saturated aqueous NaHCO$_3$ and brine (with back extraction), dried over MgSO$_4$, filtered, and concentrated under vacuum. The residue is purified by silica gel flash chromatography.

A general procedure for HATU amide coupling is shown below:

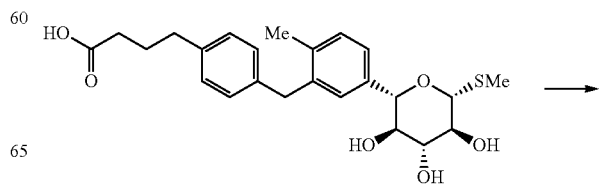

-continued

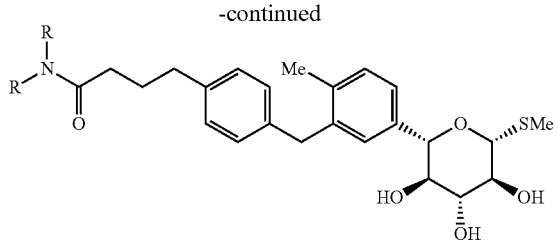

Here, carboxylic acid substrate (1 equivalents), amine (1.5 equivalents), HATU (1.2 equivalents), and DIPEA (3 equivalents) are combined in $CH_3CN$ (0.2 M) and stirred for 1-16 hours at room temperature. The reaction is quenched with saturated aqueous $NaHCO_3$ and extracted twice with EtOAc. The combined organic layers are washed with brine, dried with $MgSO_4$, filtered, and concentrated under vacuum. The residue is purified by preparative HPLC to provide the desired compound after lyophilization.

A general procedure for amine nucleophilic displacement of an alkyl mesylate is shown below:

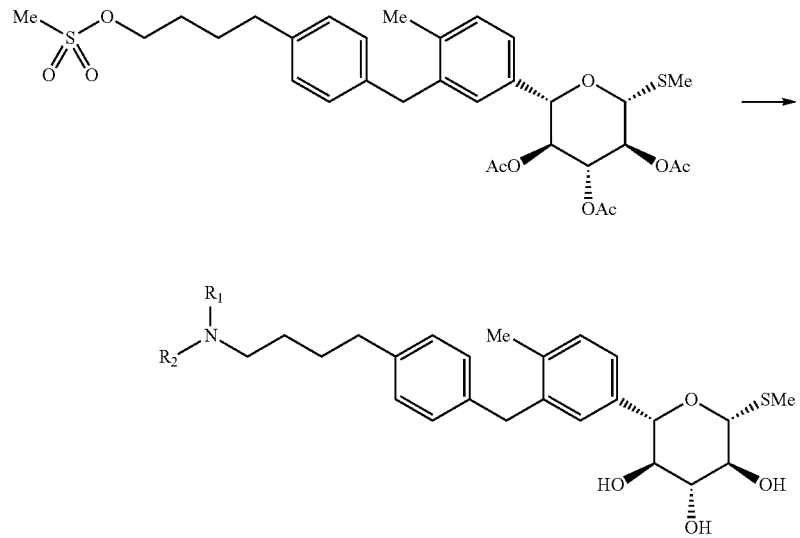

Here, amine (2.5 equivalents), catalytic sodium iodide, and alkyl mesylate (1.0 equivalents) are heated to 80° C. in isopropanol/$CH_3CN$ (1:1 v:v). Upon complete conversion, the reaction is cooled to room temperature, diluted with MeOH, and sodium methoxide is added. Acetate deprotection is typically complete within 30 minutes. Volatiles are removed in vacuo and the crude residue is purified by preparative HPLC to provide the desired compound after lyophilization.

A general procedure for urea formation from primary amine is shown below:

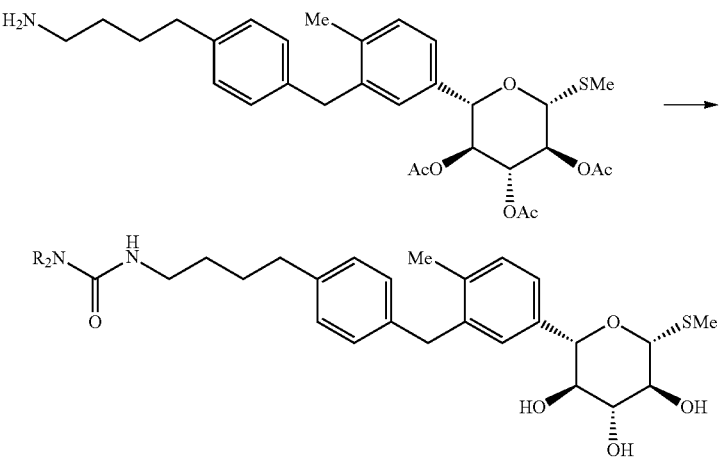

Here, to a solution of alkyl amine (1 equivalents) and 4-nitrophenyl chloroformate (1.2 equivalents) in $CH_2Cl_2$ is added triethylamine (1.4 equivalents). The reaction is stirred for 4 hours, and then amine ($R_2NH$, 1.4 equivalents) and DIPEA (1.5 equivalents) are added. The reaction is stirred for 90 minutes, then diluted with EtOAc, washed with saturated aqueous $NaHCO_3$ and brine (with back extraction), dried over $MgSO_4$, filtered, and concentrated under vacuum. The crude residue is diluted with MeOH, and sodium methoxide was added. Acetate deprotection is typically complete within 30 minutes. Volatiles are removed in vacuo and the crude residue is purified by preparative HPLC to provide the desired compound after lyophilization A general procedure for guanidine formation from primary amine is shown below:

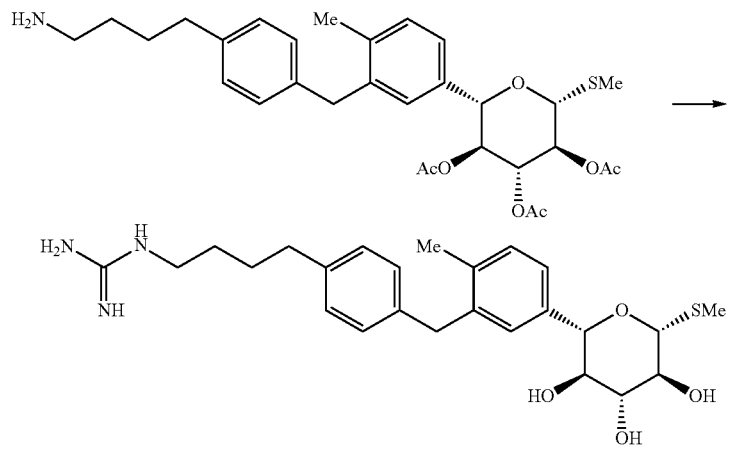

Here, to a solution of alkyl amine (1 equivalents 0.090 mmol) and 3,5-dimethyl-1H-pyrazole-1-carboximidamide nitrate (3.6 equivalents) in $CH_3CN$ are added DIPEA (4 equivalents). The reaction is heated at 70° C. for 2 hours, then cooled to room temperature and concentrated under vacuum. The residue is dissolved in MeOH and treated with sodium methoxide for 1 hour. The reaction is concentrated under vacuum, and the residue purified by preparative HPLC to provide the desired compound after lyophilization.

5.4. Methods of Use

This invention encompasses methods of treating or managing cardiovascular diseases and disorders, metabolic diseases and disorders, bowel diseases and disorders, and certain types of cancer.

One embodiment of the invention encompasses methods of treating a cardiovascular or metabolic disease or disorder, which comprises administering to a patient in need thereof a safe and efficacious amount of an SGLT1 inhibitor of the invention (i.e., a compound disclosed herein). Particular cardiovascular diseases and disorders diseases include atherosclerosis, cardiovascular disease, congestive heart failure, diabetes (Type 1 and 2), disorders associated with hemoconcentration (e.g., hemochromatosis, polycythemia vera), hyperglycaemia, hypertension, hypomagnesemia, hyponatremia, lipid disorders, obesity, renal failure (e.g., stage 1, 2, or 3 renal failure), and Syndrome X. Particular patients suffer from, or are at risk of suffering from, type 2 diabetes mellitus.

Another embodiment of the invention encompasses methods of treating or managing constipation-predominant irritable bowel syndrome (IBS-C) or chronic constipation a patient, which comprise administering to a patient in need thereof a safe and efficacious amount of an SGLT1 inhibitor of the invention.

Another embodiment of the invention encompasses methods of treating or managing cancer in a patient, which comprise administering to a patient in need thereof a safe and efficacious amount of an SGLT1 inhibitor of the invention. Particular types of cancer are those in which the cancer cells exhibit enhanced SGLT gene expression. See, e.g., Calvo, M. B., et al., Int. J. Endocrinology, vol. 2010, article ID 205357. Examples include pancreatic cancer and lung cancer.

In certain embodiments of the invention, a compound of the invention is administered adjunctively with another drug or pharmacologically active ingredient ("therapeutic agent.") In the treatment of a cardiovascular or metabolic disease or disorder, examples of second therapeutic agents include those known to be useful in its treatment, such as anti-diabetic agents; anti-hyperglycemic agents; hypolipidemic/lipid lowering agents; anti-obesity agents; anti-hypertensive agents and appetite suppressants.

Examples of anti-diabetic agents include bisguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, and dipeptidyl peptidase IV (DPP-4) inhibitors.

Examples of meglitinides include nateglinide (Novartis) and KAD1229 (PF/Kissei).

Examples of thiazolidinediones include Mitsubishi's MCC-555 (disclosed in U.S. Pat. No. 5,594,016), Glaxo-Welcome's GL-262570, englitazone (CP-68722, Pfizer), darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Examples of PPAR-alpha agonists, PPAR-gamma agonists and PPAR alpha/gamma dual agonists include muraglitizar, peliglitazar, AR-HO39242 (Astra/Zeneca), GW-409544 (Glaxo-Wellcome), GW-501516 (Glaxo-Wellcome), KRP297 (Kyorin Merck) as well as those disclosed by Murakami et al, Diabetes 47, 1841-1847 (1998), WO 01/21602 and in U.S. Pat. No. 6,653,314.

Examples of aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Examples of DPP-4 inhibitors include sitagliptin (Januvia®, Merck), vildagliptin (Galvus®, Novartis), saxagliptin (Onglyza®, BMS-477118), linagliptin (BI-1356), dutogliptin (PHX1149T), gemigliptin (LG Life Sciences), alogliptin (SYR-322, Takeda), those disclosed in WO99/38501, WO99/46272, WO99/67279 (PROBIODRUG), WO99/67278 (PROBIODRUG), and WO99/61431 (PROBIODRUG), NVP-DPP728A (1-[[[2-[(5-cyanopyridin-2-yl)amino]ethyl]amino]acetyl]-2-cyano-(S)-pyrro-lidine) (Novartis) as disclosed by Hughes et al, Biochemistry, 38(36), 11597-11603, 1999, TSL-225 (tryptophyl-1,2,3,4-tetrahydroisoquinoline-3-carboxylic acid (disclosed by Yamada et al, *Bioorg. & Med. Chem. Lett.* 8 (1998) 1537-1540), 2-cyanopyrrolidides and 4-cyanopyrrolidides, as disclosed by Ashworth et al, *Bioorg. & Med. Chem. Lett.*, Vol. 6, No. 22, pp 1163-1166 and 2745-2748 (1996), the compounds disclosed in U.S. application Ser. No. 10/899,641, WO 01/868603 and U.S. Pat. No. 6,395,767, employing dosages as set out in the above references.

Examples of anti-hyperglycemic agents include glucagon-like peptide-1 (GLP-1), GLP-1(1-36) amide, GLP-1(7-36) amide, GLP-1(7-37) (as disclosed in U.S. Pat. No. 5,614,492), exenatide (Amylin/Lilly), LY-315902 (Lilly), liraglutide (NovoNordisk), ZP-10 (Zealand Pharmaceuticals A/S), CJC-1131 (Conjuchem Inc), and the compounds disclosed in WO 03/033671.

Examples of hypolipidemic/lipid lowering agents include MTP inhibitors, HMG CoA reductase inhibitors, squalene synthetase inhibitors, fibric acid derivatives, ACAT inhibitors, lipoxygenase inhibitors, cholesterol absorption inhibitors, Na+/bile acid co-transporter inhibitors, up-regulators of LDL receptor activity, bile acid sequestrants, cholesterol ester transfer protein (e.g., CETP inhibitors, such as CP-529414 (Pfizer) and JTT-705 (Akros Pharma)), and nicotinic acid and derivatives thereof.

Examples of MTP inhibitors include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440.

Examples of HMG CoA reductase inhibitors include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl]pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322.

Examples of hypolipidemic agents include pravastatin, lovastatin, simvastatin, atorvastatin, fluvastatin, cerivastatin, atavastatin, and ZD-4522.

Examples of phosphinic acid compounds useful in inhibiting HMG CoA reductase include those disclosed in GB 2205837.

Examples of squalene synthetase inhibitors include α-phosphono-sulfonates disclosed in U.S. Pat. No. 5,712,396, those disclosed by Biller et al., *J. Med. Chem.* 1988, Vol. 31, No. 10, pp 1869-1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., et al., *Current Pharmaceutical Design,* 2, 1-40 (1996).

Examples of additional squalene synthetase inhibitors suitable for use herein include the terpenoid pyrophosphates disclosed by P. Ortiz de Montellano et al., *J. Med. Chem.,* 1977, 20, 243-249, the farnesyl diphosphate analog A and presqualene pyrophosphate (PSQ-PP) analogs as disclosed by Corey and Volante, *J. Am. Chem. Soc.* 1976, 98, 1291-1293, phosphinylphosphonates reported by McClard, R. W. et al., *J.A.C.S.,* 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

Examples of fibric acid derivatives which may be employed in combination the compounds of this invention include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex, Policexide), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

Examples of ACAT inhibitor that may be employed in combination compounds of this invention include those disclosed in *Drugs of the Future* 24, 9-15 (1999), (Avasimibe); Nicolosi et al., *Atherosclerosis* (Shannon, Irel).

(1998), 137(1), 77-85; Ghiselli, Giancarlo, *Cardiovasc. Drug Rev.* (1998), 16(1), 16-30; Smith, C., et al., *Bioorg. Med. Chem. Lett.* (1996), 6(1), 47-50; Krause et al., Editor(s): Ruffolo, Robert R., Jr.; Hollinger, Mannfred A., *Inflammation: Mediators Pathways* (1995), 173-98, Publisher: CRC, Boca Raton, Fla.; Sliskovic et al., *Curr. Med. Chem.* (1994), 1(3), 204-25; Stout et al., *Chemtracts: Org. Chem.* (1995), 8(6), 359-62, or TS-962 (Taisho Pharmaceutical Co. Ltd).

Examples of hypolipidemic agents include up-regulators of LD2 receptor activity, such as MD-700 (Taisho Pharmaceutical Co. Ltd) and LY295427 (Eli Lilly).

Examples of cholesterol absorption inhibitors include SCH48461 (Schering-Plough), as well as those disclosed in *Atherosclerosis* 115, 45-63 (1995) and *J. Med. Chem.* 41, 973 (1998).

Examples of ileal Na$^+$/bile acid co-transporter inhibitors include compounds as disclosed in *Drugs of the Future*, 24, 425-430 (1999).

Examples of lipoxygenase inhibitors include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., *Brit. J. Pharmacology* (1997) 120, 1199-1206, and Cornicelli et al., *Current Pharmaceutical Design*, 1999, 5, 11-20.

Examples of suitable anti-hypertensive agents for use in combination with compounds of this invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/All antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples anti-obesity agents include beta 3 adrenergic agonists, a lipase inhibitors, serotonin (and dopamine) reuptake inhibitors, thyroid receptor beta drugs, 5HT$_{2c}$ agonists, (such as Arena APD-356); MCHR1 antagonists such as Synaptic SNAP-7941 and Takeda T-226926, melanocortin receptor (MC4R) agonists, melanin-concentrating hormone receptor (MCHR) antagonists (such as Synaptic SNAP-7941 and Takeda T-226926), galanin receptor modulators, orexin antagonists, CCK agonists, NPY1 or NPY5 antagonsist, NPY2 and NPY4 modulators, corticotropin releasing factor agonists, histamine receptor-3 (H3) modulators, 11-beta-HSD-1 inhibitors, adinopectin receptor modulators, monoamine reuptake inhibitors or releasing agents, a ciliary neurotrophic factor (CNTF, such as AXOKINE by Regeneron), BDNF (brain-derived neurotrophic factor), leptin and leptin receptor modulators, cannabinoid-1 receptor antagonists (such as SR-141716 (Sanofi) or SLV-319 (Solvay)), and/or an anorectic agent.

Examples of beta 3 adrenergic agonists include AJ9677 (Takeda/Dainippon), L750355 (Merck), or CP331648 (Pfizer) or other known beta 3 agonists, as disclosed in U.S. Pat. Nos. 5,541,204, 5,770,615, 5,491,134, 5,776,983 and 5,488,064.

Examples of lipase inhibitors include orlistat and ATL-962 (Alizyme).

Examples of serotonin (and dopoamine) reuptake inhibitors (or serotonin receptor agonists) include BVT-933 (Biovitrum), sibutramine, topiramate (Johnson & Johnson) and axokine (Regeneron).

Examples of thyroid receptor beta compounds include thyroid receptor ligands, such as those disclosed in WO97/21993 (U. Cal SF), WO99/00353 (KaroBio) and GB98/284425 (KaroBio).

Examples of monoamine reuptake inhibitors include fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine and mazindol.

Examples of anorectic agents include dexamphetamine, phentermine, phenylpropanolamine, and mazindol.

5.5. Pharmaceutical Formulations

This invention encompasses pharmaceutical compositions comprising a compound of the invention optionally in combination with one or more second active ingredients, such as those described above in Section 5.4.

Certain pharmaceutical compositions are single unit dosage forms suitable for oral administration to a patient. Discrete dosage forms suitable for oral administration include tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., *Remington's Pharmaceutical Sciences*, 18th ed. (Mack Publishing, Easton Pa.: 1990).

Typical oral dosage forms are prepared by combining the active ingredient(s) in an intimate admixture with at least one excipient according to conventional pharmaceutical compounding techniques. Because of their ease of administration, tablets and capsules represent the most advantageous oral dosage unit forms. If desired, tablets can be coated by standard aqueous or nonaqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

Particular compounds of the invention may be bound to polymers and/or beads, which can be used to calibrate their delivery, metabolism and/or activity. For example, certain compounds can be bound via $R_{44}$ to beads designed for enteric delivery to patients.

6. EXAMPLES

6.1. Preparation of (2S,3S,4R,5S,6R)-2-(3-(4-chlorobenzyl)-4-methylphenyl)-6-(methylthio)tetrahydro-2H-pyran-3,4,5-triyl triacetate (7)

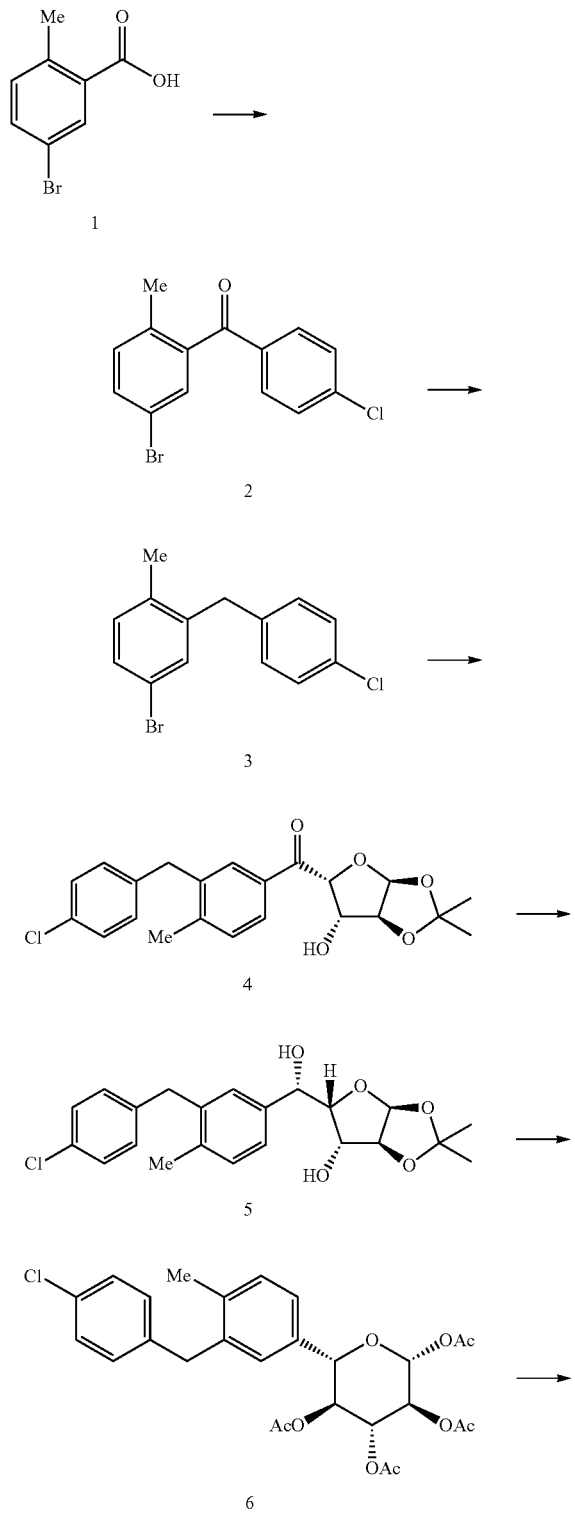

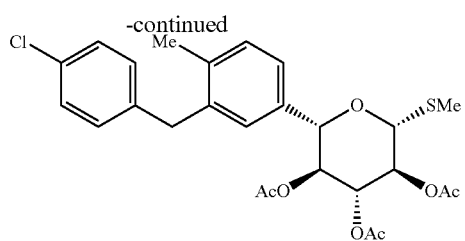

Preparation of (5-bromo-2-methylphenyl)(4-chlorophenyl)methanone (2)

2-Methyl-4-bromobenzoic acid (1, 26.0 g, 121 mmol) and oxalyl chloride (13.2 mL, 152 mmol) were suspended in 520 mL of $CH_2Cl_2$. A catalytic amount of DMAP (0.5 mL) was added dropwise and the reaction was stirred at room temperature until the reaction become homogenous. The volatiles were removed in vacuo. The crude material was dissolved in 200 mL of $CH_2Cl_2$ and N,O-dimethylhydroxylamine hydrochloride (23.6 g, 242 mmol) was added. The reaction was cooled to 0° C. and triethylamine (55 mL, 399 mmol) was slowly added. Upon completion of addition of triethylamine, the reaction was warmed to room temperature and stirred overnight. The reaction was quenched with 50% saturated aqueous $NaHSO_4$. The aqueous layer was extracted twice with $CH_2Cl_2$. The combined organic layers were washed with brine, dried over $Na_2SO_4$, filtered, and the solvent removed in vacuo. The resulting Weinreb amide (31.3 g, 99% yield) was used without further purification in the next step.

The Weinreb amide (31.3 g, 121 mmol) was taken up in 250 mL of dry THF. 4-Chloromagnesium bromide (1M in $Et_2O$, 182 mL, 182 mmol) was added at room temperature, and the reaction stirred for 2 hours. If the reaction was not complete, additional Grignard reagent was added until LCMS indicated reaction completion. The reaction was quenched with a solution of saturated aqueous $NH_4Cl$/brine (1:1 v:v) and extracted twice with EtOAc. The combined organic layers were washed with brine, dried over $MgSO_4$, filtered, and the solvent removed in vacuo. (5-Bromo-2-methylphenyl)(4-chlorophenyl)methanone (2, 37.0 g, 99% yield) was used without further purification in the next step.

$^1$H NMR (400 MHz, CHLOROFORM-d) δ ppm 7.74 (d, J=8.3 Hz, 2H), 7.53 (dd, J=8.1, 2.0 Hz, 1H), 7.46 (d, J=8.3 Hz, 2H), 7.42 (d, J=2.0 Hz, 1H), 7.18 (d, J=8.1 Hz, 1H), 2.26 (s, 3H). GCMS ($CH_4$—Cl) $[M+H]^+$=309.

Preparation of 4-bromo-2-(4-chlorobenzyl)-1-methylbenzene (3)

(5-Bromo-2-methylphenyl)(4-chlorophenyl)methanone (2, 37.0 g, 121 mmol) and triethylsilane (77.3 mL, 484 mmol) were dissolved in 300 mL of $CH_3CN$ and cooled to 0° C. $BF_3OEt_2$ (91 mL, 726 mmol) was added and the reaction was heated to 60° C. for 2 hours. GCMS was used to monitor the reaction. Upon completion, the reaction was cooled to 0° C. and quenched with 500 mL saturated aqueous NaHCO$_3$. The aqueous phase was extracted twice with EtOAc. The combined organic layers were washed with H$_2$O and brine, dried over Na$_2$SO$_4$, filtered, and the solvent removed in vacuo. The crude solid was slurried in 20% EtOAc/hexanes and passed over a silica plug to remove residual salts. Concentration of the filtrate provided the title compound as a white solid (22.0 g, 62% yield). $^1$H NMR (400 MHz, CHLOROFORM-d) δ ppm 7.22 (d, J=2.0 Hz, 1H), 7.21-7.31 (m, 3H), 7.04 (d, J=8.3 Hz, 2H), 7.04 (d, J=8.1 Hz, 2H), 3.91 (s, 2H), 2.17 (s, 3H). GCMS (CH$_4$—Cl) [M+H]$^+$=295.

Preparation of (3-(4-chlorobenzyl)-4-methylphenyl) ((3aS,5R,6S,6aS)-6-hydroxy-2,2-dimethyltetrahydrofuro[2,3-d][1,3]dioxol-5-yl)methanone (4)

To a solution of ((3aS,5R,6S,6aS)-6-hydroxy-2,2-dimethyltetrahydrofuro[2,3-d][1,3]dioxol-5-yl)(morpholino)methanone (25.3 g, 92.6 mmol) in THF (200 mL) under nitrogen at 0° C. was added tert-butyl magnesium chloride (1 M in THF, 100 mL, 100 mmol). This solution was stirred at 0° C. for 30 minutes. Meanwhile, a solution of 4-bromo-2-(4-chlorobenzyl)-1-methylbenzene (3, 32.9 g, 111.1 mmol) in THF (330 mL) under nitrogen was cooled to −78° C. n-Butyllithium (2.5 M in hexanes, 48 mL, 120 mmol) was added dropwise via syringe and stirred for 10 min. The magnesium alkoxide solution was transferred via cannula into the aryllithium solution at −78° C. The reaction was stirred for 30 min at −78° C., allowed to warm to room temperature and stirred for 60 min, quenched with 500 mL of a 1:1 (v:v) solution of saturated aqueous NH$_4$Cl/brine. The aqueous layer was extracted two times with 300 mL of EtOAc. The combined organic layers were washed with brine, dried over MgSO$_4$, filtered, and concentrated under vacuum. The crude residue was taken up in 100 mL of EtOAc and heated until most of the solids dissolved. 250 mL of hexanes was added and the flask was chilled in an ice bath for two hours. The white precipitate was filtered off and washed with 20% EtOAc/hexane, providing the title compound as a white solid (26.09 g, 70% yield). $^1$H NMR (400 MHz, CHLOROFORM-d) δ ppm 7.88 (dd, J=7.8, 1.8 Hz, 1H), 7.76 (d, J=1.5 Hz, 1H), 7.29 (d, J=8.1 Hz, 1H), 7.26 (d, J=8.3 Hz, 2H), 7.05 (d, J=8.3 Hz, 2H), 6.08 (d, J=3.8 Hz, 1H), 5.28 (d, J=2.8 Hz, 1H), 4.59 (d, J=3.5 Hz, 1H), 4.57 (t, J=3.2 Hz, 1H), 4.01 (s, 2H), 3.06 (d, J=4.0 Hz, 1H), 2.30 (s, 3H), 1.37 (s, 3H). MS (ES+) [M+H]$^+$=403.

Preparation of (3aS,5S,6R,6aS)-5-((S)-(3-(4-chlorobenzyl)-4-methylphenyl)(hydroxy)-methyl)-2,2-dimethyltetrahydrofuro[2,3-d][1,3]dioxol-6-ol (5)

(3-(4-chlorobenzyl)-4-methyl phenyl)((3aS,5R,6S,6aS)-6-hydroxy-2,2-dimethyltetrahydrofuro[2,3-d][1,3]dioxol-5-yl)methanone (4, 26.1 g, 64.9 mmol) and CeCl$_3$.7H$_2$O (29.0 g, 77.9 mmol) were suspended in 520 mL of MeOH. Sodium borohydride (982 mg, 26.0 mmol, dissolved in 10 mL of 1N aqueous NaOH) was added and the reactants slowly went into solution over about 5 minutes. Another 100 mg (2.6 mmol) of sodium borohydride was added to push the reaction to completion. The reaction was stirred for 10 minutes and quenched with 500 mL of saturated aqueous NH$_4$Cl. Most of the MeOH was removed in vacuo and the residual solvents were diluted with a 1:1 (v:v) solution of saturated aqueous NH$_4$Cl:brine. The aqueous layer was extracted three times with 500 mL of EtOAc. The combined organic layers were washed with brine, dried over MgSO$_4$, filtered, and concentrated under vacuum. The crude product was used without further purification in the next step (26.2 g, 99% yield, >10:1 d.r.). $^1$H NMR (400 MHz, CHLOROFORM-d) δ ppm 7.14-7.31 (m, 5H), 7.04 (d, J=8.3 Hz, 2H), 6.04 (d, J=3.8 Hz, 1H), 5.24 (t, J=3.4 Hz, 1H), 4.51 (d, J=3.8 Hz, 1H), 4.14-4.21 (m, 2H), 4.04 (d, J=1.5 Hz, 1H), 3.97 (s, 2H), 2.77 (d, J=3.0 Hz, 1H), 2.20-2.27 (m, 3H), 1.46 (s, 3H), 1.33 (s, 3H). MS (ES+) [M+NH$_4$]$^+$=422.

Preparation of (3S,4R,5S,6S)-6-(3-(4-chlorobenzyl)-4-methylphenyl)tetrahydro-2H-pyran-2,3,4,5-tetrayl tetraacetate (6)

(3aS,5S,6R,6aS)-5-((S)-(3-(4-chlorobenzyl)-4-methylphenyl)(hydroxy)-methyl)-2,2-dimethyltetrahydrofuro[2,3-d][1,3]dioxol-6-ol (5, 26.2 g, 64.8 mmol) was suspended in 150 mL H$_2$O and 150 mL glacial acetic acid. The reaction was heated to 100° C. for 7 hours. The solvents were removed in vacuo and the crude residue was azeotroped three times from toluene. The crude material was placed on the high vacuum overnight and used in the next step without further purification.

The crude material was dissolved in 350 mL of CH$_3$CN. Triethylamine (57.5 mL, 414 mmol) and acetic anhydride (46.0 mL, 414 mmol) were added, followed by a catalytic amount of DMAP (100 mg). The reaction was stirred at room temperature for 1 hour. About 200 mL of CH$_3$CN was removed in vacuo and the remainder was diluted with 600 mL of EtoAc. The organic layer was washed twice with 50% saturated aqueous NaHSO$_4$. The acidic aqueous layers were backextracted with 300 mL of EtOAc. The combined organic layers were washed with brine, dried over MgSO$_4$, filtered, and concentrated under vacuum. The crude residue was azeotroped twice from toluene and once from hexanes to provide the title compound as an easily transferable beige solid (34.0 g, 92% yield, mixture of α and β anomers).

$^1$H NMR (400 MHz, CHLOROFORM-d) δ ppm 7.24 (d, J=8.3 Hz, 2H), 7.13-7.21 (m, 2H), 7.09 (s, 1H), 7.01 (d, J=8.3 Hz, 2H), 6.47 (d, J=3.5 Hz, 1Hα), 5.89 (d, J=8.3 Hz, 1Hβ), 5.59 (t, J=9.8 Hz, 1Hα), 5.37 (t, J=9.6 Hz, 1Hβ), 5.23-5.31 (m, 1Hα+1Hβ), 5.19 (t, J=9.6 Hz, 1Hβ), 5.14 (t, J=9.7 Hz, 1Hα), 4.82 (d, J=10.1 Hz, 1Hα), 4.51 (d, J=9.9 Hz, 1Hβ), 3.94 (s, 2H), 2.21 (s, 3Hα), 2.20 (s, 3Hα), 2.19 (s, 3Hβ), 2.11 (s, 3Hβ), 2.07 (s, 3Hβ), 2.06 (s, 3Hα), 2.04 (s, 3Hα), 2.03 (s, 3Hβ), 1.79 (s, 3Hα), 1.77 (s, 3Hβ). MS (ES+) [M+NH$_4$]$^+$=550.

Preparation of (2S,3S,4R,5S,6R)-2-(3-(4-chlorobenzyl)-4-methylphenyl)-6-(methylthio)tetrahydro-2H-pyran-3,4,5-triyl triacetate (7)

Trimethylsilyl trifluoromethanesulfonate (19.7 mL, 108.5 mmol) was added to a solution of (3S,4R,5S,6S)-6-(3-(4- chlorobenzyl)-4-methylphenyl)tetrahydro-2H-pyran-2,3,4,5-tetrayl tetraacetate (6, 33.9 g, 63.8 mmol) and thiourea (9.71 g, 128 mmol) in 340 mL of dioxane. The reaction was heated to 80° C. for two hours, at which point LCMS analysis revealed the reaction was stalled. Additional TMSOTf was added (2 mL, 10.8 mmol) and the reaction stirred for 1 hour at 80° C. The reaction was cooled to room temperature. Sequential addition of methyl iodide (11.9 mL, 191 mmol) followed by DIPEA (55.6 mL, 319 mmol) was performed, allowing the reaction to stir for 18 hours. 500 mL of H$_2$O was slowly added to quench the reaction. The aqueous layer was extracted two times with 300 mL EtOAc. The combined organic layers were washed with saturated aqueous NaHSO$_4$ and brine, dried over MgSO$_4$, filtered, and concentrated under vacuum. The crude solid was slurried in 300 mL of MeOH. Sonication resulted in the precipitation of a light beige precipitate, which was filtered and washed with cold MeOH. The filtrate was concentrated and the slurry procedure repeated once more to provide and combined with the first batch. The product was isolated as pure beta anomer as a light beige solid (20.4 g, 60% yield). $^1$H NMR (400 MHz, CHLOROFORM-d) δ ppm 7.24 (d, J=8.6 Hz, 2H), 7.10-7.18 (m, 2H), 7.05 (s, 1H), 7.00 (d, J=8.6 Hz, 2H), 5.34 (dd, J=9.6 Hz, 1H), 5.21 (dd, J=9.6 Hz, 1H), 5.12 (dd, J=9.6 Hz, 1H), 4.53 (d, J=9.9 Hz, 1H), 4.39 (d, J=9.9 Hz, 1H), 3.86-4.00 (m, 2H), 2.19 (s, 3H), 2.17 (s, 3H), 2.10 (s, 3H), 2.01 (s, 3H), 1.76 (s, 3H). MS (ES+) [M+NH$_4$]$^+$=538.

6.2. Preparation of N-(1-amino-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide (11)

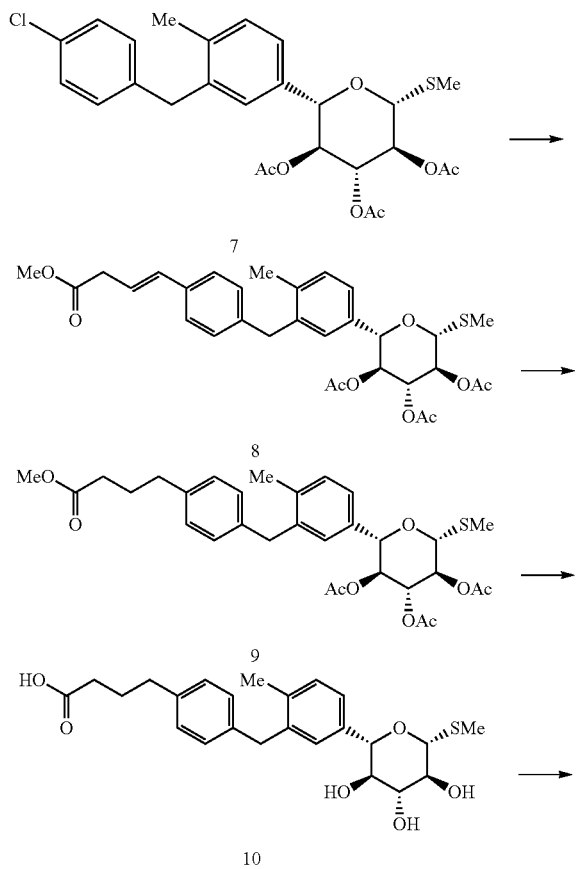

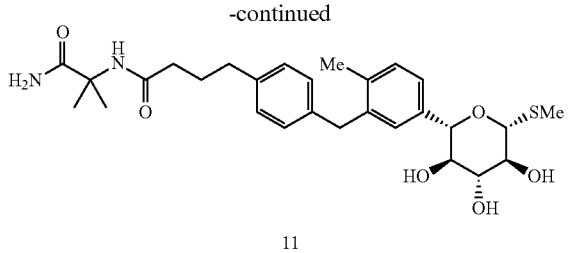

11

Preparation of (2S,3S,4R,5S,6R)-2-(3-(4-((E)-4-methoxy-4-oxobut-1-en-1-yl)benzyl)-4-methylphenyl)-6-(methylthio)tetrahydro-2H-pyran-3,4,5-triyltriacetate (8). A microwave vial was charged with (2S,3S,4R,5S,6R)-2-(3-(4-chlorobenzyl)-4-methylphenyl)-6-(methylthio)tetrahydro-2H-pyran-3,4,5-triyltriacetate (7, 1.04 g, 2.0 mmol), methyl but-5-enoate (600 mg, 6.0 mmol), Pd$_2$dba$_3$ (183 mg, 0.20 mmol), tri(tert-butyl)phosphonium tetrafluoroborate (235 mg, 0.80 mmol), dicyclohexylmethylamine (1.27 mL, 6.0 mmol), and N-methylpyrrolidinone (10 mL). The reaction was heated in the microwave at 160° C. for 20 min. The reaction was filtered over Celite with excess EtOAc. The organic layer was washed with H$_2$O, saturated aqueous NaHSO$_4$, and brine. It was dried with MgSO$_4$ and concentrated in vacuo. Silica gel flash chromatography (gradient 10-50% EtOAc/hexanes) provided Heck adduct 8 as a light yellow solid (700 mg, 60% yield). Minor amounts of isomerized olefin were observed in the $^1$H NMR. $^1$H NMR (400 MHz, CHLOROFORM-d) δ ppm 7.28-7.31 (m, 2H), 6.97-7.19 (m, 5H), 6.46 (d, J=15.9 Hz, 1H), 6.25 (dt, J=15.9, 7.1 Hz, 1H), 5.33 (dd, J=9.6 Hz, 1H), 5.21 (dd, J=9.6 Hz, 1H), 5.12 (dd, J=9.6 Hz, 1H), 4.52 (d, J=9.6 Hz, 1H), 4.39 (d, J=9.6 Hz, 1H), 3.87-4.01 (m, 2H), 3.72 (s, 2H), 3.24 (dd, J=7.1, 1.3 Hz, 2H), 2.21 (s, 3H), 2.17 (s, 3H), 2.10 (s, 3H), 2.01 (s, 3H), 1.75 (s, 3H). MS (ES+) [M+NH$_4$]$^+$=602.

Preparation of (2S,3S,4R,5S,6R)-2-(3-(4-(4-methoxy-4-oxobutyl)benzyl)-4-methylphenyl)-6-(methylthio)tetrahydro-2H-pyran-3,4,5-triyltriacetate (9)

(2S,3S,4R,5S,6R)-2-(3-(4-((E)-4-methoxy-4-oxobut-1-en-1-yl)benzyl)-4-methylphenyl)-6-(methylthio)tetrahydro-2H-pyran-3,4,5-triyl triacetate (8, 1.74 g, 3.0 mmol) was dissolved in a 1:1 (v:v) THF/MeOH solution. Pd/C (10% wet, 174 mg) was added and the reaction hydrogenated at 40 psi for 3 hours. The reaction was monitored by 1H NMR. Upon completion, the reaction was filtered over Celite with excess MeOH. Removal of solvents in vacuo provided the product as a light yellow solid (1.65 g, 94% yield). $^1$H NMR (400 MHz, CHLOROFORM-d) δ ppm 7.11-7.20 (m, 2H), 7.07 (t, J=7.8 Hz, 3H), 6.99 (d, J=8.1 Hz, 2H), 5.33 (dd, J=9.6 Hz, 1H), 5.21 (dd, J=9.6 Hz, 1H), 5.12 (dd, J=9.6 Hz, 1H), 4.52 (d, J=9.9 Hz, 1H), 4.39 (d, J=9.9 Hz, 1H), 3.85-4.00 (m, 2H), 3.67 (s, 3H), 2.61 (t, J=7.6 Hz, 2H), 2.33 (t, J=7.5 Hz, 2H), 2.21 (s, 3H), 2.18 (s, 3H), 2.10 (s, 3H), 2.01 (s, 3H), 1.93 (quin, J=7.6 Hz, 2H), 1.75 (s, 3H). MS (ES+) [M+NH$_4$]$^+$=604.

Preparation of 4-(4-(2-methyl-5-((2S,3R,4R,5S,6R)-3,4,5-trihydroxy-6-(methylthio)tetrahydro-2H-pyran-2-yl)benzyl)phenyl)butanoic acid (10)

(2S,3S,4R,5S,6R)-2-(3-(4-(4-methoxy-4-oxobutyl)benzyl)-4-methylphenyl)-6-(methylthio)tetrahydro-2H-pyran-3,4,5-triyl triacetate (9, 1.65 g, 2.81 mmol) was dissolved in a MeOH/THF/H$_2$O solution (25 mL, 2:1:2 vol. ratio). Lithium hydroxide (674 mg, 28.1 mmol) was added and the reaction stirred at room temperature for 1 hour. The reaction was acidified to pH=1-2 with saturated aqueous NaHSO₄. The acidic aqueous layer was extracted three times with EtOAc. The combined organic layers were washed with brine, dried over MgSO₄, filtered, and concentrated in vacuo. The crude product was rotovapped down once from hexanes to provide the product as white transferable solid (1.27 g, 99% yield). $^1$H NMR (400 MHz, DMSO-d$_6$) δ ppm 11.99 (s, 1H), 6.96-7.16 (m, 7H), 5.16 (d, J=5.8 Hz, 1H), 5.06 (d, J=4.3 Hz, 1H), 4.82 (d, J=5.6 Hz, 1H), 4.32 (d, J=9.6 Hz, 1H), 4.04 (d, J=9.1 Hz, 1H), 3.90 (s, 2H), 2.53 (t, J=7.3 Hz, 2H), 2.19 (t, J=7.3 Hz, 2H), 2.17 (s, 3H), 2.03 (s, 3H), 1.76 (quin, J=7.6 Hz, 2H). MS (ES+) [M+NH$_4$]$^+$=464.

Preparation of N-(1-amino-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide (11)

4-(4-(2-methyl-5-((2S,3R,4R,5S,6R)-3,4,5-trihydroxy-6-(methylthio)tetrahydro-2H-pyran-2-yl)benzyl)phenyl)butanoic acid (10, 157 mg, 0.35 mmol), 2-amino-2-methylpropanamide hydrochloride (73 mg, 0.53 mmol), HATU (161 mg, 0.42 mmol), and DIPEA (0.15 mL, 1.06 mmol) were combined in DMF (2 mL) and stirred for 2 hours at room temperature. The reaction quenched with saturated aqueous NaHCO₃ and extracted twice with EtOAc. The combined organic layers were washed with brine, dried with MgSO₄, filtered, and concentrated under vacuum. The residue was purified by preparative HPLC (C18 30×100 mm column, 5-100% CH₃CN/10 mM aqueous ammonium formate, 45 mL/min) to provide the title compound 11 after lyophilization (75 mg, 40% yield). $^1$H NMR (400 MHz, MeOH-d$_4$) δ ppm 6.96-7.23 (m, 7H), 4.39 (d, J=9.6 Hz, 1H), 4.12 (d, J=9.1 Hz, 1H), 3.96 (s, 2H), 3.33-3.51 (m, 3H), 2.59 (t, J=7.6 Hz, 2H), 2.20 (t, J=7.6 Hz, 2H), 2.20 (s, 2H), 2.14 (s, 3H), 1.87 (quin, J=7.6 Hz, 2H), 1.45 (s, 6H). MS (ES+) [M+H]$^+$=531.

6.3. Preparation of N-(2-methyl-1-(4-methylpiperazin-1-yl)-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide (12)

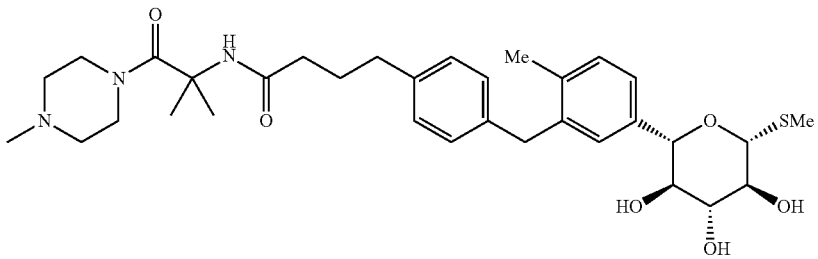

12

The same procedure was employed as for amide 11, using 2-amino-2-methyl-1-(4-methylpiperazin-1-yl)propan-1-one hydrochloride, to provide the product 12 as the bisformate salt. $^1$H NMR (400 MHz, MeOH-d$_4$) δ ppm 8.40 (s, 2H), 7.11-7.21 (m, 3H), 7.02-7.11 (m, 4H), 4.39 (d, J=9.6 Hz, 1H), 4.13 (d, J=9.1 Hz, 1H), 3.96 (s, 2H), 3.74 (br. s., 4H), 3.34-3.52 (m, 3H), 2.67 (t, J=4.6 Hz, 4H), 2.60 (t, J=7.6 Hz, 2H), 2.47 (s, 3H), 2.19 (t, J=7.6 Hz, 2H), 2.21 (s, 3H), 2.14 (s, 3H), 1.88 (quin, J=7.5 Hz, 2H), 1.44 (s, 6H). MS (ES+) [M+H]$^+$=614.

6.4. Preparation of N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide (13)

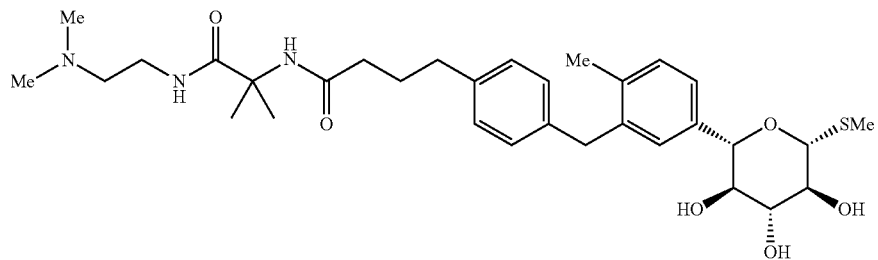

13

The same procedure was employed as for amide 11, using 2-amino-2-methyl-1-(4-methylpiperazin-1-yl)propan-1-one hydrochloride, to provide the product 13 as the formate salt. $^1$H NMR (400 MHz, MeOH-d$_4$) δ ppm 8.52 (s, 1H), 7.12-7.21 (m, 3H), 7.03-7.12 (m, 4H), 4.39 (d, J=9.6 Hz, 1H), 4.13 (d, J=9.3 Hz, 1H), 3.96 (s, 2H), 3.51 (t, J=5.6 Hz, 2H), 3.33-3.47 (m, 3H), 3.07 (t, J=4.8 Hz, 2H), 2.79 (s, 6H), 2.60 (t, J=7.6 Hz, 2H), 2.21 (s, 3H), 2.22 (t, J=7.6 Hz, 2H), 2.14 (s, 3H), 1.88 (quin, J=7.5 Hz, 2H), 1.41 (s, 6H). MS (ES+) [M+H]$^+$=602.

6.5. Preparation of (S,R,R,S,R)—N,N'-((methyl-azanediyl)bis(propane-3,1-diyl))bis(4-(4-(2-methyl-5-((2S,3R,4R,5S,6R)-3,4,5-trihydroxy-6-(methyl-thio)tetrahydro-2H-pyran-2-yl)benzyl)phenyl)butanamide) (14)

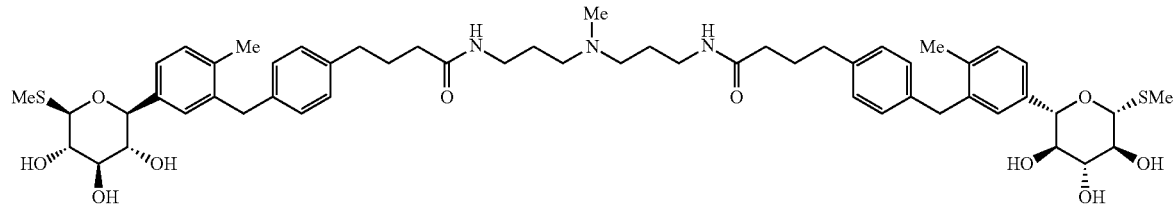

14

The same procedure was employed as for amide 11, using N1-(3-aminopropyl)-N1-methylpropane-1,3-diamine (0.5 equivalents), to provide the product 14 as the formate salt. $^1$H NMR (400 MHz, MeOH-d$_4$) δ ppm 8.50 (s, 1H), 7.15 (q, J=7.8 Hz, 6H), 7.02-7.09 (m, 8H), 4.38 (d, J=9.6 Hz, 2H), 4.12 (d, J=9.1 Hz, 2H), 3.94 (s, 4H), 3.34-3.51 (m, 6H), 3.21 (t, J=6.6 Hz, 4H), 2.86 (t, J=7.3 Hz, 4H), 2.63 (s, 3H), 2.57 (t, J=7.6 Hz, 4H), 2.18 (t, J=7.6 Hz, 4H), 2.20 (s, 6H), 2.14 (s, 6H), 1.88 (quin, J=7.6 Hz, 4H), 1.82 (quin, J=7.3 Hz, 4H). MS (ES+) [M+H]$^+$=1002.

6.6. Preparation of (2S,3S,4R,5S,6R)-2-(3-(4-(5-aminopentyl)benzyl)-4-methylphenyl)-6-(methyl-thio)tetrahydro-2H-pyran-3,4,5-triyl triacetate (16)

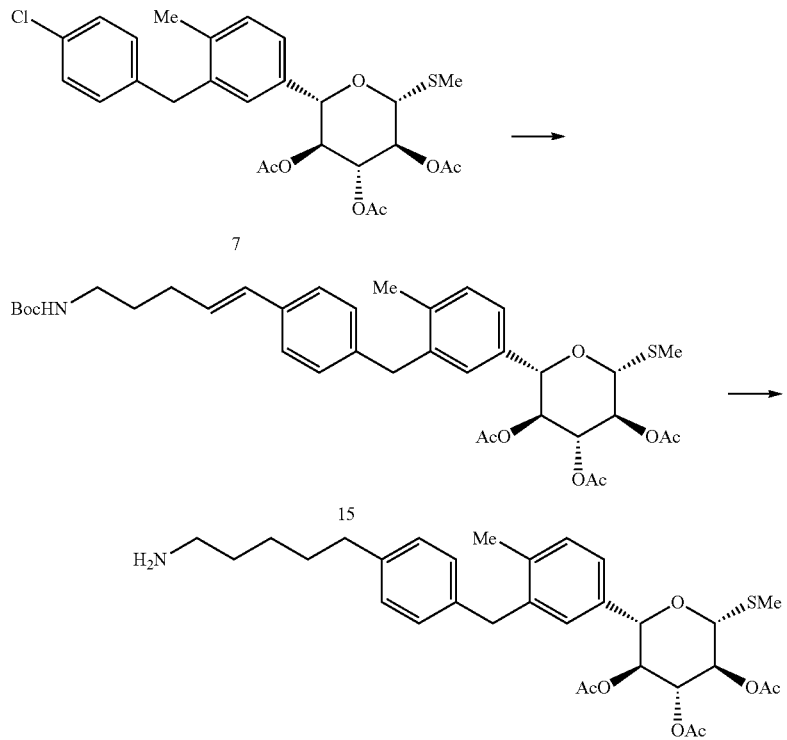

A microwave vial was charged with (2S,3S,4R,5S,6R)-2-(3-(4-chlorobenzyl)-4-methylphenyl)-6-(methylthio)tetra-hydro-2H-pyran-3,4,5-triyltriacetate (7, 520 mg, 1.0 mmol), tert-butyl pent-4-en-1-ylcarbamate (555 mg, 3.0 mmol.), Pd$_2$dba$_3$ (183 mg, 0.20 mmol), tri(tert-butyl)phosphonium tetrafluoroborate (232 mg, 0.80 mmol), dicyclohexylmethylamine (0.64 mL, 3.0 mmol), and N-methylpyrrolidinone (15 mL). The reaction was heated in the microwave at 160° C. for 20 min. The reaction was filtered over Celite with excess EtOAc. The organic layer was washed with H$_2$O, saturated aqueous NaHSO$_4$, and brine. It was dried with MgSO$_4$ and concentrated in vacuo. Silica gel flash chromatography (gradient 10-50% EtOAc/hexanes) provided Heck adduct 15 as a light yellow solid (360 mg, 54% yield).

The Heck product (15, 360 mg, 0.63 mmol) was dissolved in 10 mL of MeOH. Pd/C (10% wet, 100 mg) was added and the reaction was hydrogenated at 50 psi for 4 hours. Upon complete conversion, the reaction was filtered over Celite to remove the catalyst and the solvent was removed in vacuo. The crude residue was taken up in 4 mL of CH$_2$Cl$_2$ and 2 mL of TFA was added. After stirring for 3 hours at room temperature, the reaction was quenched with saturated aqueous NaHCO$_3$ and extracted three times with EtOAc. The combined organic extracts were washed with brine, dried over MgSO$_4$, filtered and concentrated under vacuum to provide the title compound 16 (260 mg, 85% yield) $^1$H NMR (400 MHz, DMSO-d$_6$) δ ppm 7.49 (br. s., 1H), 6.94-7.22 (m, 2H), 5.37 (t, J=9.6 Hz, 2H), 5.12 (t, J=9.6 Hz, 1H), 5.07 (t, J=9.6 Hz, 1H), 4.90 (d, J=9.6 Hz, 1H), 4.66 (d, J=9.6 Hz, 1H), 3.81-3.99 (m, 2H), 2.62-2.80 (m, 4H), 2.18 (s, 3H), 2.10 (s, 3H), 2.05 (s, 3H), 1.95 (s, 3H), 1.71 (s, 3H), 1.48-1.61 (m, 4H), 1.28-1.34 (m, 2H). MS (ES+) [M+H]$^+$= 572.

6.7. Preparation of (2S,3R,4R,5S,6R)-2-(3-(4-(5-(bis((S)-2,3-dihydroxypropyl)amino)pentyl)benzyl)-4-methylphenyl)-6-(methylthio)tetrahydro-2H-pyran-3,4,5-triol (17)

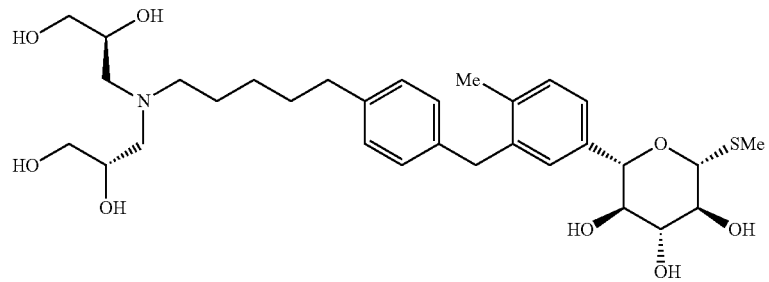

17

(2S,3S,4R,5S,6R)-2-(3-(4-(5-aminopentyl)benzyl)-4-methylphenyl)-6-(methylthio)tetrahydro-2H-pyran-3,4,5-triyltriacetate (16, 75 mg, 0.13 mmol) and (R)-2,2-dimethyl-1,3-dioxolane-4-carbaldehyde (26 mg, 0.20 mmol) were dissolved in 1 mL of dichloroethane. Sodium triacetoxyborohydride (55 mg, 0.26 mmol) was added and the reaction was stirred at room temperature overnight. The reaction was quenched with saturated aqueous NaHCO$_3$ and the aqueous phase was extracted three times with EtOAc. The combined organic layers were washed with brine, dried over MgSO$_4$, filtered, and the solvent removed in vacuo.

The crude residue was taken up in 1 mL H$_2$O and 1 mL MeOH. Lithium hydroxide (26 mg, 1.1 mmol) was added. 1 mL of THF was added to aid in solubility of the starting material. After 16 hours, the reaction was diluted with H$_2$O and extracted three times with EtOAc. The combined organic layers were washed with brine, dried over MgSO$_4$, filtered, and the solvent removed in vacuo.

The crude product was dissolved in 1 mL of MeOH. TFA (1 mL) was added and the reaction was stirred for 2 hours, upon which time, negligible reaction occurred. H$_2$O (0.5 mL) was added and the reaction was stirred at room temperature overnight. The solvents were removed in vacuo. The residue was purified by preparative HPLC (C18 30×100 mm column, 5-100% CH$_3$CN/10 mM aqueous ammonium formate, 45 mL/min) to provide the title compound 17 as the bisformate salt after lyophilization. $^1$H NMR (400 MHz, MeOH-d$_4$) δ ppm 8.50 (s, 2H), 6.98-7.21 (m, 7H), 4.39 (d, J=9.3 Hz, 1H), 4.12 (d, J=9.1 Hz, 1H), 3.87-4.01 (m, 2H), 3.95 (s, 2H), 3.47-3.62 (m, 4H), 3.36-3.47 (m, 3H), 3.02-3.25 (m, 4H), 3.20 (td, J=13.6, 3.0 Hz, 2H), 2.60 (t, J=7.5 Hz, 2H), 2.21 (s, 3H), 2.14 (s, 3H), 1.59-1.79 (m, 2H), 1.67 (quin, J=7.6 Hz, 2H), 1.39 (sxt, J=7.1 Hz, 2H). MS (ES+) [M+H]$^+$=594.

6.8. Preparation of 2-methyl-2-(3-(5-(4-(2-methyl-5-((2S,3R,4R,5S,6R)-3,4,5-trihydroxy-6-(methylthio)tetrahydro-2H-pyran-2-yl)benzyl)phenyl)pentyl)ureido)propanamide (18)

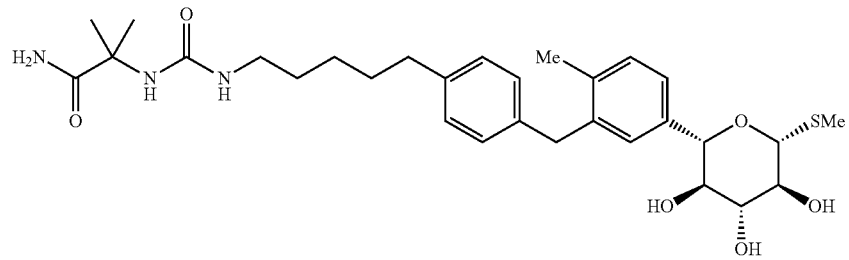

18

To a solution of (2S,3S,4R,5S,6R)-2-(3-(4-(5-aminopentyl)benzyl)-4-methylphenyl)-6-(methylthio)tetrahydro-2H-pyran-3,4,5-triyltriacetate (16, 100 mg, 0.18 mmol) and 4-nitrophenyl chloroformate (43 mg, 0.22 mmol) in CH$_2$Cl$_2$ (4 mL) was added triethylamine (35 μL, 0.25 mmol). The reaction was stirred for 4 hours, and then 2-amino-2-methylpropanamide hydrochloride (17 mg, 0.25 mmol) and DIPEA (23 μL, 0.27 mmol) was added. The reaction was stirred for 90 min., then diluted with EtOAc, washed with saturated aqueous NaHCO₃ and brine (with back extraction), dried over MgSO₄, filtered, and concentrated under vacuum.

This material was treated with NaOMe (50 µL, 25 wt % in MeOH, 0.22 mmol) in MeOH (2 mL) for 2 hours. The reaction was concentrated under vacuum, and the residue was purified by prep HPLC (C18 30×100 mm column, 10-70% CH₃CN/10 mM aqueous ammonium formate, 45 mL/min) to give 10 mg of the title compound 18 as a white solid after lyophilization. ¹H NMR (400 MHz, MeOH-d₄) δ ppm 7.00-7.20 (m, 7H), 4.39 (d, J=9.6 Hz, 1H), 4.12 (d, J=9.1 Hz, 1H), 3.95 (s, 2H), 3.34-3.50 (m, 3H), 3.06 (t, J=6.9 Hz, 2H), 2.57 (t, J=7.6 Hz, 2H), 2.21 (s, 3H), 2.14 (s, 3H), 1.53-1.67 (m, 2H), 1.48 (quin, J=7.3 Hz, 2H), 1.43 (s, 3H), 1.42 (s, 3H), 1.34 (spt, J=7.3 Hz, 1H). MS (ES+) [M+H]⁺=574.

6.9. Preparation of 1-(4-(4-(2-methyl-5-((2S,3R,4R,5S,6R)-3,4,5-trihydroxy-6-(methylthio)tetrahydro-2H-pyran-2-yl)benzyl)phenyl)butyl)guanidine (20)

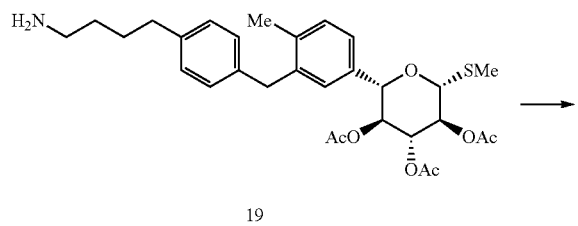

19

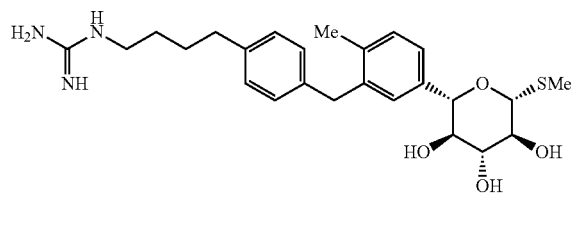

20

Preparation of (2S,3S,4R,5S,6R)-2-(3-(4-(4-aminobutyl)benzyl)-4-methylphenyl)-6-(methylthio)tetrahydro-2H-pyran-3,4,5-triyl triacetate (19)

The same procedure was employed as used for the synthesis of (2S,3S,4R,5S,6R)-2-(3-(4-(5-aminopentyl)benzyl)-4-methylphenyl)-6-(methylthio)tetrahydro-2H-pyran-3,4,5-triyltriacetate (16), using tert-butyl but-3-en-1-ylcarbamate as the reagent for the Heck reaction.

Preparation of 1-(4-(4-(2-methyl-5-((2S,3R,4R,5S,6R)-3,4,5-trihydroxy-6-(methylthio)tetrahydro-2H-pyran-2-yl)benzyl)phenyl)butyl)guanidine (20)

To a solution of (2S,3S,4R,5S,6R)-2-(3-(4-(4-aminobutyl)benzyl)-4-methylphenyl)-6-(methylthio)tetrahydro-2H-pyran-3,4,5-triyltriacetate (19, 50 mg, 0.090 mmol) and 3,5-dimethyl-1H-pyrazole-1-carboximidamide nitrate (66 mg, 0.33 mmol) in CH₃CN was added DIPEA (62 µL, 0.35 mmol). The reaction was heated at 70° C. for 2 hours, then cooled to room temperature and concentrated under vacuum. The residue was dissolved in MeOH and treated with a few drops of NaOMe (25 wt % in MeOH) for 1 hour. The reaction was concentrated under vacuum, and the residue was purified by prep HPLC (C18 30×100 mm column, 5-40% CH₃CN/10 mM aqueous ammonium formate, 45 mL/min) to give the title compound 20 as the formate salt (22 mg, 43% yield). ¹H NMR (400 MHz, MeOH-d₄) δ ppm 8.55 (s, 1H), 7.00-7.24 (m, 7H), 4.39 (d, J=9.6 Hz, 1H), 4.12 (d, J=9.1 Hz, 1H), 3.92-4.02 (m, 2H), 3.34-3.51 (m, 3H), 3.17 (t, J=6.8 Hz, 2H), 2.62 (t, J=7.3 Hz, 2H), 2.21 (s, 3H), 2.14 (s, 3H), 1.63-1.73 (m, 2H), 1.59 (s, 2H). MS (ES+) [M+H]⁺=474.

6.10. Preparation of 3-hydroxy-2,2-dimethyl-N-(4-(4-(2-methyl-5-((2S,3R,4R,5S,6R)-3,4,5-trihydroxy-6-(methylthio)tetrahydro-2H-pyran-2-yl)benzyl)phenyl)butyl)propanamide (21)

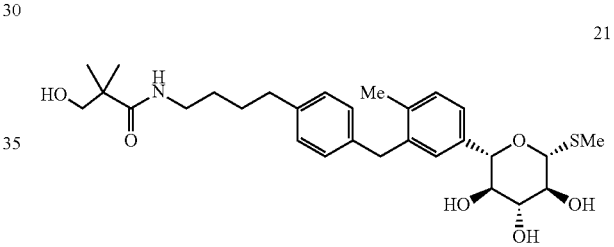

21

To a solution of (2S,3S,4R,5S,6R)-2-(3-(4-(4-aminobutyl)benzyl)-4-methylphenyl)-6-(methylthio)tetrahydro-2H-pyran-3,4,5-triyl triacetate (19, 55 mg, 0.10 mmol), 3-hydroxy-2,2-dimethylpropanoic acid (18 mg, 0.15 mmol), HATU (57 mg, 0.15 mmol), and DIPEA (52 µL, 0.30 mmol) were combined in DMF (1 mL) and stirred for 4 hours at room temperature. The reaction quenched with saturated aqueous NaHCO₃ and extracted twice with EtOAc. The combined organic layers were washed with brine, dried with MgSO₄, filtered, and concentrated under vacuum. The residue was dissolved in MeOH and treated with a few drops of NaOMe (25 wt % in MeOH) for 1 hour. The reaction was concentrated under vacuum, and the residue was purified by prep HPLC (C18 30×100 mm column, 5-40% CH₃CN/10 mM aqueous ammonium formate, 45 mL/min) to give the title compound 21 as a white solid (22 mg, 41% yield). ¹H NMR (400 MHz, MeOH-d₄) δ ppm 6.98-7.22 (m, 7H), 4.39 (d, J=9.6 Hz, 1H), 4.13 (d, J=9.1 Hz, 1H), 3.90-3.99 (m, 2H), 3.49 (s, 2H), 3.35-3.46 (m, 3H), 3.19 (t, J=6.9 Hz, 2H), 2.58 (t, J=7.5 Hz, 2H), 2.18-2.23 (m, 3H), 2.14 (s, 3H), 1.60 (s, 2H), 1.46-1.57 (m, 2H), 1.11 (s, 6H). MS (ES+) [M+H]⁺=532.

6.11. Preparation of (2S,3R,4R,5S,6R)-2-(3-(4-(4-((1-hydroxy-2-methylpropan-2-yl)amino)butyl)benzyl)-4-methylphenyl)-6-(methylthio)tetrahydro-2H-pyran-3,4,5-triol (24)

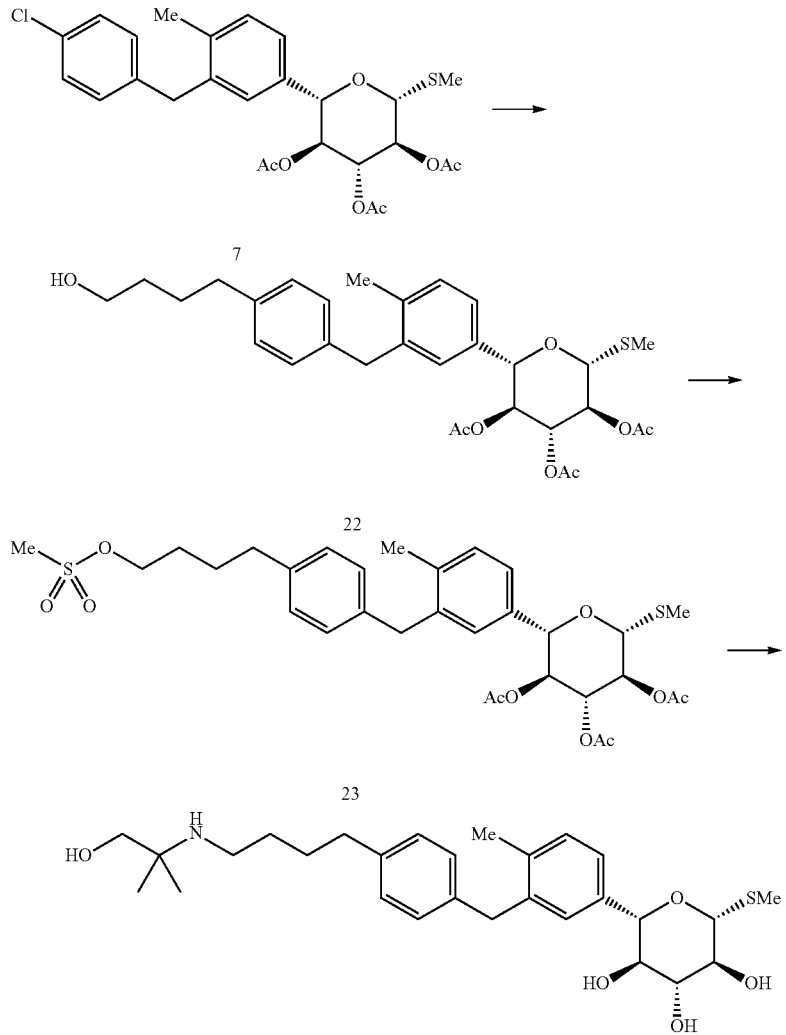

Preparation of (2S,3S,4R,5S,6R)-2-(3-(4-(4-hydroxybutyl)benzyl)-4-methylphenyl)-6-(methylthio)tetrahydro-2H-pyran-3,4,5-triyltriacetate (22)

A 20 mL microwave vial was charged with (2S,3S,4R,5S,6R)-2-(3-(4-chlorobenzyl)-4-methylphenyl)-6-(methylthio)tetrahydro-2H-pyran-3,4,5-triyltriacetate (7, 520 mg, 1.0 mmol), 3-butenol (0.26 mL, 3.0 mmol), $Pd_2dba_3$ (183 mg, 0.20 mmol), tri(tert-butyl)phosphonium tetrafluoroborate (232 mg, 0.80 mmol), dicyclohexylmethylamine (0.64 mL, 3.0 mmol), and 10 mL of N-methylpyrrolidinone. The reaction was heated in the microwave at 160° C. for 20 min. The reaction was filtered over Celite with excess EtOAc. The organic layer was washed with $H_2O$, saturated aqueous $NaHSO_4$, and brine. It was dried with $MgSO_4$ and concentrated in vacuo. Flash chromatography (gradient 10-80% EtOAc/hexanes) provided the Heck adduct (257 mg). This purified product was dissolved in 5 mL of a 1:1 (v:v) mixture of MeOH/THF. Pd/C (10% wet, 26 mg) was added and subjected to 40 psi hydrogen pressure for 5 hours. The reaction was filtered over Celite with excess MeOH and concentrated in vacuo to provide the title compound 22 (247 mg, 44% yield). $^1$H NMR (400 MHz, CHLOROFORM-d) δ ppm 7.11-7.18 (m, 2H), 7.09 (d, J=8.1 Hz, 2H), 6.95-7.06 (m, 3H), 5.33 (dd, J=9.6 Hz, 1H), 5.20 (dd, J=9.6 Hz, 1H), 5.10 (dd, J=9.7 Hz, 1H), 4.52 (d, J=9.9 Hz, 1H), 4.38 (d, J=9.9 Hz, 1H), 3.93 (d, J=4.5 Hz, 2H), 3.66 (t, J=5.9 Hz, 2H), 2.61 (t, J=7.3 Hz, 2H), 2.22 (s, 3H), 2.17 (s, 3H), 2.10 (s, 3H), 2.01 (s, 3H), 1.74 (s, 3H), 1.64-1.73 (m, 2H), 1.56-1.64 (m, 2H). MS (ES+) $[M+NH_4]^+$=576.

Preparation of (2S,3S,4R,5S,6R)-2-(4-methyl-3-(4-(4-((methylsulfonyl)oxy)butyl)-benzyl)phenyl)-6-(methylthio)tetrahydro-2H-pyran-3,4,5-triyltriacetate (23)

Methanesulfonyl chloride (41 μL, 0.53 mmol) and triethylamine (80 μL, 0.58 mmol) were added to a solution of (2S,3S,4R,5S,6R)-2-(3-(4-(4-hydroxybutyl)benzyl)-4-methylphenyl)-6-(methylthio)tetrahydro-2H-pyran-3,4,5- triyl triacetate (22, 247 mg, 0.44 mmol) in 5 mL CH$_2$Cl$_2$ and stirred at room temperature for 2 hours. The reaction was quenched with 1N aqueous HCl. The aqueous layer was extracted two times with EtOAc. The combined organic layers were washed with H$_2$O and brine, dried with MgSO$_4$, filtered, and concentrated in vacuo to provide the product 23 (279 mg, 99% yield), which was used in the next step without further purification. $^1$H NMR (400 MHz, CHLOROFORM-d) δ ppm 7.14 (s, 2H), 7.02-7.11 (m, 3H), 7.00 (d, J=7.8 Hz, 2H), 5.33 (dd, J=9.6 Hz, 1H), 5.21 (dd, J=9.6 Hz, 1H), 5.12 (dd, J=9.6 Hz, 1H), 4.48-4.56 (m, 1H), 4.39 (d, J=9.9 Hz, 1H), 4.24 (t, J=6.1 Hz, 1H), 3.93 (d, J=3.8 Hz, 2H), 2.99 (s, 3H), 2.62 (t, J=7.2 Hz, 2H), 2.22 (s, 3H), 2.15-2.20 (m, 3H), 2.10 (s, 3H), 2.01 (s, 3H), 1.70-1.81 (m, 4H). MS (ES+) [M+NH$_4$]$^+$=654.

Preparation of (2S,3R,4R,5S,6R)-2-(3-(4-(4-((1-hydroxy-2-methylpropan-2-yl)amino)butyl)benzyl)-4-methylphenyl)-6-(methylthio)tetrahydro-2H-pyran-3,4,5-triol (24)

2-Amino-2-methylpropan-1-ol (23 mg, 0.25 mmol), catalytic sodium iodide, and (2S,3S,4R,5S,6R)-2-(4-methyl-3-(4-(4-((methylsulfonyl)oxy)butyl)benzyl)phenyl)-6-(methylthio)tetrahydro-2H-pyran-3,4,5-triyl triacetate (65 mg, 0.10 mmol) were heated to 80° C. in 0.5 mL of isopropanol/CH$_3$CN (1:1 v:v) for 64 hours. The reaction was cooled to room temperature, diluted with 2 mL of MeOH, and NaOMe (25 wt % in MeOH, 0.5 mL) was added. Acetate deprotection was complete within 30 min. Volatiles were removed in vacuo and the crude residue was purified by prep HPLC (C18 30×100 mm column, 5-100% CH$_3$CN/10 mM aqueous ammonium formate, 45 mL/min) to provide the product as the bisformate salt (17 mg, 34% yield) after lyophilization. $^1$H NMR (400 MHz, MeOH-d$_4$) δ ppm 8.53 (s, 2H), 7.01-7.25 (m, 7H), 4.39 (d, J=9.6 Hz, 1H), 4.13 (d, J=9.1 Hz, 1H), 3.90-4.02 (m, 2H), 3.50 (s, 2H), 3.35-3.48 (m, 3H), 2.87-2.97 (m, 2H), 2.65 (t, J=6.9 Hz, 2H), 2.20 (s, 3H), 2.15 (s, 3H), 1.59-1.78 (m, 4H), 1.27 (s, 6H). MS (ES+) [M+H]$^+$=504.

6.12. Preparation of (2S,3R,4R,5S,6R)-2-(3-(4-(4-((1,3-dihydroxy-2-(hydroxymethyl)propan-2-yl)amino)butyl)benzyl)-4-methylphenyl)-6-(methylthio)tetrahydro-2H-pyran-3,4,5-triol (25)

25

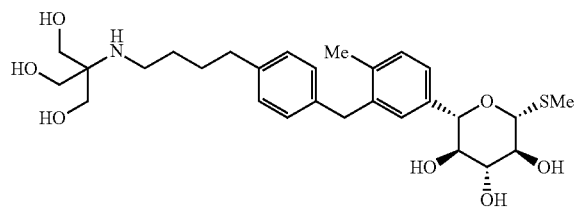

The same procedure was employed as for amine 24, using 2-amino-2-(hydroxyl-methyl)propane-1,3-diol, to provide the product 25 as the bisformate salt. $^1$H NMR (400 MHz, MeOH-d$_4$) δ ppm 8.53 (s, 2H), 6.98-7.23 (m, 7H), 4.39 (d, J=9.3 Hz, 1H), 4.13 (d, J=9.1 Hz, 1H), 3.94-4.03 (m, 2H), 3.69 (s, 6H), 3.34-3.50 (m, 3H), 3.03-3.13 (m, 2H), 2.58-2.69 (m, 2H), 2.20 (s, 3H), 2.12-2.18 (m, 3H), 1.70 (m, 4H). [M+H]$^+$=537.

6.13. Preparation of 1-((4-(4-(2-methyl-5-((2S,3R,4R,5S,6R)-3,4,5-trihydroxy-6-(methylthio)tetrahydro-2H-pyran-2-yl)benzyl)phenyl)butyl)amino)cyclopentanecarboxamide (26)

26

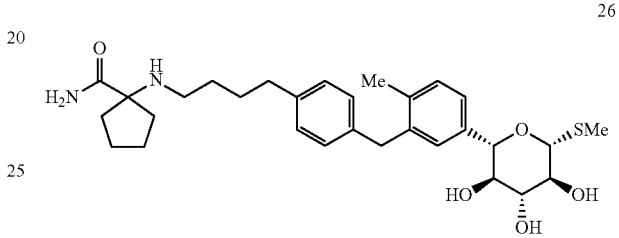

The same procedure was employed as for amine 24, using 1-aminocyclopentanecarboxamide, to provide the product 26 with 0.5 equivalents of formic acid. $^1$H NMR (400 MHz, MeOH-d$_4$) δ ppm 8.52 (s, 0.5H, formate), 6.98-7.22 (m, 7H), 4.39 (d, J=9.6 Hz, 1H), 4.13 (d, J=9.3 Hz, 1H), 3.91-4.01 (m, 2H), 3.34-3.51 (m, 3H), 2.50-2.68 (m, 4H), 2.21 (s, 3H), 2.14 (s, 3H), 2.10 (d, J=7.3 Hz, 2H), 1.73-1.87 (m, 6H), 1.63-1.72 (m, 2H), 1.58 (d, J=7.1 Hz, 2H). MS (ES+) [M+H]$^+$=543.

6.14. Preparation of 1-((4-(4-(2-methyl-5-((2S,3R,4R,5S,6R)-3,4,5-trihydroxy-6-(methylthio)tetrahydro-2H-pyran-2-yl)benzyl)phenyl)butyl)amino)cyclopentanecarboxamide (27)

27

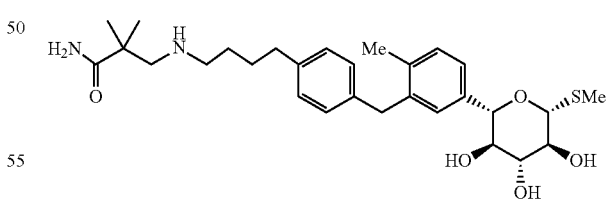

The same procedure was employed as for amine 24, using 3-amino-2,2-dimethylpropanamide, to provide the product 27 with 1.5 equivalents of formic acid. $^1$H NMR (400 MHz, MeOH-d$_4$) δ ppm 8.52 (s, 1.5H, formate), 7.00-7.22 (m, 7H), 4.39 (d, J=9.3 Hz, 1H), 4.13 (d, J=9.3 Hz, 1H), 3.96 (s, 2H), 3.35-3.52 (m, 3H), 2.95-3.06 (m, 4H), 2.65 (t, J=6.4 Hz, 2H), 2.21 (s, 3H), 2.14 (s, 3H), 1.64-1.78 (m, 4H), 1.30 (s, 6H). MS (ES+) [M+H]$^+$=531.

6.15. Preparation of Tetrazole Derivatives (30 and 31)

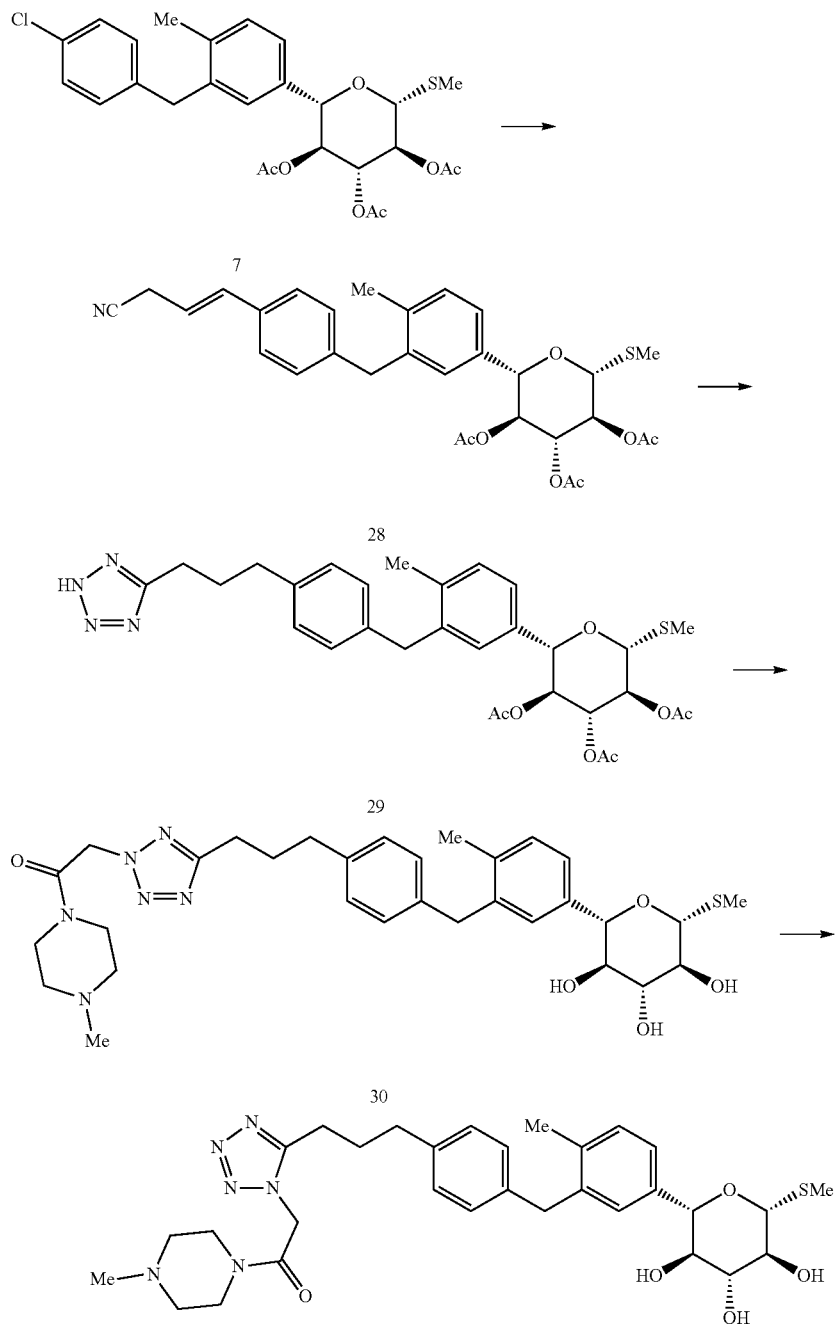

Preparation of (2S,3S,4R,5S,6R)-2-(3-(4-((E)-3-cyanoprop-1-en-1-yl)benzyl)-4-methylphenyl)-6-(methylthio)tetrahydro-2H-pyran-3,4,5-triyltriacetate (28)

A 5 mL microwave vial was charged with (2S,3S,4R,5S,6R)-2-(3-(4-chlorobenzyl)-4-methylphenyl)-6-(methylthio)tetrahydro-2H-pyran-3,4,5-triyltriacetate (7, 208 mg, 0.40 mmol), but-3-enenitrile (0.10 mL, 1.2 mmol), Pd₂dba₃ (37 mg, 0.040 mmol), tri(tert-butyl)phosphonium tetrafluoroborate (46 mg, 0.16 mmol), dicyclohexylmethylamine (0.25 mL, 1.2 mmol), and 2 mL of N-methylpyrrolidinone. The reaction was heated in the microwave at 160° C. for 20 min. The reaction was filtered over Celite with excess EtOAc. The organic layer was washed with H₂O, saturated aqueous NaHSO₄, and brine. It was dried with MgSO₄ and concentrated in vacuo. Flash chromatography (gradient 10-80% EtOAc/hexanes) provided the Heck adduct 28 (140 mg, 64% yield). ¹H NMR (400 MHz, CHLOROFORM-d) δ ppm 7.24-7.31 (m, 2H), 7.11-7.20 (m, 2H), 7.02-7.09 (m, 3H), 6.70 (dt, J=15.9, 1.6 Hz, 1H), 6.01 (dt, J=15.8, 5.7 Hz, 1H), 5.33 (t, J=9.3 Hz, 1H), 5.21 (t, J=9.7 Hz, 1H), 5.12 (t, J=9.6 Hz, 1H), 4.52 (d, J=9.9 Hz, 1H), 4.39 (d, J=9.9 Hz, 1H), 3.95 (d, J=3.5 Hz, 2H), 3.28 (dd, J=5.8, 1.8 Hz, 2H), 2.20 (s, 3H), 2.16 (s, 3H), 2.09 (s, 3H), 2.01 (s, 3H), 1.75 (s, 3H). MS (ES+) [M+NH$_4$]$^+$=567.

Preparation of (2S,3S,4R,5S,6R)-2-(3-(4-(3-(2H-tetrazol-5-yl)propyl)benzyl)-4-methylphenyl)-6-(methylthio)tetrahydro-2H-pyran-3,4,5-triyl triacetate (29)

(2S,3S,4R,5S,6R)-2-(3-(4-((E)-3-cyanoprop-1-en-1-yl)benzyl)-4-methylphenyl)-6-(methylthio)tetrahydro-2H-pyran-3,4,5-triyl triacetate (28, 140 mg, 0.25 mmol) was dissolved in 6 mL MeOH. Pd/C (10% wet, 14 mg) was added and subjected to 40 psi hydrogen pressure for 5 hours. The reaction was filtered over Celite with excess MeOH and concentrated in vacuo. The crude product was used without further purification (120 mg, 87% yield). MS (ES+) [M+NH$_4$]$^+$=569.

60 mg of this hydrogenated product (0.108 mmol) was taken up in toluene (1.1 mL, 0.1 M). Trimethylsilylazide (43 μL, 0.324 mmol) and dibutyltin oxide (8 mg, 0.0324 mmol) were added. The reaction was headed to 90° C. for 18 hrs. The reaction was cooled to room temperature and quenched with H$_2$O. The aqueous layer was extracted twice with EtOAc. The combined organic layers were washed with brine, dried over Na$_2$SO$_4$, and concentrated in vacuo. Silica gel flash chromatography (gradient 5-80% EtOAc/hexanes then 10% MeOH/CH$_2$Cl$_2$) provided tetrazole 29 (32 mg, 50% yield). MS (ES+) [M+NH$_4$]$^+$=597.

Preparation of 2-(5-(3-(4-(2-methyl-5-((2S,3R,4R,5S,6R)-3,4,5-trihydroxy-6-(methylthio)tetrahydro-2H-pyran-2-yl)benzyl)phenyl)propyl)-2H-tetrazol-2-yl)-1-(4-methylpiperazin-1-yl)ethanone (30) and 2-(5-(3-(4-(2-methyl-5-((2S,3R,4R,5S,6R)-3,4,5-trihydroxy-6-(methylthio)tetrahydro-2H-pyran-2-yl)benzyl)phenyl)propyl)-1H-tetrazol-1-yl)-1-(4-methylpiperazin-1-yl)ethanone (31)

(2S,3S,4R,5S,6R)-2-(3-(4-(3-(2H-tetrazol-5-yl)propyl)benzyl)-4-methylphenyl)-6-(methylthio)tetrahydro-2H-pyran-3,4,5-triyl triacetate (29, 32 mg, 0.0537 mmol) was combined with 2-chloro-1-(4-methylpiperazin-1-yl)ethanone (14 mg, 0.0644 mmol) and triethylamine (22 μL, 0.161 mmol) in 0.5 mL of CH$_3$CN. The reaction was stirred at 60° C. for 18 hrs, providing a mixture of two regioisomers. The reaction was diluted with H$_2$O, filtered, and purified by prep HPLC (C18 30×100 mm column, 5-100% CH$_3$CN/10 mM aqueous ammonium formate, 45 mL/min). The regioisomers were separated cleanly. The respective product residues were treated with sodium methoxide (0.10 mL, 25 wt % in MeOH) in MeOH (2 mL) under nitrogen for 30 min. The reaction was concentrated under vacuum, and the reactions was purified by prep HPLC (C18 30×100 mm column, 5-100% CH$_3$CN/10 mM aqueous ammonium formate, 45 mL/min) and lyophilized to give alkylated tetrazole regioisomers 30 and 31 (4.3 mg and 3.1 mg, respectively, as the bisformate salts). Regiochemistry was confirmed by NOESY correlations.

1,2-Disubstituted tetrazole 30: $^1$H NMR (400 MHz, MeOH-d$_4$) δ ppm 8.39 (s, 2H, formate), 7.01-7.21 (m, 8H), 5.45 (s, 2H), 4.39 (d, J=9.6 Hz, 1H), 4.13 (d, J=9.1 Hz, 1H), 3.97 (s, 2H), 3.60 (q, J=4.8 Hz, 4H), 3.33-3.50 (m, 3H), 2.79 (t, J=7.5 Hz, 2H), 2.68 (t, J=7.5 Hz, 2H), 2.62 (t, J=5.1 Hz, 2H), 2.53 (t, J=5.1 Hz, 2H), 2.41 (s, 3H), 2.21 (s, 3H), 2.14 (s, 3H), 2.09 (quin, J=7.6 Hz, 2H). MS (ES+) [M+H]$^+$=611.

1,3-Disubstituted tetrazole 31: $^1$H NMR (400 MHz, MeOH-d$_4$) δ ppm 8.38 (s, 2H), 6.99-7.20 (m, 7H), 5.74 (s, 2H), 4.38 (d, J=9.3 Hz, 1H), 4.12 (d, J=9.1 Hz, 1H), 3.96 (s, 2H), 3.65 (t, J=5.3 Hz, 4H), 3.33-3.49 (m, 3H), 2.88 (t, J=7.5 Hz, 2H), 2.60-2.69 (m, 4H), 2.57 (t, J=5.1 Hz, 2H), 2.41 (s, 3H), 2.21 (s, 3H), 2.10-2.14 (m, 3H), 2.07 (quin, J=7.3 Hz, 2H). MS (ES+) [M+H]$^+$=611.

6.16. Preparation of (2S,3S,4R,5S,6R)-2-(3-(4-hydroxybenzyl)-4-methylphenyl)-6-(methylthio)tetrahydro-2H-pyran-3,4,5-triyl triacetate (37)

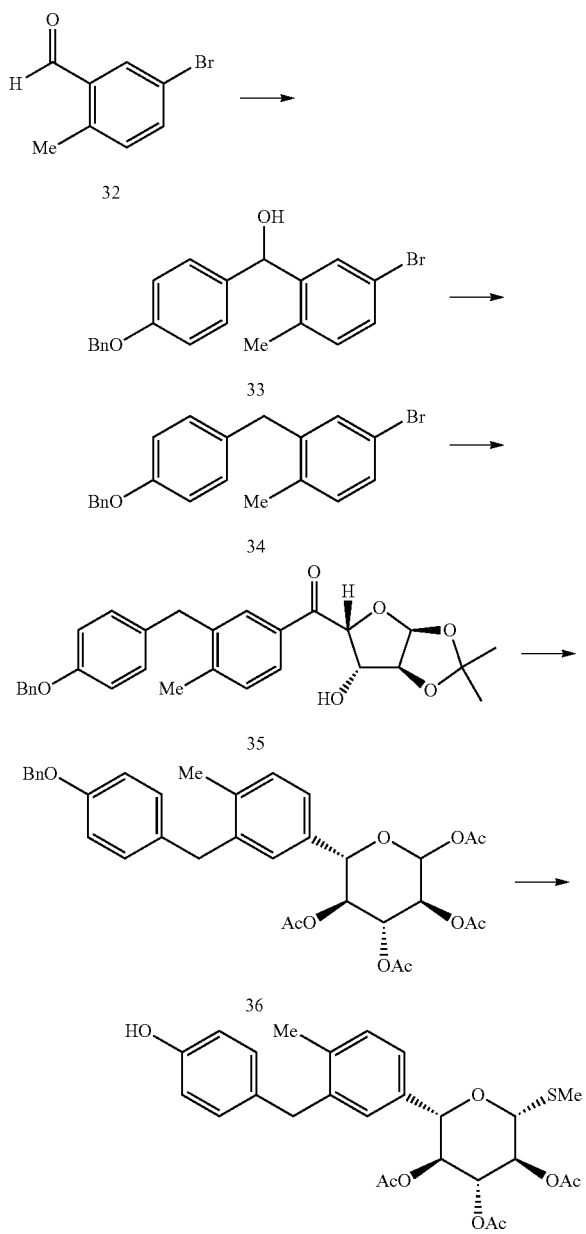

Preparation of (4-(benzyloxy)phenyl)(5-bromo-2-methylphenyl)methanol (33)

To a solution of 4-benzyloxybromobenzene (2.63 g, 10 mmol) in THF (50 mL) at −78° C. under nitrogen was slowly added n-butyllithium (2.5 M in hexanes, 4.4 mL, 11 mmol). The reaction was stirred for 30 minutes. 5-Bromo-2-methylbenzaldehyde (32, 1.99 g, 10 mmol) in THF (4 mL plus 1 mL rinse) was added slowly. The reaction was allowed to slowly warm to about 0° C. over 2 hours, then quenched with saturated aqueous NH$_4$Cl, diluted with ether, washed with H$_2$O and brine, dried over MgSO$_4$, filtered, and concentrated under vacuum. The residue was purified by silica gel flash chromatography (gradient 0-25% EtOAc/hexanes) to give 3.12 g (82% yield) of the title compound 33 as a clear oil. $^1$H NMR (400 MHz, CHLOROFORM-d) δ ppm 7.80 (d, J=2.3 Hz, 1H), 7.36-7.47 (m, 4H), 7.29-7.36 (m, 2H), 7.18-7.24 (m, 2H), 6.99 (d, J=8.1 Hz, 1H), 6.88-6.97 (m, 2H), 5.89 (d, J=3.5 Hz, 1H), 5.06 (s, 2H), 2.12 (s, 3H), 2.06 (d, J=3.5 Hz, 1H); MS (ES+) [M−OH]$^+$=365, 367.

Preparation of (4-(benzyloxy)phenyl)(5-bromo-2-methylphenyl)methanol (34)

To a solution of (4-(benzyloxy)phenyl)(5-bromo-2-methylphenyl)methanol (33, 3.12 g, 8.2 mmol) and triethylsilane (1.6 mL, 9.8 mmol) in CH$_2$Cl$_2$ (40 mL) at 0° C. under nitrogen was slowly added BF$_3$OEt$_2$ (1.4 mL, 11.4 mmol). The reaction was stirred at room temperature overnight, after which it was quenched with saturated aqueous NaHCO$_3$ and stirred for 30 minutes. The reaction was diluted with ether, washed with additional saturated aqueous NaHCO$_3$ and brine (with back extraction), dried over MgSO$_4$, filtered, and concentrated under vacuum. The residue was purified by silica gel flash chromatography (gradient 0-10% EtOAc:hexanes) to give 2.71 g (91% yield) of the product 34 as a white solid. $^1$H NMR (400 MHz, CHLOROFORM-d) δ ppm 7.30-7.49 (m, 5H), 7.27 (dd, J=8.0, 2.1 Hz, 1H), 7.22 (d, J=2.0 Hz, 1H), 6.98-7.09 (m, 3H), 6.86-6.97 (m, 2H), 5.05 (s, 2H), 3.88 (s, 2H), 2.19 (s, 3H); MS (ES+) [M+NH$_4$]$^+$= 384, 386.

Preparation of (3-(4-(benzyloxy)benzyl)-4-methylphenyl)((3aS,5R,6S,6aS)-6-hydroxy-2,2-dimethyltetrahydrofuro[2,3-d][1,3]dioxol-5-yl)methanone (35)

To a solution of 2-(4-(benzyloxy)benzyl)-4-bromo-1-methylbenzene (34, 2.71 g, 7.4 mmol) in THF (37 mL) under nitrogen at −78° C. was slowly added n-butyllithium (3.3 mL of 2.5 M solution in hexanes, 8.1 mmol), and the reaction was stirred for 30 min. Meanwhile, to a solution of ((3aS,5R,6S,6aS)-6-hydroxy-2,2-dimethyltetrahydrofuro[2,3-d][1,3]dioxol-5-yl)(morpholino)methanone (2.02 g, 7.4 mmol) in THF (37 mL) under nitrogen at 0° C. was added tert-butylmagnesium chloride (8.1 mL of 1 M solution in THF, 8.1 mmol). The reaction was stirred for 20 min, then added slowly by cannula to the aryl lithium solution at −78° C. The reaction was allowed to gradually warm to room temperature over 3 hours, then quenched with saturated aqueous NH$_4$Cl, diluted with EtOAc, washed with H$_2$O and brine (with back extraction), dried over MgSO$_4$, filtered, and concentrated under vacuum. The residue was purified by silica gel flash chromatography (gradient 0-50% EtOAc/hexanes) to give 2.44 g (70% yield) of the product 35 as a white foam. $^1$H NMR (400 MHz, CHLOROFORM-d) δ ppm 7.86 (dd, J=7.8, 1.8 Hz, 1H), 7.75-7.80 (m, 1H), 7.27-7.49 (m, 6H), 7.04 (d, J=8.6 Hz, 2H), 6.86-6.96 (m, 2H), 6.09 (d, J=3.5 Hz, 1H), 5.32 (d, J=2.8 Hz, 1H), 5.04 (s, 2H), 4.60 (d, J=3.5 Hz, 1H), 4.53-4.58 (m, 1H), 3.98 (s, 2H), 3.03 (d, J=4.3 Hz, 1H), 2.31 (s, 3H), 1.56 (s, 3H), 1.36 (s, 3H); MS (ES+) [M+H]$^+$=475.

Preparation of (3S,4R,5S,6S)-6-(3-(4-(benzyloxy)benzyl)-4-methylphenyl)tetrahydro-2H-pyran-2,3,4,5-tetrayl tetraacetate (36)

To a solution of (3-(4-(benzyloxy)benzyl)-4-methylphenyl)((3aS,5R,6S,6aS)-6-hydroxy-2,2-dimethyltetrahydrofuro[2,3-d][1,3]dioxol-5-yl)methanone (35, 2.44 g, 5.1 mmol) and CeCl$_3$.7H$_2$O (2.30 g, 6.2 mmol) in MeOH at 0° C. was added slowly sodium borohydride (78 mg, 2.1 mmol in 1 mL 1 M aqueous NaOH). The reaction was stirred for 15 min at 0° C. and 15 min at room temperature, then quenched with saturated aqueous NH$_4$Cl. The reaction was partially concentrated under vacuum, diluted with EtOAc, washed with H$_2$O and twice with brine (with back extraction), dried over Na$_2$SO$_4$, and concentrated under vacuum to give 2.4 g of diol as a white solid.

This material was treated with 1:1 AcOH/H$_2$O (20 mL) at 100° C. under nitrogen for 22 hours. The reaction was cooled to room temperature, concentrated under vacuum, azeotroped twice with toluene, and placed under high vacuum. The residue, along with DMAP (61 mg, 0.5 mmol) was dissolved in CH$_2$Cl$_2$ (25 mL) under nitrogen at 0° C., and triethylamine (6.2 mL, 45 mmol) was added, followed by acetic anhydride (3.8 mL, 40 mmol). The reaction was stirred at room temperature for 18 hours, then quench with saturated aqueous NaHCO$_3$ (60 mL), stirred for 50 min, and extracted with twice with EtOAc. The combined organic extracts were washed with brine, dried over MgSO$_4$, filtered, and concentrated under vacuum. The residue was purified by silica gel flash chromatography (gradient 0-50% EtOAc/hexanes) to give 2.80 g (90% yield) of a 1:1 mixture of α:β anomers of the product 36 as a white foam. $^1$H NMR (400 MHz, CHLOROFORM-d) δ ppm 7.29-7.47 (m, 5H), 7.10-7.18 (m, 2H), 7.06 (s, 1H), 6.98 (d, J=8.6 Hz, 2H), 6.83-6.94 (m, 2H), 6.46 (d, J=3.5 Hz, 0.5H), 5.87 (d, J=8.3 Hz, 0.5H), 5.57 (t, J=10.1 Hz, 0.5H), 5.35 (t, J=9.6 Hz, 0.5H), 5.21-5.30 (m, 1H), 5.18 (t, J=9.6 Hz, 0.5H), 5.12 (t, J=9.9 Hz, 0.5H), 4.80 (d, J=10.1 Hz, 0.5H), 4.48 (d, J=9.9 Hz, 0.5H), 3.83-3.97 (m, 2H), 2.21 (s, 1.5H), 2.20 (s, 3H), 2.10 (s, 1.5H), 2.07 (s, 1.5H), 2.05 (s, 1.5H), 2.03 (s, 1.5H), 2.02 (s, 1.5H), 1.76 (s, 1.5H), 1.74 (s, 1.5H); MS (ES+) [M+NH$_4$]$^+$=622.

Preparation of (2S,3S,4R,5S,6R)-2-(3-(4-hydroxy-benzyl)-4-methylphenyl)-6-(methylthio)tetrahydro-2H-pyran-3,4,5-triyl triacetate (37)

(3S,4R,5S,6S)-6-(3-(4-(benzyloxy)benzyl)-4-methylphenyl)tetrahydro-2H-pyran-2,3,4,5-tetrayl tetraacetate (36, 5.29 g, 8.8 mmol) was hydrogenated over 10% Pd/C (50% wet) (0.93 g, 0.44 mmol) in THF (44 mL) under hydrogen at atmospheric pressure for 1 hour. The reaction was filtered through celite, concentrated under vacuum, azeotroped twice with toluene, and placed on the high vacuum to dry thoroughly. The resulting phenol was carried to the next step without further purification. It was combined with thiourea (2.01 g, 26 mmol) and dissolved in dioxane (44 mL). TMSOTf (4.8 mL, 26 mmol) was added. The reaction was heated at 80° C. for 3 hours and then cooled to room temperature. Methyl iodide (2.2 mL, 35 mmol) was added, followed by DIPEA (12 mL, 70 mmol). The reaction was stirred overnight, then quenched with saturated aqueous NaHSO$_4$ (150 mL), stirred vigorously for 2 hours, diluted with EtOAc, washed with H$_2$O and brine (with back extraction), dried over MgSO$_4$, filtered, and concentrated under vacuum. The residue was purified by silica gel chromatography (gradient 0-50% EtOAc/hexanes) to give 3.88 g (88% yield) of the product 37 as a white foam. $^1$H NMR (400 MHz, CHLOROFORM-d) δ ppm 7.10-7.19 (m, 2H), 7.03 (s, 1H), 6.94 (d, J=8.6 Hz, 2H), 6.68-6.77 (m, 2H), 5.33 (t, J=9.3 Hz, 1H), 5.21 (t, J=9.6 Hz, 1H), 5.12 (t, J=9.6 Hz, 1H), 4.59 (s, 1H), 4.52 (d, J=9.9 Hz, 1H), 4.38 (d, J=9.9 Hz, 1H), 3.82-3.96 (m, 2H), 2.21 (s, 3H), 2.18 (s, 3H), 2.10 (s, 3H), 2.01 (s, 3H), 1.75 (s, 3H); MS (ES+) [M+NH$_4$]$^+$=520.

6.17. Preparation of (2S,3S,4R,5S,6R)-2-(4-chloro-3-(4-hydroxybenzyl)phenyl)-6-(methylthio)tetrahydro-2H-pyran-3,4,5-triyl triacetate (38)

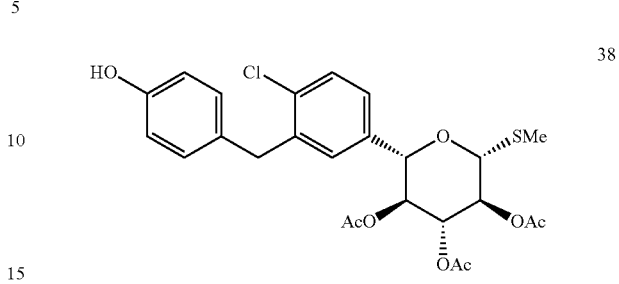

Phenol 38 was prepared in an analogous manner to (2S,3S,4R,5S,6R)-2-(3-(4-hydroxybenzyl)-4-methylphenyl)-6-(methylthio)tetrahydro-2H-pyran-3,4,5-triyltriacetate (37). $^1$H NMR (400 MHz, CHLOROFORM-d) δ ppm 7.36 (d, J=8.3 Hz, 1H), 7.18 (dd, J=8.3, 2.3 Hz, 1H), 7.07 (d, J=2.3 Hz, 1H), 7.03 (d, J=8.6 Hz, 2H), 6.73-6.78 (m, 2H), 5.32 (t, J=9.3 Hz, 1H), 5.19 (t, J=9.6 Hz, 1H), 5.04 (t, J=9.6 Hz, 1H), 4.77 (s, 1H), 4.51 (d, J=9.9 Hz, 1H), 4.37 (d, J=9.9 Hz, 1H), 3.95-4.07 (m, 2H), 2.16 (s, 3H), 2.09 (s, 3H), 2.01 (s, 3H), 1.73 (s, 3H); MS (ES+) [M+NH$_4$]$^+$=540.

6.18. Preparation of N-(2-methyl-1-(4-methylpiperazin-1-yl)-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide (40)

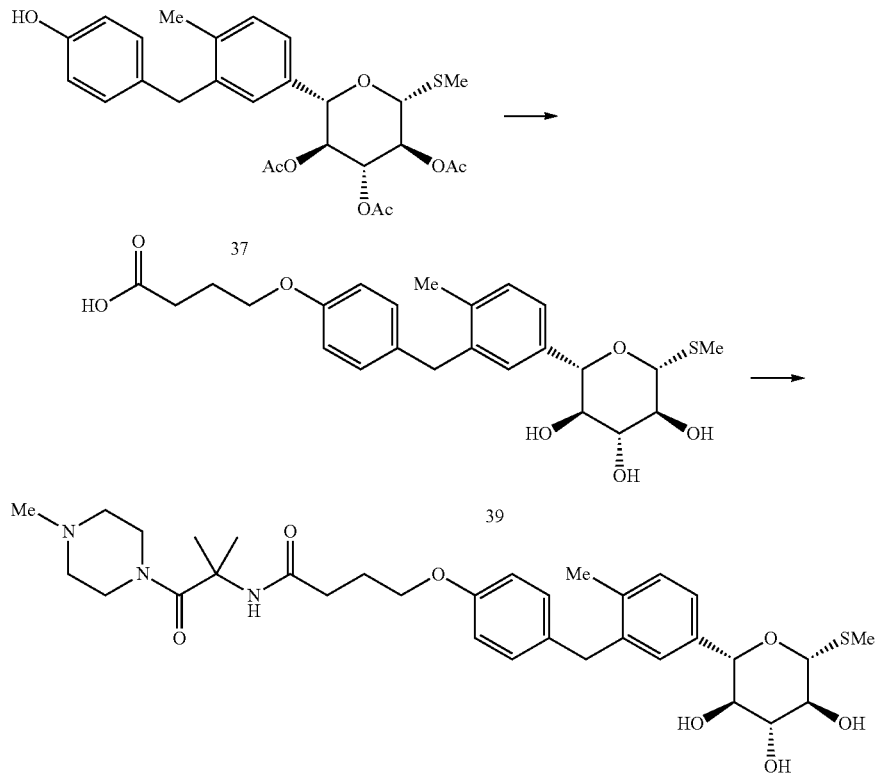

Preparation of 4-(4-(2-methyl-5-((2S,3R,4R,5S,6R)-3,4,5-trihydroxy-6-(methylthio)tetrahydro-2H-pyran-2-yl)benzyl)phenoxy)butanoic acid (39)

To a mixture of (2S,3S,4R,5S,6R)-2-(3-(4-hydroxybenzyl)-4-methylphenyl)-6-(methylthio)tetrahydro-2H-pyran-3,4,5-triyl triacetate (37, 2.01 g, 4.0 mmol) and K$_2$CO$_3$ (2.76 g, 20 mmol) in DMF (8 mL) under nitrogen was added methyl 4-iodobutanoate (0.81 mL, 6.0 mmol). The reaction was stirred overnight at room temperature, then diluted with Et$_2$O. The organic layer was washed with saturated aqueous NaHCO$_3$ and brine (with back extraction), dried over MgSO$_4$, filtered, and concentrated under vacuum. The residue was purified by silica gel flash chromatography (gradient 0-50% EtOAc/hexanes) to give 2.18 g (90% yield) of the ester as a white foam.

This material was treated with LiOH (29 mL, 1 M aq, 29 mmol) in MeOH (14 mL) and THF (29 mL) under nitrogen at 60° C. for 1 hour. The reaction was cooled to room temperature, poured into 1 M aqueous NaHSO$_4$, and extracted with EtOAc. The organic extract was washed with H$_2$O and brine (with back extraction), dried over MgSO$_4$, filtered, and concentrated under vacuum to give 1.71 g (100% yield) of acid 39. $^1$H NMR (400 MHz, MeOH-d$_4$) δ ppm 7.10-7.21 (m, 3H), 7.04 (d, J=8.6 Hz, 2H), 6.76-6.85 (m, 2H), 4.38 (d, J=9.3 Hz, 1H), 4.12 (d, J=9.1 Hz, 1H), 3.97 (t, J=6.2 Hz, 2H), 3.92 (s, 2H), 3.34-3.50 (m, 3H), 2.47 (t, J=7.3 Hz, 2H), 2.20 (s, 3H), 2.14 (s, 3H), 1.98-2.08 (m, 2H); MS (ES−) [M−H]$^−$=461.

Preparation of N-(2-methyl-1-(4-methyl Piperazin-1-yl)-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide (40)

4-(4-(2-methyl-5-((2S,3R,4R,5S,6R)-3,4,5-trihydroxy-6-(methylthio)tetrahydro-2H-pyran-2-yl)benzyl)phenoxy)butanoic acid (39, 1.47 g, 3.2 mmol), 2-amino-2-methyl-1-(4-methylpiperazin-1-yl)propan-1-one (1.07 g, 2 HCl salt, 4.1 mmol), HATU (1.45 g, 3.8 mmol), and DIPEA (2.2 mL, 13 mmol) were combined in CH$_3$CN (32 mL) and stirred overnight at room temperature. To the reaction were added DMAP (39 mg, 0.32 mmol), DIPEA (3.3 mL, 19 mmol), and acetic anhydride (1.5 mL, 16 mmol). The reaction was stirred for 1 hour, then quenched with saturated aqueous NaHCO$_3$, stirred for 1 hour, and extracted twice with EtOAc. The combined organic phases were washed with brine, dried over MgSO$_4$, filtered, and concentrated under vacuum. The residue was purified by silica gel chromatography (gradient 2-10% MeOH/CH$_2$Cl$_2$) to yield 2.27 g (94% yield) of triacetate as a yellow foam.

This material was treated with sodium methoxide (0.55 mL, 25 wt % in MeOH, 2.4 mmol) in MeOH (30 mL) under nitrogen for 18 hours. The reaction was concentrated under vacuum, and the residue was purified by C18 plug (0-25-75% MeOH/H$_2$O) and lyophilized to give 1.40 g (74% yield) of the title compound 40 as a white solid. $^1$H NMR (400 MHz, MeOH-d$_4$) δ ppm 7.09-7.21 (m, 3H), 7.04 (d, J=8.6 Hz, 2H), 6.77-6.84 (m, 2H), 4.39 (d, J=9.3 Hz, 1H), 4.12 (d, J=9.1 Hz, 1H), 3.96 (t, J=6.2 Hz, 2H), 3.92 (s, 2H), 3.65 (br. s., 4H), 3.34-3.50 (m, 3H), 2.39 (t, J=7.6 Hz, 2H), 2.34 (br. s., 4H), 2.203 (s, 3H), 2.198 (s, 3H), 2.14 (s, 3H), 1.97-2.07 (m, 2H), 1.42 (s, 6H); MS (ES+) [M+H]$^+$=630.

6.19. Preparation of 1-(4-(4-(2-methyl-5-((2S,3R,4R,5S,6R)-3,4,5-trihydroxy-6-(methylthio)tetrahydro-2H-pyran-2-yl)benzyl)phenoxy)butanamido)cyclopentanecarboxamide (41)

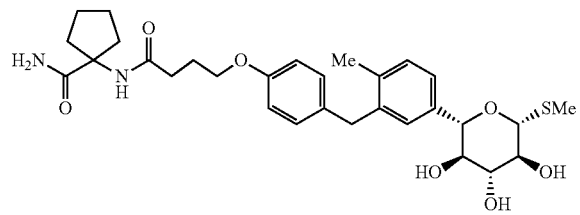

41

4-(4-(2-methyl-5-((2S,3R,4R,5S,6R)-3,4,5-trihydroxy-6-(methylthio)tetrahydro-2H-pyran-2-yl)benzyl)phenoxy)butanoic acid (39, 46 mg, 0.10 mmol), 1-aminocyclopentanecarboxamide (26 mg, 0.20 mmol), HATU (57 mg, 0.15 mmol), and DIPEA (52 µL, 0.30 mmol) were combined in DMF (0.5 mL) and stirred overnight at room temperature. The reaction was diluted with EtOAc, washed with saturated aqueous NaHCO$_3$ and brine (with back extraction), dried over MgSO$_4$, filtered, and concentrated under vacuum. The material was purified by prep HPLC (C18 30×100 mm column, 20-60% CH$_3$CN/10 mM aqueous ammonium formate, 45 mL/min) and lyophilized to give 35 mg (61% yield) of amide 41 as a white solid. $^1$H NMR (400 MHz, MeOH-d$_4$) δ ppm 7.10-7.19 (m, 3H), 7.04 (d, J=8.6 Hz, 2H), 6.81 (m, J=8.6 Hz, 2H), 4.39 (d, J=9.3 Hz, 1H), 4.12 (d, J=9.1 Hz, 1H), 3.96 (t, J=6.2 Hz, 2H), 3.92 (s, 2H), 3.34-3.50 (m, 3H), 2.41 (t, J=7.5 Hz, 2H), 2.12-2.22 (m, 8H), 2.04 (quin, J=6.9 Hz, 2H), 1.93 (dt, J=12.8, 5.1 Hz, 2H), 1.64-1.75 (m, 4H); MS (ES+) [M+H]$^+$=573.

6.20. Preparation of 4-(4-(2-chloro-5-((2S,3R,4R,5S,6R)-3,4,5-trihydroxy-6-(methylthio)tetrahydro-2H-pyran-2-yl)benzyl)phenoxy)-N-(1-hydroxy-2-methylpropan-2-yl)butanamide (42)

42

The same procedure was employed as for amide 41, using 2-amino-2-methylpropan-1-ol, to provide the product 42. $^1$H NMR (400 MHz, MeOH-d$_4$) δ ppm 7.36 (d, J=8.8 Hz, 1H), 7.20-7.29 (m, 2H), 7.10 (d, J=8.6 Hz, 2H), 6.79-6.86 (m, 2H), 4.38 (d, J=9.6 Hz, 1H), 4.13 (d, J=9.6 Hz, 1H), 3.98-4.09 (m, 2H), 3.96 (t, J=6.3 Hz, 2H), 3.56 (s, 2H), 3.44 (t, J=8.6 Hz, 1H), 3.33-3.39 (m, 2H), 2.35 (t, J=7.5 Hz, 2H), 2.13 (s, 3H), 1.96-2.08 (m, 2H), 1.25 (s, 6H); MS (ES+) [M+H]$^+$=554.

6.21. Preparation of 2-methyl-2-(2-(4-(2-methyl-5-((2S,3R,4R,5S,6R)-3,4,5-trihydroxy-6-(methylthio)tetrahydro-2H-pyran-2-yl)benzyl)phenoxy)acetamido)propanamide (43)

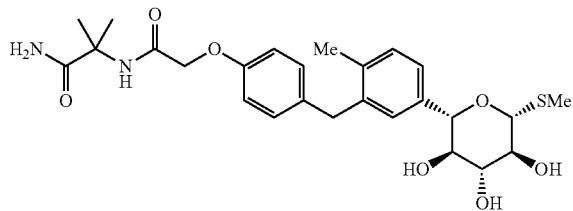

43

The same procedure was employed as for amide 41, using 2-amino-2-methylpropanamide, to provide the product 43. $^1$H NMR (400 MHz, MeOH-d$_4$) δ ppm 7.12-7.21 (m, 3H), 7.09 (d, J=8.6 Hz, 2H), 6.86-6.94 (m, 2H), 4.45 (s, 2H), 4.39 (d, J=9.6 Hz, 1H), 4.13 (d, J=9.1 Hz, 1H), 3.95 (s, 2H), 3.35-3.50 (m, 3H), 2.20 (s, 3H), 2.15 (s, 3H), 1.55 (s, 6H); MS (ES+) [M+H]$^+$=519.

6.22. Preparation of 1-(1-hydroxy-2-methylpropan-2-yl)-3-(2-(4-(2-methyl-5-((2S,3R,4R,5S,6R)-3,4,5-trihydroxy-6-(methylthio)tetrahydro-2H-pyran-2-yl)benzyl)phenoxy)ethyl)urea (45)

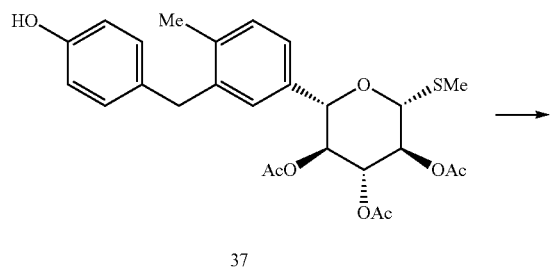

37

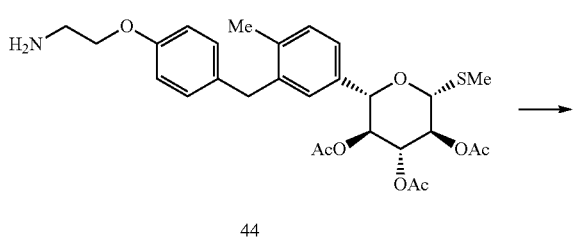

44

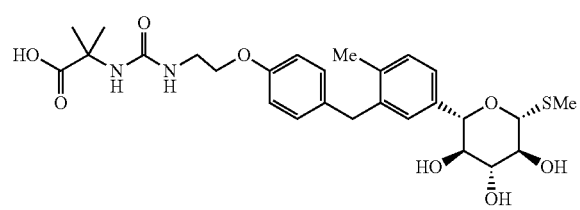

45

Preparation of (2S,3S,4R,5S,6R)-2-(3-(4-(2-aminoethoxy)benzyl)-4-methylphenyl)-6-(methylthio)tetrahydro-2H-pyran-3,4,5-triyl triacetate (44)

(2S,3S,4R,5S,6R)-2-(3-(4-hydroxybenzyl)-4-methylphenyl)-6-(methylthio)tetrahydro-2H-pyran-3,4,5-triyltriacetate (37, 0.50 g, 1.0 mmol), tert-butyl (2-bromoethyl)carbamate (0.62 g, 3.0 mmol), and K$_2$CO$_3$ (0.64 g, 5.0 mmol) were combined in DMF (2 mL) under nitrogen and stirred overnight at room temperature. Additional tert-butyl (2-bromoethyl)carbamate (0.62 g, 3.0 mmol) was added and the reaction was stirred for an additional 3 days. The reaction was diluted with Et$_2$O, washed with saturated aqueous NaHCO$_3$ and brine (with back extraction), dried over MgSO$_4$, filtered, and concentrated under vacuum. The residue was purified by silica gel chromatography (gradient 0-50% EtOAc/hexanes) to give 0.37 g (58% yield) of the alkylated product as a white foam.

A portion of this material (0.34 g, 0.53 mmol) was treated with TFA (0.5 mL) in CH$_2$Cl$_2$ (4.5 mL) for 2 hours. The reaction was concentrated under vacuum. The crude residue was diluted with EtOAc, washed with saturated aqueous NaHCO$_3$ and brine (with back extraction), dried over MgSO$_4$, and concentrated under vacuum to give 0.30 g (100% yield) of amine 44 as a tan foam. $^1$H NMR (400 MHz, CHLOROFORM-d) δ ppm 7.10-7.17 (m, 2H), 7.02 (s, 1H), 6.99 (d, J=8.8 Hz, 2H), 6.79-6.84 (m, 2H), 5.33 (t, J=9.6 Hz, 1H), 5.21 (t, J=9.6 Hz, 1H), 5.11 (t, J=9.7 Hz, 1H), 4.52 (d, J=9.9 Hz, 1H), 4.38 (d, J=9.9 Hz, 1H), 4.03 (t, J=5.2 Hz, 2H), 3.84-3.95 (m, 2H), 3.16 (t, J=5.2 Hz, 2H), 2.20 (s, 3H), 2.17 (s, 3H), 2.09 (s, 3H), 2.01 (s, 3H), 1.76 (s, 3H); MS (ES+) [M+H]$^+$=546.

Preparation of 1-(1-hydroxy-2-methylpropan-2-yl)-3-(2-(4-(2-methyl-5-((2S,3R,4R,5S,6R)-3,4,5-trihydroxy-6-(methylthio)tetrahydro-2H-pyran-2-yl)benzyl)phenoxy)ethyl)urea (45)

To a solution of (2S,3S,4R,5S,6R)-2-(3-(4-(2-aminoethoxy)benzyl)-4-methylphenyl)-6-(methylthio)tetrahydro-2H-pyran-3,4,5-triyltriacetate (44, 55 mg, 0.10 mmol) and 4-nitrophenyl chloroformate (24 mg, 0.12 mmol) in CH$_2$Cl$_2$ (1 mL) was added triethylamine (19 µL, 0.14 mmol). The reaction was stirred for 4 hours, and then 2-amino-2-methylpropan-1-ol (19 µL, 0.20 mmol) was added. The reaction was stirred for 90 min., then diluted with EtOAc, washed with saturated aqueous NaHCO$_3$ and brine (with back extraction), dried over MgSO$_4$, filtered, and concentrated under vacuum.

This material was treated with sodium methoxide (23 µL, 25 wt % in MeOH, 0.10 mmol) in MeOH (1 mL) for 2 hours. The reaction was concentrated under vacuum, and the residue was purified by prep HPLC (C18 30×100 mm column, 10-70% CH$_3$CN/10 mM aqueous ammonium formate, 45 mL/min) to give 21 mg (40% yield) of urea 45 as a white solid. $^1$H NMR (400 MHz, MeOH-d$_4$) δ ppm 7.10-7.19 (m, 3H), 7.04 (d, J=8.8 Hz, 2H), 6.79-6.86 (m, 2H), 4.38 (d, J=9.6 Hz, 1H), 4.12 (d, J=9.1 Hz, 1H), 3.95 (t, J=5.3 Hz, 2H), 3.93 (s, 2H), 3.52 (s, 2H), 3.33-3.49 (m, 5H), 2.20 (s, 3H), 2.14 (s, 3H), 1.24 (s, 6H); MS (ES+) [M+H]$^+$=535.

6.23. Preparation of 1-(2-(4-(2-methyl-5-((2S,3R,4R,5S,6R)-3,4,5-trihydroxy-6-(methylthio)tetrahydro-2H-pyran-2-yl)benzyl)phenoxy)ethyl)guanidine (46)

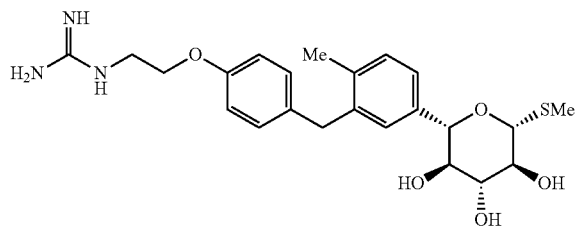

46

To a solution of (2S,3S,4R,5S,6R)-2-(3-(4-(2-aminoethoxy)benzyl)-4-methylphenyl)-6-(methylthio)tetrahydro-2H-pyran-3,4,5-triyl triacetate (44, 31 mg, 0.057 mmol) and 3,5-dimethyl-1H-pyrazole-1-carboximidamide nitrate (23 mg, 0.11 mmol) in CH$_3$CN was added DIPEA (30 μL, 0.17 mmol). The reaction was heated at 60° C. for 4 hours, then cooled to room temperature and concentrated under vacuum. The residue was dissolved in MeOH and treated with a few drops of NaOMe (25 wt % in MeOH) for 1 hour. The reaction was concentrated under vacuum, and the residue was purified by prep HPLC (C18 30×100 mm column, 5-40% CH$_3$CN/10 mM aqueous ammonium formate, 45 mL/min) to give urea 46 (9 mg, 34% yield) as the formate salt. $^1$H NMR (400 MHz, MeOH-d$_4$) δ ppm 7.11-7.20 (m, 3H), 7.07 (d, J=8.6 Hz, 2H), 6.81-6.89 (m, 2H), 4.39 (d, J=9.3 Hz, 1H), 4.12 (d, J=9.1 Hz, 1H), 4.08 (t, J=4.9 Hz, 2H), 3.94 (s, 2H), 3.58 (t, J=5.1 Hz, 2H), 3.34-3.48 (m, 3H), 2.20 (s, 3H), 2.14 (s, 3H); MS (ES+) [M+H]$^+$=462.

6.24. Preparation of (2S,3R,4R,5S,6R)-2-(3-(4-(3-((1-hydroxy-2-methylpropan-2-yl)amino)propoxy)benzyl)-4-methylphenyl)-6-(methylthio)tetrahydro-2H-pyran-3,4,5-triol (49)

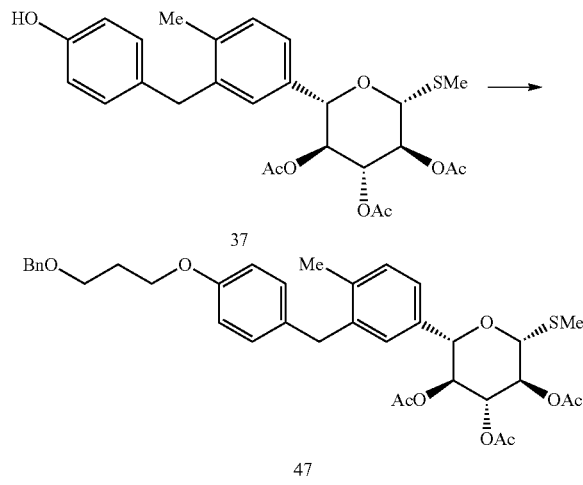

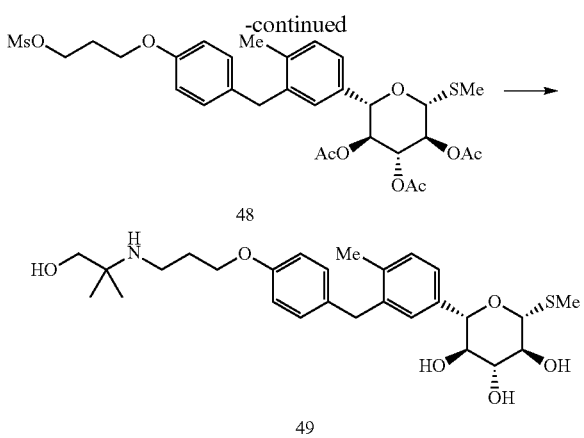

Preparation of (2S,3S,4R,5S,6R)-2-(3-(4-(3-(benzyloxy)propoxy)benzyl)-4-methylphenyl)-6-(methylthio)tetrahydro-2H-pyran-3,4,5-triyltriacetate (47)

(2S,3S,4R,5S,6R)-2-(3-(4-hydroxybenzyl)-4-methylphenyl)-6-(methylthio)tetrahydro-2H-pyran-3,4,5-triyltriacetate (37, 2.01 g, 4.0 mmol), ((3-bromopropoxy)methyl)benzene (1.41 mL, 8.0 mmol), Bu$_4$NI (148 mg, 0.40 mmol), and K$_2$CO$_3$ (2.76 g, 20 mmol) were combined in DMF (8 mL) under nitrogen and stirred overnight at room temperature. The reaction was diluted with Et$_2$O, washed with saturated aqueous NaHCO$_3$ and brine (with back extraction), dried over MgSO$_4$, filtered, and concentrated under vacuum. The residue was purified by silica gel chromatography (gradient 0-50% EtOAc/hexanes) to give alkylated product 47 as a glassy solid (2.36 g, 91% yield). $^1$H NMR (400 MHz, CHLOROFORM-d) δ ppm 7.28-7.36 (m, 5H), 7.10-7.18 (m, 2H), 7.03 (s, 1H), 6.97 (d, J=8.6 Hz, 2H), 6.77-6.84 (m, 2H), 5.33 (t, J=9.6 Hz, 1H), 5.21 (t, J=9.6 Hz, 1H), 5.12 (t, J=9.6 Hz, 1H), 4.48-4.54 (m, 3H), 4.38 (d, J=9.9 Hz, 1H), 4.06 (t, J=6.3 Hz, 2H), 3.83-3.96 (m, 2H), 3.66 (t, J=6.2 Hz, 2H), 2.21 (s, 3H), 2.17 (s, 3H), 2.10 (s, 3H) 2.04-2.12 (m, 2H), 2.01 (s, 3H), 1.75 (s, 3H); MS (ES+) [M+NH$_4$]$^+$=668.

Preparation of (2S,3S,4R,5S,6R)-2-(4-methyl-3-(4-(3-((methylsulfonyl)oxy)propoxy)benzyl)phenyl)-6-(methylthio)tetrahydro-2H-pyran-3,4,5-triyltriacetate (48)

(2S,3S,4R,5S,6R)-2-(3-(4-(3-(benzyloxy)propoxy)benzyl)-4-methylphenyl)-6-(methylthio)tetrahydro-2H-pyran-3,4,5-triyl triacetate (47, 2.36 g, 3.6 mmol) was hydrogenated over 10% Pd/C (50% wet, 0.38 g, 0.18 mmol) in THF (36 mL) under hydrogen at atmospheric pressure for 18 hours. The reaction was filtered through celite and concentrated under vacuum. The residue was purified by silica gel chromatography (gradient 0-70% EtOAc/hexanes) to give the corresponding alcohol as a white solid (1.90 g, 93% yield).

This material was dissolved in CH$_2$Cl$_2$ (34 mL) under nitrogen. Triethylamine (0.61 mL, 4.4 mmol) was added, followed by methanesulfonyl chloride (0.32 mL, 4.1 mmol). The reaction was stirred for 2 hours. It was diluted with EtOAc, washed with 1 M aqueous HCl, H$_2$O, and brine (with back extraction), dried over MgSO$_4$, filtered, and concentrated under vacuum to give mesylate 48 as a white foam (2.20 g, 100% yield). $^1$H NMR (400 MHz, CHLOROFORM-d) δ ppm 7.10-7.18 (m, 2H), 7.03 (s, 1H), 6.99

(d, J=8.6 Hz, 2H), 6.75-6.85 (m, 2H), 5.33 (t, J=9.3 Hz, 1H), 5.21 (t, J=9.6 Hz, 1H), 5.12 (t, J=9.6 Hz, 1H), 4.52 (d, J=9.9 Hz, 1H), 4.45 (t, J=6.1 Hz, 2H), 4.39 (d, J=9.9 Hz, 1H), 4.06 (t, J=5.9 Hz, 2H), 3.83-3.96 (m, 2H), 3.00 (s, 3H), 2.20 (s, 3H), 2.18-2.28 (m, 2H), 2.17 (s, 3H), 2.10 (s, 3H), 2.01 (s, 3H), 1.76 (s, 3H); MS (ES+) [M+NH$_4$]$^+$=656.

Preparation of (2S,3R,4R,5S,6R)-2-(3-(4-(3-((1-hydroxy-2-methylpropan-2-yl)amino)propoxy)benzyl)-4-methylphenyl)-6-(methylthio)tetrahydro-2H-pyran-3,4,5-triol (49)

(2S,3S,4R,5S,6R)-2-(4-methyl-3-(4-(3-((methylsulfonyl)oxy)propoxy)benzyl)phenyl)-6-(methylthio)tetrahydro-2H-pyran-3,4,5-triyltriacetate (48, 1.23 g, 1.9 mmol) and 2-amino-2-methylpropan-1-ol (0.52 g, 5.8 mmol) were dissolved in isopropyl alcohol (3.9 mL) and CH$_3$CN (3.9 mL) under nitrogen. The reaction was heated overnight at 90° C., then cooled to room temperature. It was diluted with EtOAc, washed with saturated aqueous NaHCO$_3$ and brine (with back extraction), dried over MgSO$_4$, filtered, and concentrated under vacuum. The residue was purified by silica gel chromatography (gradient 0-10% [10% NH$_4$OH/MeOH] CH$_2$Cl$_2$) to give 1.04 g of the protected sugar as a white solid.

This material was dissolved in MeOH (16 mL) under nitrogen and treated with NaOMe (0.19 mL, 25 wt % in MeOH, 0.8 mmol) for 2 hours. The reaction was concentrated under vacuum, and the residue was purified by C18 plug (0-25-80% MeOH/H$_2$O). The material was purified again by prep HPLC (C18 30×250 mm column, 5-80% CH$_3$CN/10 mM aqueous ammonium formate, 45 mL/min), dissolved in H$_2$O, and lyophilized to give the formate salt of aminoalcohol 49 as a white solid (710 mg, 68% yield). $^1$H NMR (400 MHz, MeOH-d$_4$) δ ppm 7.11-7.21 (m, 3H), 7.07 (d, J=8.6 Hz, 2H), 6.86 (m, J=8.6 Hz, 2H), 4.39 (d, J=9.3 Hz, 1H), 4.06-4.15 (m, 3H), 3.88-3.98 (m, 2H), 3.55 (s, 2H), 3.34-3.50 (m, 3H), 3.18 (t, J=7.5 Hz, 2H), 2.20 (s, 3H), 2.14 (s, 3H), 2.08-2.18 (m, 2H), 1.32 (s, 6H); MS (ES+) [M+H]$^+$=506.

6.25. Preparation of (2S,3R,4R,5S,6R)-2-(3-(4-(3-((3-(dimethylamino)-2,2-dimethylpropyl)amino)propoxy)benzyl)-4-methylphenyl)-6-(methylthio)tetrahydro-2H-pyran-3,4,5-triol (50)

(2S,3S,4R,5S,6R)-2-(4-Methyl-3-(4-(3-((methylsulfonyl)oxy)propoxy)benzyl)phenyl)-6-(methylthio)tetrahydro-2H-pyran-3,4,5-triyltriacetate (48, 1.28 g, 2.0 mmol) and N$^1$,N$^1$,2,2-tetramethylpropane-1,3-diamine (0.64 mL, 4.0 mmol) were dissolved in isopropyl alcohol (4 mL) and CH$_3$CN (4 mL) under nitrogen. The reaction was heated overnight at 90° C., and then cooled to room temperature. MeOH (8 mL) and sodium methoxide (0.69 mL, 25 wt % in MeOH, 3.0 mmol) were added, and the reaction was stirred for 2 hours, then neutralized with acetic acid and concentrated under vacuum. The residue was purified twice by prep HPLC (C18 30×250 mm column, 5-60% CH$_3$CN/10 mM aqueous ammonium formate, 45 mL/min and C18 30×100 mm column, 5-92% MeOH/H$_2$O (with 0.1% formic acid), 45 mL/min) and lyophilized to give the formate salt of the product 50 as a white solid (0.52 g, 44% yield). $^1$H NMR (400 MHz, MeOH-d$_4$) δ ppm 7.11-7.20 (m, 3H), 7.08 (d, J=8.6 Hz, 2H), 6.86 (d, J=8.6 Hz, 2H), 4.39 (d, J=9.6 Hz, 1H), 4.08-4.15 (m, 3H), 3.94 (s, 2H), 3.34-3.49 (m, 3H), 3.20 (t, J=6.8 Hz, 2H), 3.04 (s, 2H), 2.62 (s, 2H), 2.32 (s, 6H), 2.19 (s, 3H), 2.15 (s, 3H) 2.10-2.18 (m, 2H), 1.05 (s, 6H); MS (ES+) [M+H]$^+$=547.

6.26. Preparation of 2,2-dimethyl-3-((3-(4-(2-methyl-5-((2S,3R,4R,5S,6R)-3,4,5-trihydroxy-6-(methylthio)tetrahydro-2H-pyran-2-yl)benzyl)phenoxy)propyl)-amino)propanamide (51)

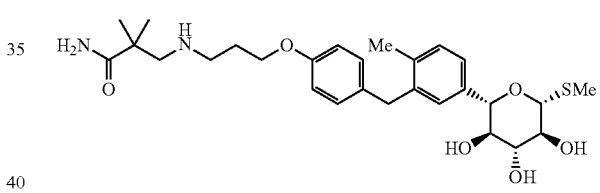

51

The same procedure was employed as for amine 50, using 3-amino-2,2-dimethylpropanamide, to provide the product 51. The material was purified by prep HPLC (C18 30×100 mm column, 5-60% CH$_3$CN/10 mM aqueous ammonium formate, 45 mL/min) and lyophilized to give the formate salt the product as a white solid. $^1$H NMR (400 MHz, MeOH-d$_4$) δ ppm 7.11-7.21 (m, 3H), 7.06 (d, J=8.1 Hz, 2H), 6.88 (m, J=8.3 Hz, 2H), 4.39 (d, J=9.3 Hz, 1H), 4.05-4.16 (m, 3H), 3.94 (s, 2H), 3.35-3.53 (m, 3H), 3.23 (t, J=6.9 Hz, 2H), 3.07 (s, 2H), 2.20 (s, 3H), 2.16-2.24 (m, 2H), 2.14 (s, 3H), 1.33 (s, 6H); MS (ES+) [M+H]$^+$=533.

50

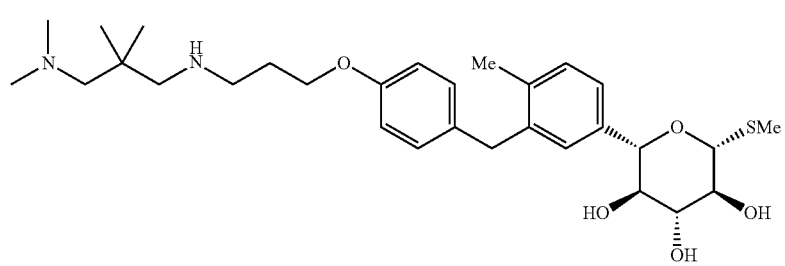

6.27. Preparation of 1-((2-(4-(2-methyl-5-((2S,3R, 4R,5S,6R)-3,4,5-trihydroxy-6-(methylthio)tetrahydro-2H-pyran-2-yl)benzyl)phenoxy)ethyl)amino) cyclopentanecarboxamide (52)

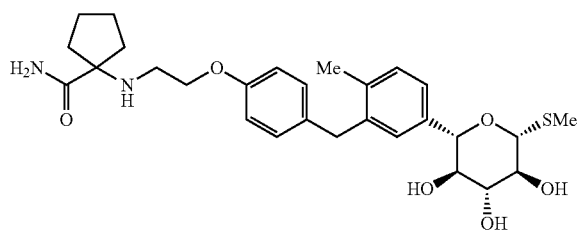

The same procedure was employed as for amine 50, using 1-aminocyclopentanecarboxamide, to provide the product 52. $^1$H NMR (400 MHz, MeOH-d$_4$) δ ppm 7.11-7.21 (m, 3H), 7.06 (d, J=8.3 Hz, 2H), 6.85 (m, J=8.6 Hz, 2H), 4.39 (d, J=9.6 Hz, 1H), 4.12 (d, J=9.3 Hz, 1H), 4.06 (t, J=4.9 Hz, 2H), 3.94 (s, 2H), 3.34-3.54 (m, 3H), 2.92 (t, J=4.8 Hz, 2H), 2.20 (s, 3H), 2.14 (s, 3H), 2.06-2.13 (m, 2H), 1.75-1.83 (m, 6H); MS (ES+) [M+H]$^+$=531.

6.28. Preparation of (2S,3R,4R,5S,6R)-2-(3-(4-(2,3-dihydroxypropoxy)benzyl)-4-methylphenyl)-6-(methylthio)tetrahydro-2H-pyran-3,4,5-triol (53)

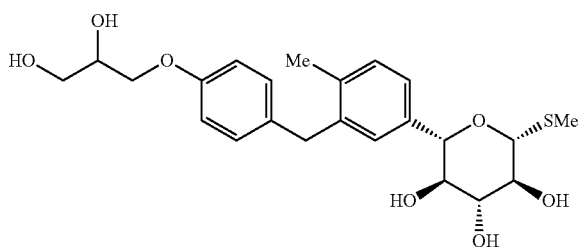

To a solution of (2S,3S,4R,5S,6R)-2-(3-(4-hydroxybenzyl)-4-methylphenyl)-6-(methylthio)tetrahydro-2H-pyran-3,4,5-triyltriacetate (37, 50 mg, 0.10 mmol) in EtOH (1 mL) under nitrogen was added triethylamine (1.4 μL, 0.010 mmol) and glycidol (10 μL, 0.15 mmol). The reaction was heated at 80° C. overnight, then recharged with triethylamine and glycidol and heated at 90° C. for 5 hours. The reaction was cooled to room temperature, diluted with EtOAc, washed with saturated aqueous NaHCO$_3$ and brine (with back extraction), dried over MgSO$_4$, filtered, and concentrated under vacuum. The material was purified twice by prep HPLC (C18 30×100 mm column, 20-60% CH$_3$CN/ 10 mM aqueous ammonium formate, 45 mL/min) and lyophilized to provide diol 53 as a white solid (12 mg, 27% yield). $^1$H NMR (400 MHz, MeOH-d$_4$) δ ppm 7.10-7.19 (m, 3H), 7.05 (d, J=8.8 Hz, 2H), 6.81-6.88 (m, 2H), 4.39 (d, J=9.3 Hz, 1H), 4.12 (d, J=9.1 Hz, 1H), 3.89-4.05 (m, 5H), 3.59-3.71 (m, 2H), 3.35-3.49 (m, 3H), 2.20 (s, 3H), 2.14 (s, 3H); MS (ES+) [M+NH$_4$]$^+$=468.

6.29. Synthesis of 2-amino-2-methyl-1-(4-methylpiperazin-1-yl)propan-1-one (55)

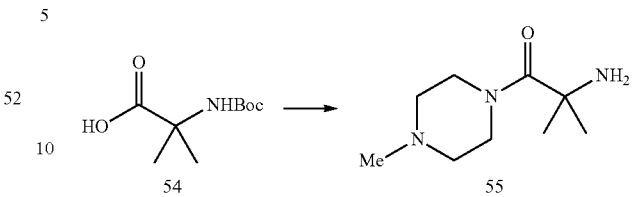

2-((tert-Butoxycarbonyl)amino)-2-methylpropanoic acid (Boc-Aib-OH, 54, 10.0 g, 49.2 mol), EDC.HCl (11.3 g, 59.0 mmol), HOBt (9.97 g, 73.8 mmol) and DIPEA (25.6 mL, 148 mmol) were stirred in 250 mL of THF until all solids dissolved. N-methyl-piperazine was added (10.9 mL, 98.4 mmol) and the reaction was stirred at room temperature for 18 hrs. The mixture was diluted with 300 mL of EtOAc and washed twice with saturated aqueous NaHCO$_3$. The organic layer was then washed with brine, dried over MgSO$_4$, filtered, and the solvent was removed in vacuo. This crude material was dissolved in 300 mL of CH$_3$CN. HCl (4N in dioxane, 49 mL, 196 mmol) was added over 10 minutes. The reaction was stirred for 8 hrs, during which time the product forms a white precipitate. The product was filtered, washed with CH$_2$Cl$_2$, and dried under high vacuum over night to provide the product 55 as the bis-hydrochloride salt (10.4 g, 82% yield). $^1$H NMR (400 MHz, DMSO-d$_6$) δ ppm 8.30 (br. s., 3H), 4.35 (d, J=13.6 Hz, 2H), 3.52 (br. s., 2H), 3.41 (d, J=11.1 Hz, 2H), 3.01 (q, J=11.1 Hz, 2H), 2.77 (d, J=3.5 Hz, 3H), 1.56 (s, 6H). MS (ES+) [M+H]$^+$=186.

6.30. Preparation of (1-aminocyclopentyl)(4-methylpiperazin-1-yl)methanone (56)

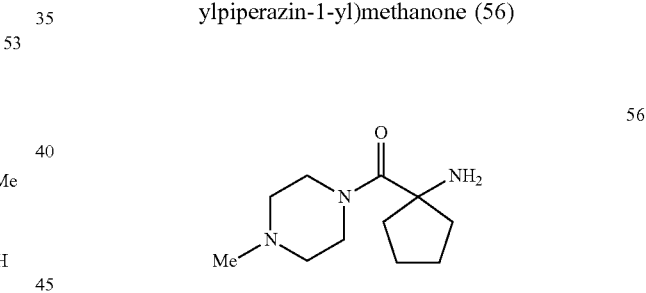

The same procedure was employed as used for amide 55, starting with 1-((tert-butoxycarbonyl)amino)cyclopentanecarboxylic acid, to provide the product 56. $^1$H NMR (400 MHz, DMSO-d$_6$) δ ppm 11.56 (br. s., 1H), 8.32 (br. s., 3H), 3.41 (d, J=11.6 Hz, 4H), 3.05 (q, J=10.6 Hz, 2H), 2.76 (d, J=4.3 Hz, 3H), 2.10-2.22 (m, 2H), 1.81-2.02 (m, 8H). MS (ES+) [M+H]$^+$=212.

6.31. Preparation of 2-amino-2-methyl-N-(1-methylpiperidin-4-yl)propanamide (58)

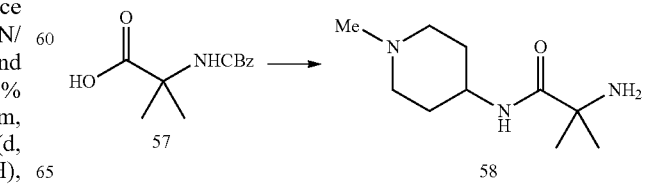

2-(((Benzyloxy)carbonyl)amino)-2-methylpropanoic acid (Z-Aib-OH, 57, 25.0 g, 105 mol), EDC.HCl (24.2 g, 126 mmol), HOBt (21.2 g, 157 mmol) and DIPEA (54.9 mL, 315 mmol) were stirred in 500 mL of THF until all solids dissolved. N-Methylpiperidin-4-amine was added (15.9 mL, 126 mmol) and the reaction was stirred at room temperature for 18 hrs. The mixture was diluted with 600 mL of EtOAc and washed twice with saturated aqueous NaHCO$_3$. The organic layer was then washed with brine, dried over MgSO$_4$, filtered, and the solvent was removed in vacuo. This crude material was dissolved in 150 mL of THF and 150 mL of MeOH. Pd/C (10% wet, 2.92 g) was added and the reaction was stirred under atmospheric hydrogen pressure for 8 hrs. The reaction was filtered over Celite with excess MeOH, the solvents removed in vacuo, and the resulting light yellow solid was dried under high vacuum over night to provide the product 57 as the free base (17.4 g, 85% yield). $^1$H NMR (400 MHz, CHLOROFORM-d) δ ppm 7.54 (br. s., 1H), 3.62-3.77 (m, 1H), 2.75 (d, J=11.6 Hz, 2H), 2.27 (s, 3H), 2.11 (t, J=10.9 Hz, 2H), 1.89 (dq, J=12.6, 3.8 Hz, 2H), 1.48 (qd, J=11.5, 3.5 Hz, 2H), 1.30-1.39 (m, 6H). [M+H]$^+$=200.

6.32. Preparation of 2-amino-N-(2-(dimethylamino)ethyl)-2-methylpropanamide (59)

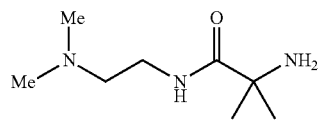

The same procedure was employed as used for amide 57, using N,N-dimethylethane-1,2-diamine, to provide the product 59. $^1$H NMR (400 MHz, CHLOROFORM-d) δ ppm 7.78 (br. s., 1H), 3.31 (q, J=6.1 Hz, 2H), 2.42 (t, J=6.2 Hz, 2H), 2.25 (s, 6H), 1.68 (br. s., 2H), 1.36 (s, 6H). [M+H]$^+$=174.

6.33. Preparation of N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-((S)-methylsulfinyl)tetrahydro-2H-pyran-2-yl)benzyl)phenyl)butanamide (61)

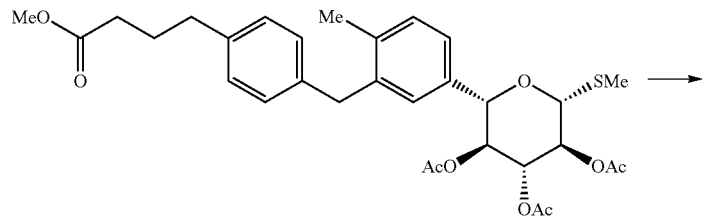

9

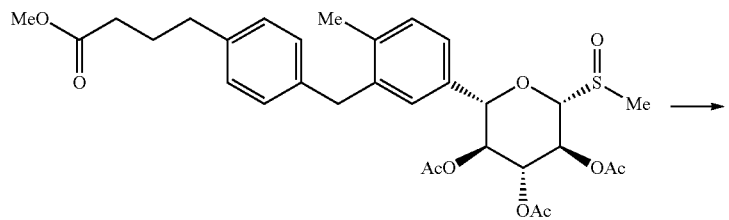

60

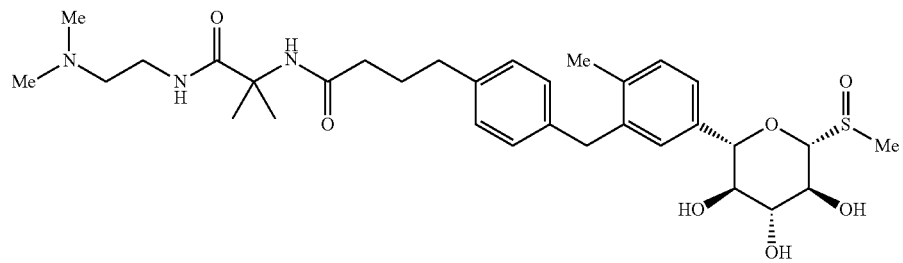

61

Preparation of (2S,3S,4R,5S,6R)-2-(3-(4-(4-methoxy-4-oxobutyl)benzyl)-4-methylphenyl)-6-((S)-methylsulfinyl)tetrahydro-2H-pyran-3,4,5-triyl-triacetate (60)

Peracetic acid (32% in dilute HOAc, 0.12 mL, 0.512 mmol) was added to a solution of (2S,3S,4R,5S,6R)-2-(3-(4-(4-methoxy-4-oxobutyl)benzyl)-4-methylphenyl)-6-(methylthio)tetrahydro-2H-pyran-3,4,5-triyltriacetate (9, 100 mg, 0.170 mmol) in 1 mL of HOAc and 2 mL of $CH_3CN$ at 0° C. The reaction was stirred for 20 min at 0° C. The reaction was quenched with 1N aqueous NaOH, then extracted twice with EtOAc. The combined organic layers were washed with brine, dried over $MgSO_4$, filtered, and the solvents were removed in vacuo to provide a 2:1 diastereomeric mixture of sulfoxides 60 (60 mg, 58% yield) that was carried to the next step without further purification. $^1$H NMR (400 MHz, CHLOROFORM-d, 2:1 mixture of diastereomers at S, designated as major $H_a$ and minor $H_b$) δ ppm 7.11-7.17 (m, 2H), 7.05-7.09 (m, 2H), 6.97-7.02 (m, 3H), 5.59 (t, J=9.3 Hz, $1H_b$), 5.46 (t, J=9.3 Hz, $1H_b$), 5.41 (t, J=9.6 Hz, $1H_a$), 5.21 (t, J=9.9 Hz, $1H_a$), 5.17 (t, J=9.3 Hz, $1H_b$), 5.13 (t, J=9.9 Hz, $1H_a$), 4.50 (t, J=10.4 Hz, $1H_a$), 4.48 (d, J=9.9 Hz, $1H_a$), 4.46 (d, J=10.1 Hz, $1H_b$), 4.31 (d, J=10.1 Hz, $1H_b$), 3.93 (m, $2H_b$), 3.92 (m, $2H_a$), 3.66 (s, 3H), 2.67 (s, $3H_a$), 2.64 (s, $3H_b$), 2.61 (t, J=7.8 Hz, 2H), 2.33 (t, J=7.3 Hz, 2H), 2.23 (s, 3H), 2.09 (s, $3H_a$), 2.08 (s, $3H_b$), 2.02 (s, $3H_b$), 2.01 (s, $3H_a$), 1.93 (quin, J=7.3 Hz, 2H), 1.75 (s, $3H_a$), 1.74 (s, $3H_b$). MS (ES+) [M+H]$^+$=603.

Preparation of N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-((S)-methylsulfinyl)-tetrahydro-2H-pyran-2-yl)benzyl)phenyl)butanamide (61)

Sulfoxides 60 (60 mg, 0.10 mmol) were suspended in 2.5 mL of a 2:2:1 mixture of MeOH/$H_2O$/THF. LiOH (24 mg, 1.0 mmol) was added. The reaction was stirred at room temperature for 4 hrs, over which time the starting material went into solution. The reaction was quenched with saturated aqueous $NaHSO_4$. This acidic layer was extracted three times with EtOAc. The combined organic layers were washed with brine, dried over $MgSO_4$, filtered, and the solvents were removed in vacuo. This crude residue was dissolved in 1 mL of $CH_3CN$. EDC.HCl (31 mg, 0.16 mmol), HOBt (31 mg, 0.16 mmol), and DIPEA (50 μL, 0.30 mmol) were added and stirred for 10 minutes. 2-Amino-N-(2-(dimethylamino)ethyl)-2-methylpropanamide (30 mg, 0.17 mmol) in 0.5 mL of $CH_3CN$ was added. The reaction was stirred at room temperature overnight. Upon reaction completion, the solvent was removed in vacuo. The residue was purified by preparative HPLC (C18 30×100 mm column, 5-95% MeOH/10 mM aqueous formic acid, 45 mL/min) to provide sulfoxide 61 as the formate salt (23 mg, 35% yield) as a 2:1 diastereomeric mixture of sulfoxides. $^1$H NMR (400 MHz, MeOH-$d_4$, 2:1 mixture of diastereomers at S, designated as major $H_a$ and minor $H_b$) δ ppm 8.54 (br. s, 1H, formate), 7.14-7.19 (m, 3H), 7.04-7.10 (m, 4H), 4.47 (d, J=9.6 Hz, $1H_a$), 4.28 (d, J=9.1 Hz, $1H_b$), 4.26 (d, J=9.3 Hz, $1H_a$), 4.12 (d, J=9.9 Hz, $1H_b$), 3.97 (s, $3H_b$), 3.96 (s, $3H_a$), 3.82 (t, J=9.6 Hz, $1H_b$), 3.68 (t, J=9.1 Hz, $1H_a$), 3.60 (t, J=9.0 Hz, $1H_b$), 3.58 (t, J=8.8 Hz, $1H_a$), 3.45 (t, J=5.6 Hz, 2H), 3.39-3.47 (m, $1H_a$+1 $H_b$), 2.91 (t, J=5.1 Hz, 2H), 2.73 (s, $3H_a$), 2.64 (s, 6H), 2.61 (s, $3H_b$), 2.60 (t, J=7.6 Hz, 2H), 2.22 (s, $3H_a$), 2.21 (s, $3H_b$), 2.21 (t, J=7.6 Hz, 2H), 1.87 (quin, J=7.3 Hz, 2H), 1.41 (s, 6H). MS (ES+) [M+H]$^+$=618.

6.34. Preparation of N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-(methylsulfonyl)tetrahydro-2H-pyran-2-yl)benzyl)phenyl)butanamide (63)

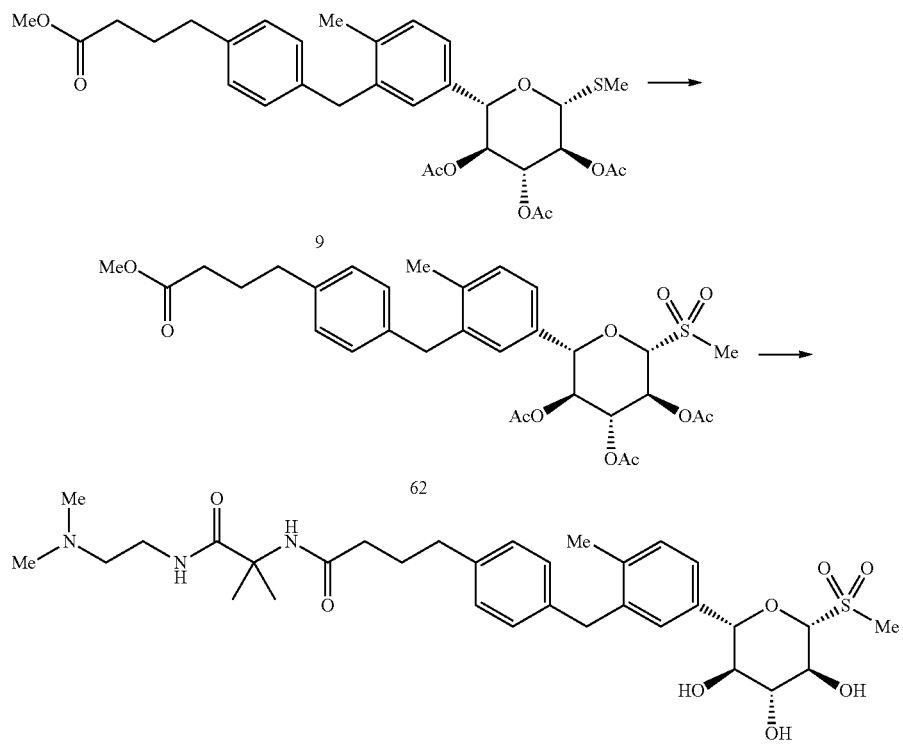

Preparation of (2S,3S,4R,5S,6R)-2-(3-(4-(4-methoxy-4-oxobutyl)benzyl)-4-methylphenyl)-6-(methylsulfonyl)tetrahydro-2H-pyran-3,4,5-triyltriacetate (62)

Urea hydrogen peroxide (UHP, 48 mg, 0.512 mmol) and phthalic anhydride (151 mg, 1.02 mmol) were dissolved in 1.5 mL of $CH_3CN$ and 0.3 mL of MeOH. (2S,3S,4R,5S,6R)-2-(3-(4-(4-Methoxy-4-oxobutyl)benzyl)-4-methylphenyl)-6-(methylthio)tetrahydro-2H-pyran-3,4,5-triyltriacetate (9, 100 mg, 0.170 mmol) dissolved in 2 mL of $CH_3CN$ was added. The reaction was stirred at room temperature for 16 hrs. The reaction was charged with an additional UHP (12 mg, 0.128 mmol) and phthalic anhydride (38 mg, 0.255 mmol) and stirred for 1 hr. Upon full conversion to the sulfone, the reaction was quenched with saturated aqueous $NaHCO_3$. This aqueous layer was extracted three times with EtOAc. The combined organic layers were washed with brine, dried over $MgSO_4$, filtered, and the solvents were removed in vacuo to provide sulfone 62 (95 mg, 92% yield) that was carried to the next step without further purification. $^1$H NMR (400 MHz, CHLOROFORM-d) δ ppm 7.11-7.20 (m, 2H), 7.08 (d, J=8.1 Hz, 2H), 6.93-7.04 (m, 3H), 5.57 (t, J=9.7 Hz, 1H), 5.41 (t, J=9.3 Hz, 1H), 5.17 (t, J=9.7 Hz, 1H), 4.49 (d, J=9.7 Hz, 1H), 4.52 (d, J=9.7 Hz, 1H), 3.93 (m, 2H), 3.67 (s, 3H), 2.92 (s, 3H), 2.62 (t, J=7.5 Hz, 2H), 2.33 (t, J=7.5 Hz, 2H), 2.24 (s, 3H), 2.09 (s, 3H), 2.02 (s, 3H), 1.94 (quin, J=7.5 Hz, 2H), 1.75 (s, 3H). MS (ES+) [M+H]$^+$=619.

Preparation of N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-(methylsulfonyl)tetrahydro-2H-pyran-2-yl)benzyl)phenyl)butanamide (63)

Sulfone 62 (95 mg, 0.15 mmol) were suspended in 5 mL of a 2:2:1 mixture of MeOH/$H_2O$/THF. LiOH (37 mg, 1.53 mmol) was added. The reaction was stirred at room temperature for 4 hrs, over which time the starting material went into solution. The reaction was quenched with saturated aqueous $NaHSO_4$. This acidic layer was extracted three times with EtOAc. The combined organic layers were washed with brine, dried over $MgSO_4$, filtered, and the solvents were removed in vacuo. This crude residue was dissolved in 1.5 mL of $CH_3CN$. EDC.HCl (43 mg, 0.22 mmol), HOBt (43 mg, 0.22 mmol), and DIPEA (75 μL, 0.30 mmol) were added and stirred for 10 min. 2-Amino-N-(2-(dimethylamino)ethyl)-2-methylpropanamide (30 mg, 0.45 mmol) in 0.5 mL of $CH_3CN$ was added. The reaction was stirred at room temperature overnight. Upon reaction completion, the solvent was removed in vacuo. The residue was purified by preparative HPLC (C18 30×100 mm column, 5-95% MeOH/10 mM aqueous formic acid, 45 mL/min) to provide the title compound 63 as the formate salt (30 mg, 30% yield). $^1$H NMR (400 MHz, MeOH-$d_4$) δ ppm 8.54 (br. s, 1H, formate), 7.12-7.22 (m, 3H), 7.10 (d, J=8.0 Hz, 2H), 7.06 (d, J=8.0 Hz, 2H), 4.52 (d, J=9.5 Hz, 1H), 4.28 (d, J=9.5 Hz, 1H), 3.96 (s, 2H), 3.88 (t, J=9.2 Hz, 1H), 3.56 (t, J=8.9 Hz, 1H), 3.45 (t, J=5.3 Hz, 2H), 3.41 (t, J=9.3 Hz, 1H), 2.93 (s, 3H), 2.89 (t, J=5.3 Hz, 2H), 2.64 (s, 6H), 2.61 (t, J=7.8 Hz, 2H), 2.21 (t, J=8.0 Hz, 5H), 2.14-2.29 (m, 3H), 1.88 (quin, J=7.5 Hz, 2H), 1.41 (s, 6H). MS (ES+) [M+H]$^+$=634.

6.35. Preparation of Sulfoxide/N-Oxide (64) and Sulfone/N-Oxide (65)

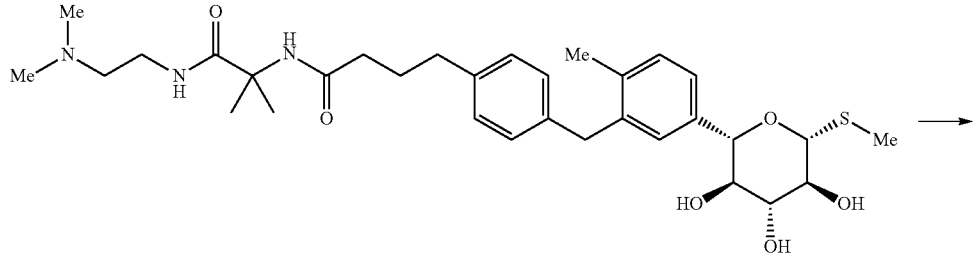

13

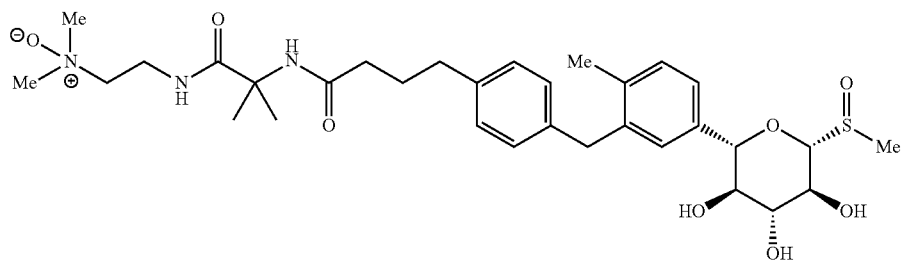

64

+

-continued

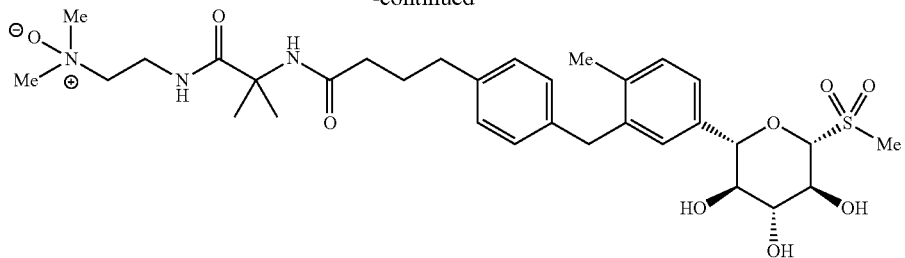

65

To a solution of N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide (13, 30 mg, 0.050 mmol) in 0.5 mL of $CH_2Cl_2$ was added m-chloroperbenzoic acid (22 mg, 0.125 mmol). The reaction was stirred for 5 minutes and the solvent was removed in vacuo. The residue was purified by preparative HPLC (C18 30×100 mm column, 5-100% $CH_3CN$/10 mM aqueous ammonium formate, 45 mL/min) to provide oxidized products 64 (16 mg, 50% yield) and 65 (3 mg, 9% yield).

N,N-dimethyl-2-(2-methyl-2-(4-(4-(2-methyl-5-((2S,3R,4R,5S,6R)-3,4,5-trihydroxy-6-((S)-methylsulfinyl)tetrahydro-2H-pyran-2-yl)benzyl)phenyl)butanamido)propanamido) ethanamine oxide (64, 2:1 mixture of diastereomers at S, designated as major $H_a$ and minor $H_b$): $^1$H NMR (400 MHz, MeOH-$d_4$) δ ppm 8.46 (s, 2H, formate), 7.14-7.26 (m, 3H), 7.04-7.10 (m, 4H), 4.46 (d, J=9.6 Hz, $1H_a$), 4.27 (d, J=9.6 Hz, $1H_b$), 4.26 (d, J=9.6 Hz, $1H_a$), 4.12 (d, J=9.9 Hz, $1H_b$), 3.97 (S, $3H_b$), 3.96 (S, $3H_a$), 3.82 (t, J=9.1 HZ, $1H_b$), 3.68 (t, J=9.1 HZ, $1H_a$), 3.59 (t, J=8.9 HZ, $1H_b$), 3.58 (t, J=8.9 HZ, $1H_a$), 3.43 (t, J=6.1 HZ, 2H), 3.41 (t, J=9.1 HZ, $1H_a$+1 $H_b$ overlapping), 3.20 (s, 6H), 2.72 (s, $3H_a$), 2.62 (s, $3H_b$), 2.60 (t, J=7.6 Hz, 2H), 2.23 (s, $3H_a$), 2.22 (s, $3H_b$), 2.20 (t, J=7.6 Hz, 2H), 1.86 (quin, J=7.6 Hz, 2H), 1.41 (s, 6H). MS (ES+) [M+H]$^+$=634.

N,N-dimethyl-2-(2-methyl-2-(4-(4-(2-methyl-5-((2S,3R,4R,5S,6R)-3,4,5-trihydroxy-6-(methylsulfonyl)tetrahydro-2H-pyran-2-yl)benzyl)phenyl)butanamido)propanamido) ethanamine oxide (65): $^1$H NMR (400 MHz, MeOH-$d_4$) δ ppm 8.41 (s, 1H, formate), 7.12-7.23 (m, 3H), 7.09 (d, J=7.8 Hz, 2H), 7.05 (d, J=7.8 Hz, 2H), 4.52 (d, J=9.6 Hz, 1H), 4.28 (d, J=9.6 Hz, 1H), 3.96 (s, 2H), 3.88 (t, J=9.2 Hz, 1H), 3.64 (t, J=5.7 Hz, 2H), 3.56 (t, J=9.0 Hz, 1H), 3.45 (t, J=5.7 Hz, 2H), 3.41 (t, J=9.1 Hz, 1H), 3.23 (s, 6H), 2.93 (s, 3H), 2.60 (t, J=7.6 Hz, 2H), 2.23 (s, 3H), 2.20 (t, J=7.6 Hz, 2H), 1.87 (quin, J=7.6 Hz, 2H), 1.41 (s, 6H). MS (ES+) [M+H]$^+$=650.

6.36. Additional Compounds

Numerous additional compounds of the invention were prepared using procedures analogous to those described above. Those compounds are included in Table 1. The columns entitled "SLGT1" and "SGLT2" provide human SGLT1 $IC_{50}$ and SGLT1 $IC_{50}$ measurements obtained as described below, where: * refers to a value less than 0.01 μM;  refers to a value less than 0.1 μM; * refers to a value less than 1 μM; and—refers to a value not measured or exceeding μM.

TABLE 1

| Chemical Name | SGLT1 | SGLT2 | LCMS [M + H] |
|---|---|---|---|
| (E)-3-(4-(2-methyl-5-((2S,3R,4R,5S,6R)-3,4,5-trihydroxy-6-(methylthio)tetrahydro-2H-pyran-2-yl)benzyl)phenyl)-1-(4-methylpiperazin-1-yl)prop-2-en-1-one | ** | *** | 513 |
| 4-(4-(2-chloro-5-((2S,3R,4R,5S,6R)-3,4,5-trihydroxy-6-(methylthio)tetrahydro-2H-pyran-2-yl)benzyl)phenoxy)butanoic acid | * | *** | 500 [M + NH$_4$] |
| 4-(4-(2-chloro-5-((2S,3R,4R,5S,6R)-3,4,5-trihydroxy-6-(methylthio)tetrahydro-2H-pyran-2-yl)benzyl)phenoxy)-N-(1-hydroxy-2-methylpropan-2-yl)butanamide | *** | *** | 554 |
| 4-(4-(2-methyl-5-((2S,3R,4R,5S,6R)-3,4,5-trihydroxy-6-(methylthio)tetrahydro-2H-pyran-2-yl)benzyl)phenyl)butanoic acid | ** | *** | 464 [M + NH$_4$] |
| (2S,3R,4R,5S,6R)-2-(4-chloro-3-(4-(2-(2-methoxyethoxy)ethoxy)benzyl)phenyl)-6-(methylthio)tetrahydro-2H-pyran-3,4,5-triol | ** | *** | 516 [M + NH$_4$] |
| N-(1-hydroxy-2-methylpropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide | *** | *** | 518 |
| (S,E)-2-amino-5-(4-(2-methyl-5-((2S,3R,4R,5S,6R)-3,4,5-trihydroxy-6-(methylthio)tetrahydro-2H-pyran-2-yl)benzyl)phenyl)pent-4-enoic acid | ** | *** | 474 |
| N-(1,3-dihydroxy-2-(hydroxymethyl)propan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide | *** | *** | 550 |
| N-(1-amino-2-methyl-1-oxopropan-2-yl)-4-(4-(2-methyl-5-((2S,3R,4R,5S,6R)-3,4,5-trihydroxy-6- | *** | *** | 531 |

TABLE 1-continued

| Chemical Name | SGLT1 | SGLT2 | LCMS [M + H] |
|---|---|---|---|
| (methylthio)tetrahydro-2H-pyran-2-yl)benzyl)phenyl)butanamide | | | |
| (2S,3R,4R,5S,6R)-2-(3-(4-ethoxybenzyl)-4-methylphenyl)-6-(methylthio)tetrahydro-2H-pyran-3,4,5-triol | ** | *** | 422 [M + NH$_4$] |
| 2-(4-(2-chloro-5-((2S,3R,4R,5S,6R)-3,4,5-trihydroxy-6-(methylthio)tetrahydro-2H-pyran-2-yl)benzyl)phenoxy)acetic acid | * | ** | 472 [M + NH$_4$] |
| 2-(2-(4-(2-chloro-5-((2S,3R,4R,5S,6R)-3,4,5-trihydroxy-6-(methylthio)tetrahydro-2H-pyran-2-yl)benzyl)phenoxy)acetamido)-2-methylpropanamide | ** | *** | 539 |
| N-(2-methyl-1-(4-methylpiperazin-1-yl)-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide | *** | *** | 614 |
| 2-(4-(2-chloro-5-((2S,3R,4R,5S,6R)-3,4,5-trihydroxy-6-(methylthio)tetrahydro-2H-pyran-2-yl)benzyl)phenoxy)-N-(1,3-dihydroxy-2-(hydroxymethyl)propan-2-yl)acetamide | ** | *** | 558 |
| 2-(4-(2-chloro-5-((2S,3R,4R,5S,6R)-3,4,5-trihydroxy-6-(methylthio)tetrahydro-2H-pyran-2-yl)benzyl)phenoxy)-N-(2-methyl-1-(4-methylpiperazin-1-yl)-1-oxopropan-2-yl)acetamide | ** | *** | 622 |
| (S)-2-amino-6-(4-(4-(2-methyl-5-((2S,3R,4R,5S,6R)-3,4,5-trihydroxy-6-(methylthio)tetrahydro-2H-pyran-2-yl)benzyl)phenyl)butanamido)hexanoic acid | *** | *** | 575 |
| (S)-2-amino-6-(2-(4-(2-chloro-5-((2S,3R,4R,5S,6R)-3,4,5-trihydroxy-6-(methylthio)tetrahydro-2H-pyran-2-yl)benzyl)phenoxy)acetamido)hexanoic acid | ** | *** | 583 |
| (S)-2-amino-6-(4-(2-chloro-5-((2S,3R,4R,5S,6R)-3,4,5-trihydroxy-6-(methylthio)tetrahydro-2H-pyran-2-yl)benzyl)phenoxy)hexanoic acid | ** | *** | 526 |
| (E)-N-(1,3-dihydroxy-2-(hydroxymethyl)propan-2-yl)-5-(4-(2-methyl-5-((2S,3R,4R,5S,6R)-3,4,5-trihydroxy-6-(methylthio)tetrahydro-2H-pyran-2-yl)benzyl)phenyl)pent-4-enamide | *** | *** | 562 |
| (E)-N-(1-amino-2-methyl-1-oxopropan-2-yl)-5-(4-(2-methyl-5-((2S,3R,4R,5S,6R)-3,4,5-trihydroxy-6-(methylthio)tetrahydro-2H-pyran-2-yl)benzyl)phenyl)pent-4-enamide | *** | *** | 543 |
| (E)-N-(2-methyl-1-(4-methylpiperazin-1-yl)-1-oxopropan-2-yl)-5-(4-(2-methyl-5-((2S,3R,4R,5S,6R)-3,4,5-trihydroxy-6-(methylthio)tetrahydro-2H-pyran-2-yl)benzyl)phenyl)pent-4-enamide | *** | *** | 626 |
| N1,N3-bis(1-amino-2-methyl-1-oxopropan-2-yl)-2-((E)-3-(4-(2-methyl-5-((2S,3R,4R,5S,6R)-3,4,5-trihydroxy-6-(methylthio)tetrahydro-2H-pyran-2-yl)benzyl)phenyl)allyl)malonamide | ** | *** | 671 |
| N-(1,3-dihydroxy-2-(hydroxymethyl)propan-2-yl)-5-(4-(2-methyl-5-((2S,3R,4R,5S,6R)-3,4,5-trihydroxy-6-(methylthio)tetrahydro-2H-pyran-2-yl)benzyl)phenyl)pentanamide | *** | *** | 564 |
| N-(1-amino-2-methyl-1-oxopropan-2-yl)-5-(4-(2-methyl-5-((2S,3R,4R,5S,6R)-3,4,5-trihydroxy-6-(methylthio)tetrahydro-2H-pyran-2-yl)benzyl)phenyl)pentanamide | *** | *** | 545 |
| 5-(4-(2-methyl-5-((2S,3R,4R,5S,6R)-3,4,5-trihydroxy-6-(methylthio)tetrahydro-2H-pyran-2-yl)benzyl)phenyl)-1-(4-methylpiperazin-1-yl)pentan-1-one | ** | *** | 543 |
| N-(2-methyl-1-(4-methylpiperazin-1-yl)-1-oxopropan-2-yl)-5-(4-(2-methyl-5-((2S,3R,4R,5S,6R)-3,4,5-trihydroxy-6-(methylthio)tetrahydro-2H-pyran-2-yl)benzyl)phenyl)pentanamide | *** | *** | 628 |
| N-(1-hydroxy-2-methylpropan-2-yl)-5-(4-(2-methyl-5-((2S,3R,4R,5S,6R)-3,4,5-trihydroxy-6-(methylthio)tetrahydro-2H-pyran-2-yl)benzyl)phenyl)pentanamide | *** | *** | 532 |
| (S)-2-amino-4-(4-(2-chloro-5-((2S,3R,4R,5S,6R)-3,4,5-trihydroxy-6-(methylthio)tetrahydro-2H-pyran-2-yl)benzyl)phenoxy)butanoic acid | — | ** | 498 |
| (2S,3R,4R,5S,6R)-2-(3-(4-chlorobenzyl)-4-methylphenyl)-6-(methylthio)tetrahydro-2H-pyran-3,4,5-triol | ** | *** | 412 [M + NH$_4$] |
| 4-(4-(2-methyl-5-((2S,3R,4R,5S,6R)-3,4,5-trihydroxy-6-(methylthio)tetrahydro-2H-pyran-2-yl)benzyl)phenyl)-1-(4-methylpiperazin-1-yl)butan-1-one | ** | *** | 529 |
| (S)-2-amino-6-(5-(4-(2-methyl-5-((2S,3R,4R,5S,6R)-3,4,5-trihydroxy-6-(methylthio)tetrahydro-2H-pyran-2-yl)benzyl)phenyl)pentanamido)hexanoic acid | ** | *** | 589 |

TABLE 1-continued

| Chemical Name | SGLT1 | SGLT2 | LCMS [M + H] |
|---|---|---|---|
| 4-(4-(2-chloro-5-((2S,3R,4R,5S,6R)-3,4,5-trihydroxy-6-(methylthio)tetrahydro-2H-pyran-2-yl)benzyl)phenoxy)-N-(1,3-dihydroxy-2-(hydroxymethyl)propan-2-yl)butanamide | ** | *** | 586 |
| N-(1-amino-2-methyl-1-oxopropan-2-yl)-4-(4-(2-chloro-5-((2S,3R,4R,5S,6R)-3,4,5-trihydroxy-6-(methylthio)tetrahydro-2H-pyran-2-yl)benzyl)phenoxy)butanamide | *** | *** | 567 |
| 2-(4-(2-methyl-5-((2S,3R,4R,5S,6R)-3,4,5-trihydroxy-6-(methylthio)tetrahydro-2H-pyran-2-yl)benzyl)phenoxy)acetic acid | — | ** | 452 [M + NH$_4$] |
| 4-(4-(2-methyl-5-((2S,3R,4R,5S,6R)-3,4,5-trihydroxy-6-(methylthio)tetrahydro-2H-pyran-2-yl)benzyl)phenoxy)butanoic acid | — | ** | 480 [M + NH$_4$] |
| (S,R,S,R,R)-N,N'-((methylazanediyl)bis(propane-3,1-diyl))bis(4-(4-(2-methyl-5-((2S,3R,4R,5S,6R)-3,4,5-trihydroxy-6-(methylthio)tetrahydro-2H-pyran-2-yl)benzyl)phenyl)butanamide) | *** | *** | 1002 |
| 2-methyl-2-(2-(4-(2-methyl-5-((2S,3R,4R,5S,6R)-3,4,5-trihydroxy-6-(methylthio)tetrahydro-2H-pyran-2-yl)benzyl)phenoxy)acetamido)propanamide | ** | *** | 519 |
| 2,2-dimethyl-3-(2-(4-(2-methyl-5-((2S,3R,4R,5S,6R)-3,4,5-trihydroxy-6-(methylthio)tetrahydro-2H-pyran-2-yl)benzyl)phenoxy)acetamido)propanamide | ** | *** | 533 |
| N-(1-amino-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | *** | *** | 547 |
| N-(1-hydroxy-2-methylpropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | *** | *** | 534 |
| 2-(4-(4-(2-chloro-5-((2S,3R,4R,5S,6R)-3,4,5-trihydroxy-6-(methylthio)tetrahydro-2H-pyran-2-yl)benzyl)phenoxy)butanamido)-2-methylpropanoic acid | — | ** | 568 |
| N-(1,3-dihydroxy-2-(hydroxymethyl)propan-2-yl)-2-(4-(2-methyl-5-((2S,3R,4R,5S,6R)-3,4,5-trihydroxy-6-(methylthio)tetrahydro-2H-pyran-2-yl)benzyl)phenoxy)acetamide | ** | *** | 538 |
| N-(1,3-dihydroxy-2-(hydroxymethyl)propan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | *** | *** | 566 |
| 4-(4-(2-methyl-5-((2S,3R,4R,5S,6R)-3,4,5-trihydroxy-6-(methylthio)tetrahydro-2H-pyran-2-yl)benzyl)phenoxy)-1-(4-methylpiperazin-1-yl)butan-1-one | ** | *** | 545 |
| N-(2-methyl-1-(4-methylpiperazin-1-yl)-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | *** | *** | 630 |
| 2-methyl-2-(5-(4-(2-methyl-5-((2S,3R,4R,5S,6R)-3,4,5-trihydroxy-6-(methylthio)tetrahydro-2H-pyran-2-yl)benzyl)phenyl)pentanamido)propanoic acid | — | ** | 546 |
| (S)-2-amino-5-(4-(2-methyl-5-((2S,3R,4R,5S,6R)-3,4,5-trihydroxy-6-(methylthio)tetrahydro-2H-pyran-2-yl)benzyl)phenyl)pentanoic acid | — | ** | 476 |
| N-((S)-1-amino-3-hydroxy-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | ** | *** | 549 |
| methyl 4-(4-(2-chloro-5-((2S,3R,4R,5S,6R)-3,4,5-trihydroxy-6-(methylthio)tetrahydro-2H-pyran-2-yl)benzyl)phenoxy)butanoate | — | — | 514 [M + NH$_4$] |
| N-(1,3-dihydroxy-2-(hydroxymethyl)propan-2-yl)-6-(4-(2-methyl-5-((2S,3R,4R,5S,6R)-3,4,5-trihydroxy-6-(methylthio)tetrahydro-2H-pyran-2-yl)benzyl)phenyl)hexanamide | ** | *** | 578 |
| N-(1-amino-2-methyl-1-oxopropan-2-yl)-6-(4-(2-methyl-5-((2S,3R,4R,5S,6R)-3,4,5-trihydroxy-6-(methylthio)tetrahydro-2H-pyran-2-yl)benzyl)phenyl)hexanamide | ** | *** | 559 |
| N-(3-amino-2,2-dimethyl-3-oxopropyl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | ** | *** | 561 |
| N-((S)-1-amino-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | ** | *** | 533 |

TABLE 1-continued

| Chemical Name | SGLT1 | SGLT2 | LCMS [M + H] |
|---|---|---|---|
| 1-(4-(4-(2-methyl-5-((2S,3R,4R,5S,6R)-3,4,5-trihydroxy-6-(methylthio)tetrahydro-2H-pyran-2-yl)benzyl)phenoxy)butanamido)cyclopentanecarboxamide | *** | *** | 573 |
| N-(1,3-dihydroxypropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | *** | *** | 536 |
| N-((R)-1-amino-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | *** | *** | 533 |
| (S)-2-(4-(4-(2-methyl-5-((2S,3R,4R,5S,6R)-3,4,5-trihydroxy-6-(methylthio)tetrahydro-2H-pyran-2-yl)benzyl)phenoxy)butanamido)succinamide | ** | *** | 576 |
| 2-methyl-2-(3-(5-(4-(2-methyl-5-((2S,3R,4R,5S,6R)-3,4,5-trihydroxy-6-(methylthio)tetrahydro-2H-pyran-2-yl)benzyl)phenyl)pentyl)ureido)propanamide | ** | *** | 574 |
| 1-(1-hydroxy-2-methylpropan-2-yl)-3-(5-(4-(2-methyl-5-((2S,3R,4R,5S,6R)-3,4,5-trihydroxy-6-(methylthio)tetrahydro-2H-pyran-2-yl)benzyl)phenyl)pentyl)urea | ** | *** | 561 |
| N-(1-hydroxy-2-methylpropan-2-yl)-7-(4-(2-methyl-5-((2S,3R,4R,5S,6R)-3,4,5-trihydroxy-6-(methylthio)tetrahydro-2H-pyran-2-yl)benzyl)phenyl)heptanamide | ** | *** | 560 |
| N-(1,3-dihydroxy-2-(hydroxymethyl)propan-2-yl)-7-(4-(2-methyl-5-((2S,3R,4R,5S,6R)-3,4,5-trihydroxy-6-(methylthio)tetrahydro-2H-pyran-2-yl)benzyl)phenyl)heptanamide | ** | *** | 592 |
| 4-(4-(2-chloro-5-((2S,3R,4R,5S,6R)-3,4,5-trihydroxy-6-(methylthio)tetrahydro-2H-pyran-2-yl)benzyl)phenoxy)-N,N-bis(2-hydroxyethyl)butanamide | ** | *** | 570 |
| N-(1-amino-2-methyl-1-oxopropan-2-yl)-7-(4-(2-methyl-5-((2S,3R,4R,5S,6R)-3,4,5-trihydroxy-6-(methylthio)tetrahydro-2H-pyran-2-yl)benzyl)phenyl)heptanamide | ** | *** | 573 |
| N-((S)-1-amino-3-hydroxy-1-oxopropan-2-yl)-4-(4-(2-chloro-5-((2S,3R,4R,5S,6R)-3,4,5-trihydroxy-6-(methylthio)tetrahydro-2H-pyran-2-yl)benzyl)phenoxy)butanamide | ** | *** | 569 |
| N-(3-amino-2,2-dimethyl-3-oxopropyl)-4-(4-(2-chloro-5-((2S,3R,4R,5S,6R)-3,4,5-trihydroxy-6-(methylthio)tetrahydro-2H-pyran-2-yl)benzyl)phenoxy)butanamide | ** | *** | 581 |
| tert-butyl (2-(4-(2-chloro-5-((2S,3R,4R,5S,6R)-3,4,5-trihydroxy-6-(methylthio)tetrahydro-2H-pyran-2-yl)benzyl)phenoxy)ethyl)carbamate | ** | *** | 540 |
| 4-(4-(2-chloro-5-((2S,3R,4R,5S,6R)-3,4,5-trihydroxy-6-(methylthio)tetrahydro-2H-pyran-2-yl)benzyl)phenoxy)-N-ethylbutanamide | ** | *** | 510 |
| (2S,3R,4R,5S,6R)-2-(3-(4-(2-(2-methoxyethoxy)ethoxy)benzyl)-4-methylphenyl)-6-(methylthio)tetrahydro-2H-pyran-3,4,5-triol | *** | *** | 496 [M + NH$_4$] |
| 2-(4-(2-methyl-5-((2S,3R,4R,5S,6R)-3,4,5-trihydroxy-6-(methylthio)tetrahydro-2H-pyran-2-yl)benzyl)phenoxy)acetamide | ** | *** | 434 |
| 4-(4-(2-methyl-5-((2S,3R,4R,5S,6R)-3,4,5-trihydroxy-6-(methylthio)tetrahydro-2H-pyran-2-yl)benzyl)phenoxy)butanamide | ** | *** | 462 |
| 4-(4-(2-chloro-5-((2S,3R,4R,5S,6R)-3,4,5-trihydroxy-6-(methylthio)tetrahydro-2H-pyran-2-yl)benzyl)phenoxy)-N,N-diethylbutanamide | ** | *** | 538 |
| (2S,3R,4R,5S,6R)-2-(3-(4-(2-aminoethoxy)benzyl)-4-chlorophenyl)-6-(methylthio)tetrahydro-2H-pyran-3,4,5-triol | ** | *** | 440 |
| (S,R,S,R,R,S,R,S,R,R)-N,N',N''-(nitrilotris(ethane-2,1-diyl))tris(4-(4-(2-methyl-5-((2S,3R,4R,5S,6R)-3,4,5-trihydroxy-6-(methylthio)tetrahydro-2H-pyran-2-yl)benzyl)phenyl)butanamide) | ** | *** | 1432 |
| (2S,3R,4R,5S,6R)-2-(3-(4-methoxybenzyl)-4-(trifluoromethoxy)phenyl)-6-(methylthio)tetrahydro-2H-pyran-3,4,5-triol | — | — | 478 [M + NH$_4$] |
| (2S,3R,4R,5S,6R)-2-(3-(4-(2,3-dihydroxypropoxy)benzyl)-4-methylphenyl)-6-(methylthio)tetrahydro-2H-pyran-3,4,5-triol | ** | ** | 468 [M + NH$_4$] |
| N-(2-amino-2-oxoethyl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | ** | *** | 519 |

TABLE 1-continued

| Chemical Name | SGLT1 | SGLT2 | LCMS [M + H] |
|---|---|---|---|
| N-(2-hydroxyethyl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | ** | *** | 506 |
| 4-(4-(2-chloro-5-((2S,3R,4R,5S,6R)-3,4,5-trihydroxy-6-(methylthio)tetrahydro-2H-pyran-2-yl)benzyl)phenoxy)-N-(1-hydroxy-2-methylpropan-2-yl)-N-methylbutanamide | ** | *** | 568 |
| 4-(4-(2-chloro-5-((2S,3R,4R,5S,6R)-3,4,5-trihydroxy-6-(methylthio)tetrahydro-2H-pyran-2-yl)benzyl)phenoxy)-N-(2-morpholinocyclohexyl)butanamide | ** | *** | 649 |
| (2S,3R,4R,5S,6R)-2-(3-(4-(5-(benzylamino)pentyl)benzyl)-4-methylphenyl)-6-(methylthio)tetrahydro-2H-pyran-3,4,5-triol | ** | *** | 536 |
| (2S,3R,4R,5S,6R)-2-(3-(4-(5-aminopentyl)benzyl)-4-methylphenyl)-6-(methylthio)tetrahydro-2H-pyran-3,4,5-triol | ** | *** | 446 |
| (2S,3R,4R,5S,6R)-2-(3-(4-(5-(((S)-2,3-dihydroxypropyl)(2,3-dihydroxypropyl)amino)pentyl)benzyl)-4-methylphenyl)-6-(methylthio)tetrahydro-2H-pyran-3,4,5-triol | ** | *** | 594 |
| 1-(1-hydroxy-2-methylpropan-2-yl)-3-(4-(4-(2-methyl-5-((2S,3R,4R,5S,6R)-3,4,5-trihydroxy-6-(methylthio)tetrahydro-2H-pyran-2-yl)benzyl)phenyl)butyl)urea | ** | *** | 547 |
| N-(1-amino-2-methyl-1-oxopropan-2-yl)-4-(4-(2-chloro-5-((2S,3R,4R,5S,6R)-3,4,5-trihydroxy-6-(methylthio)tetrahydro-2H-pyran-2-yl)benzyl)phenoxy)-N-methylbutanamide | *** | *** | 625 [M − H + formate] |
| N-(2-(4-(2-chloro-5-((2S,3R,4R,5S,6R)-3,4,5-trihydroxy-6-(methylthio)tetrahydro-2H-pyran-2-yl)benzyl)phenoxy)ethyl)-3-hydroxy-2,2-dimethylpropanamide | *** | *** | 540 |
| N-ethyl-4-(4-(2-methyl-5-((2S,3R,4R,5S,6R)-3,4,5-trihydroxy-6-(methylthio)tetrahydro-2H-pyran-2-yl)benzyl)phenoxy)butanamide | *** | *** | 490 |
| N-(2-(4-(2-chloro-5-((2S,3R,4R,5S,6R)-3,4,5-trihydroxy-6-(methylthio)tetrahydro-2H-pyran-2-yl)benzyl)phenoxy)ethyl)propionamide | *** | *** | 496 |
| N-(2-(4-(2-chloro-5-((2S,3R,4R,5S,6R)-3,4,5-trihydroxy-6-(methylthio)tetrahydro-2H-pyran-2-yl)benzyl)phenoxy)ethyl)-4-methylpiperazine-1-carboxamide | *** | *** | 566 |
| 4-methyl-N-(4-(4-(2-methyl-5-((2S,3R,4R,5S,6R)-3,4,5-trihydroxy-6-(methylthio)tetrahydro-2H-pyran-2-yl)benzyl)phenyl)butyl)piperazine-1-carboxamide | ** | *** | 558 |
| 1-(1,3-dihydroxy-2-(hydroxymethyl)propan-2-yl)-3-(4-(4-(2-methyl-5-((2S,3R,4R,5S,6R)-3,4,5-trihydroxy-6-(methylthio)tetrahydro-2H-pyran-2-yl)benzyl)phenyl)butyl)urea | *** | *** | 579 |
| 2-methyl-2-(3-(4-(4-(2-methyl-5-((2S,3R,4R,5S,6R)-3,4,5-trihydroxy-6-(methylthio)tetrahydro-2H-pyran-2-yl)benzyl)phenyl)butyl)ureido)propanamide | *** | *** | 560 |
| (2S,3R,4R,5S,6R)-2-(3-(4-(4-aminobutyl)benzyl)-4-methylphenyl)-6-(methylthio)tetrahydro-2H-pyran-3,4,5-triol | *** | *** | 432 |
| (2S,3R,4R,5S,6R)-2-(3-(4-(4-(bis(2,3-dihydroxypropyl)amino)butyl)benzyl)-4-methylphenyl)-6-(methylthio)tetrahydro-2H-pyran-3,4,5-triol | *** | *** | 597 [M + NH$_4$] |
| (2S,3R,4R,5S,6R)-2-(3-(4-(4-((2,3-dihydroxypropyl)amino)butyl)benzyl)-4-methylphenyl)-6-(methylthio)tetrahydro-2H-pyran-3,4,5-triol | ** | *** | 506 |
| 1-(2-(4-(2-chloro-5-((2S,3R,4R,5S,6R)-3,4,5-trihydroxy-6-(methylthio)tetrahydro-2H-pyran-2-yl)benzyl)phenoxy)ethyl)-3-(1-hydroxy-2-methylpropan-2-yl)urea | *** | *** | 555 |
| (2S,3R,4R,5S,6R)-2-(4-chloro-3-(4-(2-(diethylamino)ethoxy)benzyl)phenyl)-6-(methylthio)tetrahydro-2H-pyran-3,4,5-triol | *** | *** | 496 |
| N-(1,3-dihydroxy-2-methylpropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | ** | ** | 550 |
| 1-(4-(4-(2-methyl-5-((2S,3R,4R,5S,6R)-3,4,5-trihydroxy-6-(methylthio)tetrahydro-2H-pyran-2-yl)benzyl)phenyl)butyl)guanidine | *** | *** | 474 |
| (2S,3R,4R,5S,6R)-2-(3-(4-(4-(diethylamino)butyl)benzyl)-4-methylphenyl)-6-(methylthio)tetrahydro-2H-pyran-3,4,5-triol | *** | *** | 488 |
| (3R,4R,5S,6R)-2-(3-(4-(4-((1-hydroxy-2-methylpropan-2-yl)amino)butyl)benzyl)-4-methylphenyl)-6-(methylthio)tetrahydro-2H-pyran-3,4,5-triol | ** | *** | 504 |
| (3R,4R,5S,6R)-2-(3-(4-(4-((1,3-dihydroxy-2-(hydroxymethyl)propan-2-yl)amino)butyl)benzyl)-4-methylphenyl)-6-(methylthio)tetrahydro-2H-pyran-3,4,5-triol | *** | *** | 536 |
| (3R,4R,5S,6R)-2-(3-(4-(4-chlorobutyl)benzyl)-4-methylphenyl)-6-(methylthio)tetrahydro-2H-pyran-3,4,5-triol | *** | *** | 468 [M + NH$_4$] |

TABLE 1-continued

| Chemical Name | SGLT1 | SGLT2 | LCMS [M + H] |
|---|---|---|---|
| 1-((4-(4-(2-methyl-5-((3R,4R,5S,6R)-3,4,5-trihydroxy-6-(methylthio)tetrahydro-2H-pyran-2-yl)benzyl)phenyl)butyl)amino)cyclopentanecarboxamide | ** | *** | 543 |
| 2,2-dimethyl-3-((4-(4-(2-methyl-5-((3R,4R,5S,6R)-3,4,5-trihydroxy-6-(methylthio)tetrahydro-2H-pyran-2-yl)benzyl)phenyl)butyl)amino)propanamide | *** | *** | 531 |
| 3-hydroxy-2,2-dimethyl-N-(4-(4-(2-methyl-5-((2S,3R,4R,5S,6R)-3,4,5-trihydroxy-6-(methylthio)tetrahydro-2H-pyran-2-yl)benzyl)phenyl)butyl)propanamide | *** | *** | 532 |
| N-(4-(4-(2-methyl-5-((2S,3R,4R,5S,6R)-3,4,5-trihydroxy-6-(methylthio)tetrahydro-2H-pyran-2-yl)benzyl)phenyl)butyl)propionamide | *** | *** | 488 |
| 2-(3-(3-(4-(2-chloro-5-((2S,3R,4R,5S,6R)-3,4,5-trihydroxy-6-(methylthio)tetrahydro-2H-pyran-2-yl)benzyl)phenoxy)propyl)ureido)-2-methylpropanamide | *** | *** | 582 |
| N-(3-(4-(2-chloro-5-((2S,3R,4R,5S,6R)-3,4,5-trihydroxy-6-(methylthio)tetrahydro-2H-pyran-2-yl)benzyl)phenoxy)propyl)-3-hydroxy-2,2-dimethylpropanamide | ** | *** | 554 |
| 1-(3-(4-(2-chloro-5-((2S,3R,4R,5S,6R)-3,4,5-trihydroxy-6-(methylthio)tetrahydro-2H-pyran-2-yl)benzyl)phenoxy)propyl)guanidine | *** | *** | 496 |
| 1-(2-(4-(2-chloro-5-((2S,3R,4R,5S,6R)-3,4,5-trihydroxy-6-(methylthio)tetrahydro-2H-pyran-2-yl)benzyl)phenoxy)ethyl)guanidine | *** | *** | 482 |
| 2-methyl-2-(4-(4-(2-methyl-5-((2S,3R,4R,5S,6R)-3,4,5-trihydroxy-6-(methylthio)tetrahydro-2H-pyran-2-yl)benzyl)phenyl)butanamido)propanoic acid | ** | *** | 532 |
| (2S,3R,4R,5S,6R)-2-(4-chloro-3-(4-(2-(piperidin-4-ylamino)ethoxy)benzyl)phenyl)-6-(methylthio)tetrahydro-2H-pyran-3,4,5-triol | ** | *** | 523 |
| N-(2-methyl-1-(4-methylpiperazin-1-yl)-1-oxopropan-2-yl)-4-(4-(2-methyl-5-((2S,3R,4R,5S,6R)-3,4,5-trihydroxy-6-(methylsulfinyl)tetrahydro-2H-pyran-2-yl)benzyl)phenyl)butanamide | ** | *** | 647 [M + NH$_4$] |
| 4-(4-(2-methyl-5-((2S,3R,4R,5S,6R)-3,4,5-trihydroxy-6-(methylthio)tetrahydro-2H-pyran-2-yl)benzyl)phenyl)-N-(1-(4-methylpiperazine-1-carbonyl)cyclopentyl)butanamide | *** | *** | 640 |
| 4-(4-(2-methyl-5-((2S,3R,4R,5S,6R)-3,4,5-trihydroxy-6-(methylthio)tetrahydro-2H-pyran-2-yl)benzyl)phenyl)-N-(4-(4-methylpiperazine-1-carbonyl)tetrahydro-2H-pyran-4-yl)butanamide | *** | *** | 656 |
| 4-(4-(2-methyl-5-((2S,3R,4R,5S,6R)-3,4,5-trihydroxy-6-(methylthio)tetrahydro-2H-pyran-2-yl)benzyl)phenyl)-N-(1-(4-methylpiperazine-1-carbonyl)cyclopropyl)butanamide | *** | *** | 612 |
| N-(2-methyl-1-morpholino-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide | *** | *** | 601 |
| tert-butyl 4-(2-methyl-2-(4-(4-(2-methyl-5-((2S,3R,4R,5S,6R)-3,4,5-trihydroxy-6-(methylthio)tetrahydro-2H-pyran-2-yl)benzyl)phenyl)butanamido)propanoyl)piperazine-1-carboxylate | *** | *** | 700 |
| N-(1-(4-(2-hydroxyethyl)piperazin-1-yl)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide | *** | *** | 644 |
| N-(2-methyl-1-(4-methylpiperidin-1-yl)-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide | *** | *** | 613 |
| tert-butyl (1-(2-methyl-2-(4-(4-(2-methyl-5-((2S,3R,4R,5S,6R)-3,4,5-trihydroxy-6-(methylthio)tetrahydro-2H-pyran-2-yl)benzyl)phenyl)butanamido)propanoyl)piperidin-4-yl)carbamate | *** | *** | 714 |
| tert-butyl 4-(2-methyl-2-(4-(4-(2-methyl-5-((2S,3R,4R,5S,6R)-3,4,5-trihydroxy-6-(methylthio)tetrahydro-2H-pyran-2-yl)benzyl)phenyl)butanamido)propanamido)piperidine-1-carboxylate | *** | *** | 714 |
| N-(2-methyl-1-oxo-1-(piperidin-4-ylamino)propan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide | *** | *** | 614 |

TABLE 1-continued

| Chemical Name | SGLT1 | SGLT2 | LCMS [M + H] |
|---|---|---|---|
| 4-(4-(2-methyl-5-((2S,3R,4R,5S,6R)-3,4,5-trihydroxy-6-(methylthio)tetrahydro-2H-pyran-2-yl)benzyl)phenyl)-N-(2-(4-methylpiperazin-1-yl)-2-oxoethyl)butanamide | *** | *** | 586 |
| 2,2-dimethyl-3-((2-(4-(2-methyl-5-((2S,3R,4R,5S,6R)-3,4,5-trihydroxy-6-(methylthio)tetrahydro-2H-pyran-2-yl)benzyl)phenoxy)ethyl)amino)propanamide | *** | *** | 519 |
| (S,R,S,R,R)-1,1'-(4,4'-(propane-1,3-diyl)bis(piperazine-4,1-diyl))bis(4-(4-(2-methyl-5-((2S,3R,4R,5S,6R)-3,4,5-trihydroxy-6-(methylthio)tetrahydro-2H-pyran-2-yl)benzyl)phenyl)butan-1-one) | *** | *** | 1069 |
| N-(2,2-dimethyl-3-(4-methylpiperazin-1-yl)-3-oxopropyl)-4-(4-(2-methyl-5-((2S,3R,4R,5S,6R)-3,4,5-trihydroxy-6-(methylthio)tetrahydro-2H-pyran-2-yl)benzyl)phenyl)butanamide | *** | *** | 628 |
| 2,2-dimethyl-3-((4-(4-(2-methyl-5-((2S,3R,4R,5S,6R)-3,4,5-trihydroxy-6-(methylthio)tetrahydro-2H-pyran-2-yl)benzyl)phenyl)butyl)amino)-1-(4-methylpiperazin-1-yl)propan-1-one | *** | *** | 614 |
| 2-methyl-2-((4-(4-(2-methyl-5-((2S,3R,4R,5S,6R)-3,4,5-trihydroxy-6-(methylthio)tetrahydro-2H-pyran-2-yl)benzyl)phenyl)butyl)amino)-1-(4-methylpiperazin-1-yl)propan-1-one | *** | *** | 600 |
| (2S,3R,4R,5S,6R)-2-(3-(4-(2-((1-hydroxy-2-methylpropan-2-yl)amino)ethoxy)benzyl)-4-methylphenyl)-6-(methylthio)tetrahydro-2H-pyran-3,4,5-triol | *** | *** | 492 |
| 1-((2-(4-(2-methyl-5-((2S,3R,4R,5S,6R)-3,4,5-trihydroxy-6-(methylthio)tetrahydro-2H-pyran-2-yl)benzyl)phenoxy)ethyl)amino)cyclopentanecarboxamide | ** | *** | 531 |
| N-(1-((2-(dimethylamino)ethyl)(methyl)amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide | *** | *** | 616 |
| N-(2-methyl-1-(methylamino)-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide | *** | *** | 545 |
| 2,2-dimethyl-3-((3-(4-(2-methyl-5-((3R,4R,5S,6R)-3,4,5-trihydroxy-6-(methylthio)tetrahydro-2H-pyran-2-yl)benzyl)phenoxy)propyl)amino)propanamide | *** | *** | 533 |
| (3R,4R,5S,6R)-2-(3-(4-(3-((1-hydroxy-2-methylpropan-2-yl)amino)propoxy)benzyl)-4-methylphenyl)-6-(methylthio)tetrahydro-2H-pyran-3,4,5-triol | *** | *** | 506 |
| N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide | *** | *** | 602 |
| N-(2-methyl-1-oxo-1-(piperazin-1-yl)propan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide | *** | *** | 600 |
| 4-(4-(2-methyl-5-((2S,3R,4R,5S,6R)-3,4,5-trihydroxy-6-(methylthio)tetrahydro-2H-pyran-2-yl)benzyl)phenoxy)-N-(1-(4-methylpiperazine-1-carbonyl)cyclopentyl)butanamide | *** | *** | 656 |
| N-(2-methyl-1-morpholino-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | *** | *** | 617 |
| N-(2-methyl-1-(4-methylpiperidin-1-yl)-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | *** | *** | 629 |
| N-(2,2-dimethyl-3-(4-methylpiperazin-1-yl)-3-oxopropyl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | *** | *** | 661 [M + NH$_4$] |
| N-(1-((2-(dimethylamino)ethyl)(methyl)amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | ** | *** | 632 |
| 1-(2-(4-(2-methyl-5-((3R,4R,5S,6R)-3,4,5-trihydroxy-6-(methylthio)tetrahydro-2H-pyran-2-yl)benzyl)phenoxy)ethyl)guanidine | *** | *** | 462 |
| 1-((3-(4-(2-methyl-5-((3R,4R,5S,6R)-3,4,5-trihydroxy-6-(methylthio)tetrahydro-2H-pyran-2-yl)benzyl)phenoxy)propyl)amino)cyclopentanecarboxamide | *** | *** | 545 |
| (3R,4R,5S,6R)-2-(3-(4-(3-((3-hydroxy-2,2-dimethylpropyl)amino)propoxy)benzyl)-4-methylphenyl)-6-(methylthio)tetrahydro-2H-pyran-3,4,5-triol | *** | *** | 520 |

TABLE 1-continued

| Chemical Name | SGLT1 | SGLT2 | LCMS [M + H] |
|---|---|---|---|
| (3R,4R,5S,6R)-2-(3-(4-(3-((3-(dimethylamino)-2,2-dimethylpropyl)amino)propoxy)benzyl)-4-methylphenyl)-6-(methylthio)tetrahydro-2H-pyran-3,4,5-triol | *** | *** | 547 |
| N-(2-methyl-1-((1-methylpiperidin-4-yl)amino)-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide | *** | *** | 628 |
| 4-methyl-N-(2-(4-(2-methyl-5-((3R,4R,5S,6R)-3,4,5-trihydroxy-6-(methylthio)tetrahydro-2H-pyran-2-yl)benzyl)phenoxy)ethyl)piperazine-1-carboxamide | *** | *** | 546 |
| 1-(1-hydroxy-2-methylpropan-2-yl)-3-(2-(4-(2-methyl-5-((3R,4R,5S,6R)-3,4,5-trihydroxy-6-(methylthio)tetrahydro-2H-pyran-2-yl)benzyl)phenoxy)ethyl)urea | ** | *** | 535 |
| 2,2-dimethyl-3-(3-(2-(4-(2-methyl-5-((3R,4R,5S,6R)-3,4,5-trihydroxy-6-(methylthio)tetrahydro-2H-pyran-2-yl)benzyl)phenoxy)ethyl)ureido)propanamide | *** | *** | 562 |
| 2,2-dimethyl-3-(4-(4-(2-methyl-5-((2S,3R,4R,5S,6R)-3,4,5-trihydroxy-6-(methylthio)tetrahydro-2H-pyran-2-yl)benzyl)phenyl)butanamido)propanoic acid | ** | *** | 546 |
| N-(3-((2-(dimethylamino)ethyl)(methyl)amino)-2,2-dimethyl-3-oxopropyl)-4-(4-(2-methyl-5-((2S,3R,4R,5S,6R)-3,4,5-trihydroxy-6-(methylthio)tetrahydro-2H-pyran-2-yl)benzyl)phenyl)butanamide | — | ** | 630 |
| N-(2,2-dimethyl-3-oxo-3-(piperidin-4-ylamino)propyl)-4-(4-(2-methyl-5-((2S,3R,4R,5S,6R)-3,4,5-trihydroxy-6-(methylthio)tetrahydro-2H-pyran-2-yl)benzyl)phenyl)butanamide | ** | *** | 628 |
| N-(2-amino-2-methylpropyl)-4-(4-(2-methyl-5-((2S,3R,4R,5S,6R)-3,4,5-trihydroxy-6-(methylthio)tetrahydro-2H-pyran-2-yl)benzyl)phenyl)butanamide | *** | *** | 517 |
| N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | *** | *** | 618 |
| N-(2-methyl-1-oxo-1-(piperidin-4-ylamino)propan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | *** | *** | 630 |
| N-(2-methyl-1-((1-methylpiperidin-4-yl)amino)-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide | *** | *** | 644 |
| (3R,4R,5S,6R)-2-(3-(4-(3-((1,3-dihydroxypropan-2-yl)amino)propoxy)benzyl)-4-methylphenyl)-6-(methylthio)tetrahydro-2H-pyran-3,4,5-triol | *** | *** | 508 |
| (3R,4R,5S,6R)-2-(3-(4-(3-((1,3-dihydroxy-2-methylpropan-2-yl)amino)propoxy)benzyl)-4-methylphenyl)-6-(methylthio)tetrahydro-2H-pyran-3,4,5-triol | *** | *** | 539 [M + NH$_4$] |
| 2-methyl-2-(4-(4-(2-methyl-5-((2S,3R,4R,5S,6R)-3,4,5-trihydroxy-6-(methylthio)tetrahydro-2H-pyran-2-yl)benzyl)phenoxy)butanamido)propanoic acid | *** | *** | 548 |
| 4-(4-(2-methyl-5-((2S,3R,4R,5S,6R)-3,4,5-trihydroxy-6-(methylthio)tetrahydro-2H-pyran-2-yl)benzyl)phenyl)butanenitrile | — | ** | 445 [M + NH$_4$] |
| 2-(5-(3-(4-(2-methyl-5-((2S,3R,4R,5S,6R)-3,4,5-trihydroxy-6-(methylthio)tetrahydro-2H-pyran-2-yl)benzyl)phenyl)propyl)-1H-tetrazol-1-yl)-1-(4-methylpiperazin-1-yl)ethanone | *** | *** | 611 |
| 2-(5-(3-(4-(2-methyl-5-((2S,3R,4R,5S,6R)-3,4,5-trihydroxy-6-(methylthio)tetrahydro-2H-pyran-2-yl)benzyl)phenyl)propyl)-2H-tetrazol-2-yl)-1-(4-methylpiperazin-1-yl)ethanone | *** | *** | 611 |
| N,N-dimethyl-2-(4-(2-methyl-5-((2S,3R,4R,5S,6R)-3,4,5-trihydroxy-6-(methylthio)tetrahydro-2H-pyran-2-yl)benzyl)phenoxy)acetamide | ** | *** | 432 |

6.37. In Vitro Human SGLT1 Inhibition Assay

Human sodium/glucose co-transporter type 1 (SGLT1; accession number NP_000334; GI: 4507031) was cloned into pIRESpuro2 vector for mammalian expression (construct: HA-SGLT1-pIRESpuro2).

HEK293 cells were transfected with the human HA-SGLT1-pIRESpuro2 vector and the bulk stable cell line was selected in presence of 0.5 µg/mL of puromycin. Human HA-SGLT1 cells were maintained in DMEM media containing 10% FBS, 1% GPS and 0.5 µg/mL of puromycin.

The HEK293 cells expressing the human HA-SGLT1 were seeded in 384 well plates (30,000 cells/well) in DMEM media containing 10% FBS, 1% GPS and 0.5 µg/mL of puromycin, then incubated overnight at 37 C, 5% $CO_2$. Cells were then washed with uptake buffer (140 mM NaCl, 2 mM KCl, 1 mM $CaCl_2$, 1 mM $MgCl_2$, 10 mM HEPES, 5 mM Tris, 1 mg/mL bovine serum albumin (BSA), pH 7.3). Twenty microliters of uptake buffer with or without testing compounds were added to the cells. Then, 20 microliters of uptake buffer containing $^{14}$C-AMG (100 nCi) were also added to cells. The cell plates were incubated at 37° C., 5% $CO_2$ for 1-2 hours. After washing the cells with uptake buffer, scintillation fluid was added (40 microliters/well) and $^{14}$C-AMG uptake was measured by counting radioactivity using a scintillation coulter (TopCoulter NXT; Packard Instruments).

6.38. In Vitro Human SGLT2 Inhibition Assay

Human sodium/glucose co-transporter type 2 (SGLT2; accession number P31639; GI:400337) was cloned into pIRESpuro2 vector for mammalian expression (construct: HA-SGLT2-pIRESpuro2).

HEK293 cells were transfected with the human HA-SGLT2-pIRESpuro2 vector and the bulk stable cell line was selected in presence of 0.5 µg/mL of puromycin. Human HA-SGLT2 cells were maintained in DMEM media containing 10% FBS, 1% GPS and 0.5 µg/mL of puromycin.

The HEK293 cells expressing the human HA-SGLT2 were seeded in 384 well plates (30,000 cells/well) in DMEM media containing 10% FBS, 1% GPS and 0.5 µg/mL of puromycin, then incubated overnight at 37 C, 5% $CO_2$. Cells were then washed with uptake buffer (140 mM NaCl, 2 mM KCl, 1 mM $CaCl_2$, 1 mM $MgCl_2$, 10 mM HEPES, 5 mM Tris, 1 mg/mL bovine serum albumin (BSA), pH 7.3). Twenty microliters of uptake buffer with or without testing compounds were added to the cells. Then, 20 microliters of uptake buffer containing $^{14}$C-AMG (100 nCi) were added to the cells. The cell plates were incubated at 37° C., 5% $CO_2$ for 1-2 hours. After washing the cells with uptake buffer, scintillation fluid was added (40 microliters/well) and $^{14}$C-AMG uptake was measured by counting radioactivity using a scintillation coulter (TopCoulter NXT; Packard Instruments).

6.39. Tolerability and Pharmacology

The in vivo tolerability and pharmacology of compounds of the invention was determined using 18 week-old male C57/Blk6 mice. The mice were switched to 10% low fat diet (LFD, D12450Bi) from regular chow and individually housed for one week before study. The mice were then randomized into the following groups by their body weight:

| Compound | Chemical Name or Composition |
|---|---|
| A | N-(2-methyl-1-((1-methylpiperidin-4-yl)amino)-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide |
| B | N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide |
| C | (2S,3R,4R,5S,6R)-2-(3-(4-(3-((1-hydroxy-2-methylpropan-2-yl)amino)propoxy)benzyl)-4-methylphenyl)-6-(methylthio)tetrahydro-2H-pyran-3,4,5-triol |
| D | N-(2-methyl-1-((1-methylpiperidin-4-yl)amino)-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenoxy)butanamide |
| E | N-(2-methyl-1-(4-methylpiperazin-1-yl)-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide |
| Vehicle | 0.1% Tween 80 in water |

Mice received either vehicle or compound by oral gavage at 1 mg/kg and in a volume of 10 mL/kg once daily for 4 days. Body weight, food consumption and diarrhea were monitored daily. At 6 hours after the last dose, blood was collected from the mice by retro-orbital bleeding for baseline glucose. The mice were then given a glucose-containing meal, prepared by suspending 50 g of low fat diet (LFD) powder (10% kcal as fat; diet D12450B, Research Diets, New Brunswick, N.J.) in 60 mL of water. Conscious mice received, by oral gavage, 20 mL/kg of this suspension, along with 5 mL/kg of 50% dextrose, which provided them with 9.2 g/kg glucose, 2.5 g/kg protein and 0.6 g/kg fat.

Figures 1A, 1B:
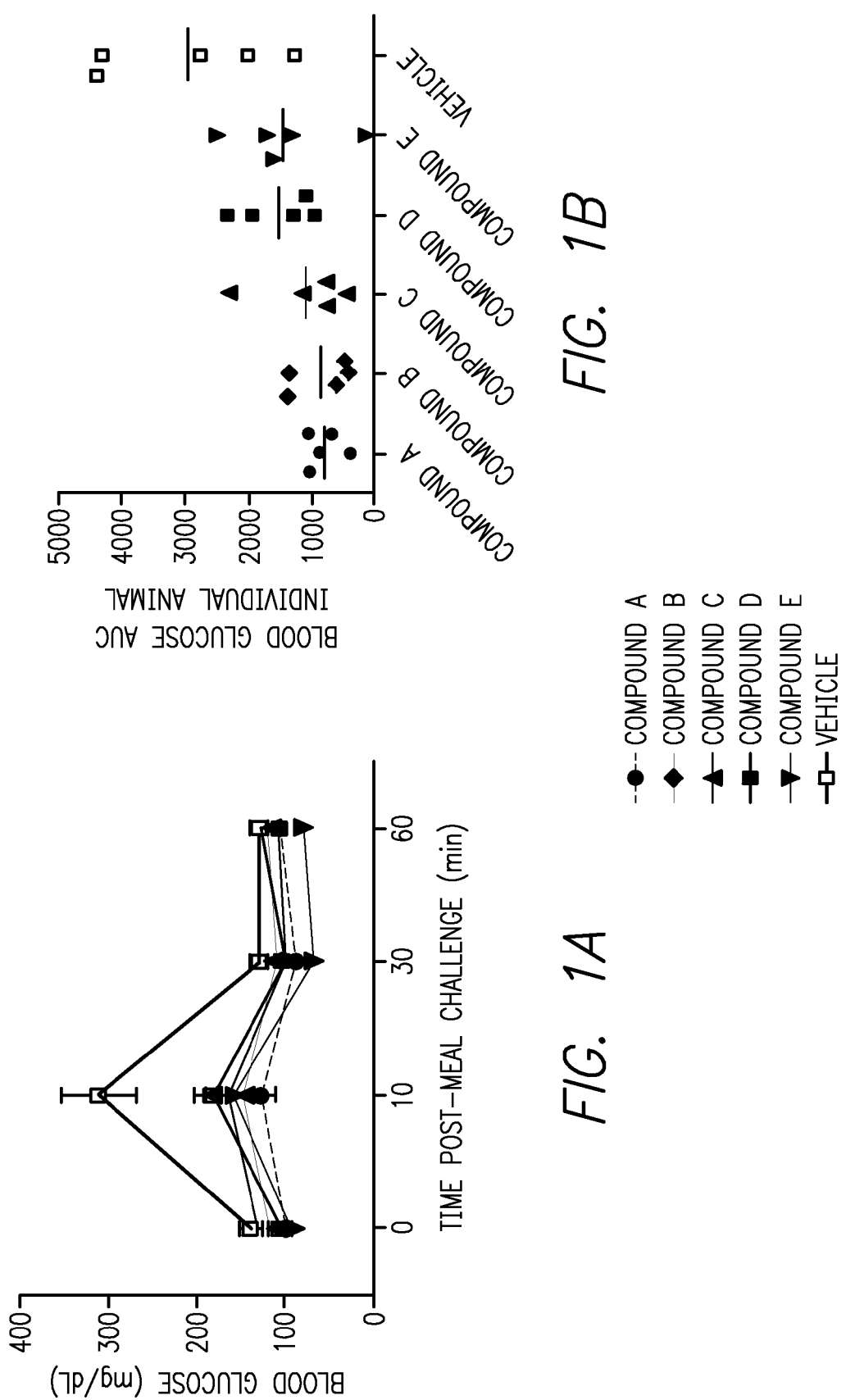
FIG. 1A shows the effect of five compounds of the invention, administered at a dose of 1.0 mg/kg ("mpk") once daily for four days, on the blood glucose levels of 18 week-old male C57/Blk6 mice after being fed a glucose-containing meal six hours after the final dose. Areas under the curves for each animal in the experiment are shown in FIG. 1B.

Blood was collected at 10, 30, and 60 minutes after the meal to estimate the postprandial glucose excursion. Blood glucose was measured using an Accu-Chek Aviva glucometer (Roche Diagnostics, Indianapolis, Ind.) according the protocol recommended by the manufacturer. FIG. 1A shows the effect of 1.0 mg/kg ("mpk") of compounds A-E on the blood glucose levels of the mice, compared to vehicle, as a function of time after their post meal challenge. Areas under the curves for each animal in the experiment are shown in FIG. 1B.

Figure 2:
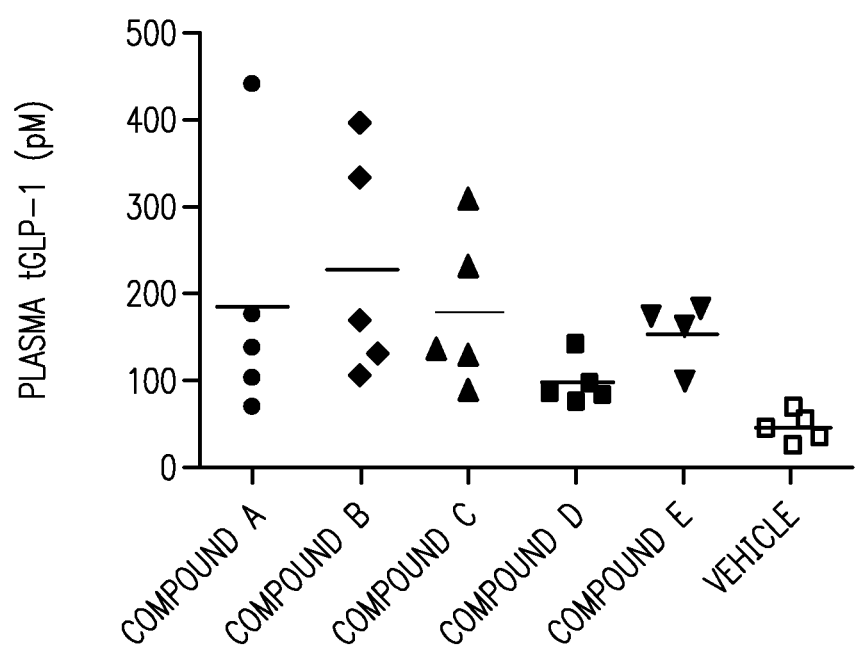
FIG. 2 shows the compounds' effect on plasma tGLP-1, compared to vehicle, for each mouse.

At 60 minutes after meal challenge, additional blood was collected for total glucagon-like peptide-1 (tGLP-1) analysis. For this measurement, plasma was prepared by centrifuging blood samples at 1000 rpm for 10 minutes at 4° C.

tGPL-1 was analyzed by ELISA (Glucagon-Like Peptide-1 Total ELISA Kit, catalog #EZGLP1T-36K, Millipore, St. Charles, Mo.) according to the protocol recommended by Millipore. FIG. 2 shows the compounds' effect on plasma tGLP-1, compared to vehicle, for each mouse.

Figure 3:
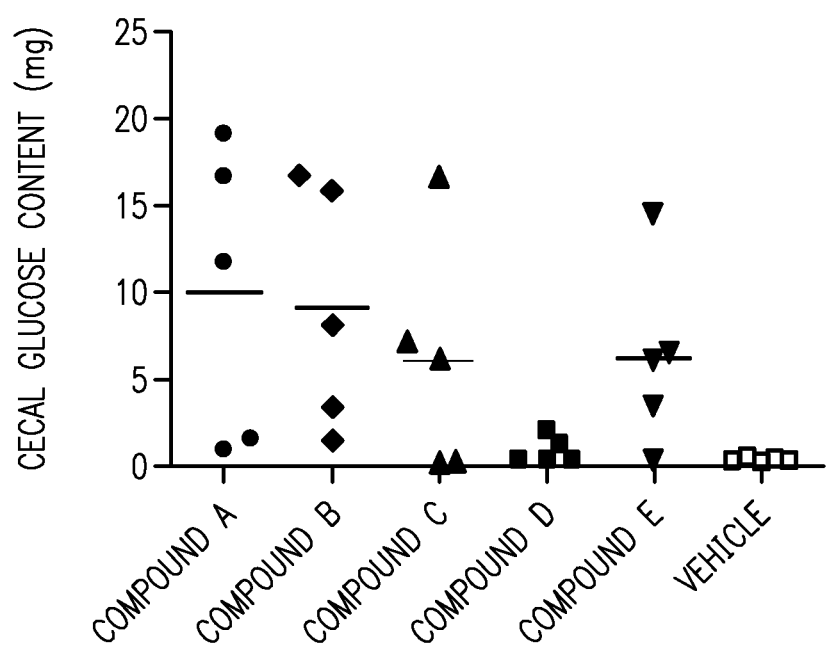
FIG. 3 shows the compounds' effect on the mice's cecal glucose.

Cecal contents were collected for glucose analysis immediately after collection of the final blood sample. This analysis was performed by adding five mL of cold MilliQ water to 1 gram of cecal contents. The mixture was then homogenized for 1 minute using a Mini Beadbeater (Biospec Products, Bartlesville, O K). The homogenate was centrifuged at 4° C. for 25 minutes at the speed of 3750 rpm. The supernatant was collected. Cecal glucose was analyzed by Cobas Integra 400 Autoanalyzer (Roche Diagnostics). FIG. 3 shows the results of this analysis for each mouse.

6.40. Effects on KKAy Diabetic Mice

Twelve week-old male KKay mice were purchased from The Jackson Laboratory (Bar Harbor, Me.). They were switched to 45% high fat diet (HFD; diet D12451i, Research Diets) and housed individually for one week before study. The mice were randomized into the following groups by their HbA1c levels and body weights:

| Compound | Dose | Number of mice (N) |
| --- | --- | --- |
| Vehicle (0.1% Tween 80 in water) | — | 9 |
| Compound C | 1.5 mg/kg | 10 |
| Compound C | 4.5 mg/kg | 10 | where Compound C is (2S,3R,4R,5S,6R)-2-(3-(4-(3-((1-hydroxy-2-methylpropan-2-yl)amino)propoxy)benzyl)-4-methylphenyl)-6-(methylthio)tetrahydro-2H-pyran-3,4,5-triol.

Figure 4:
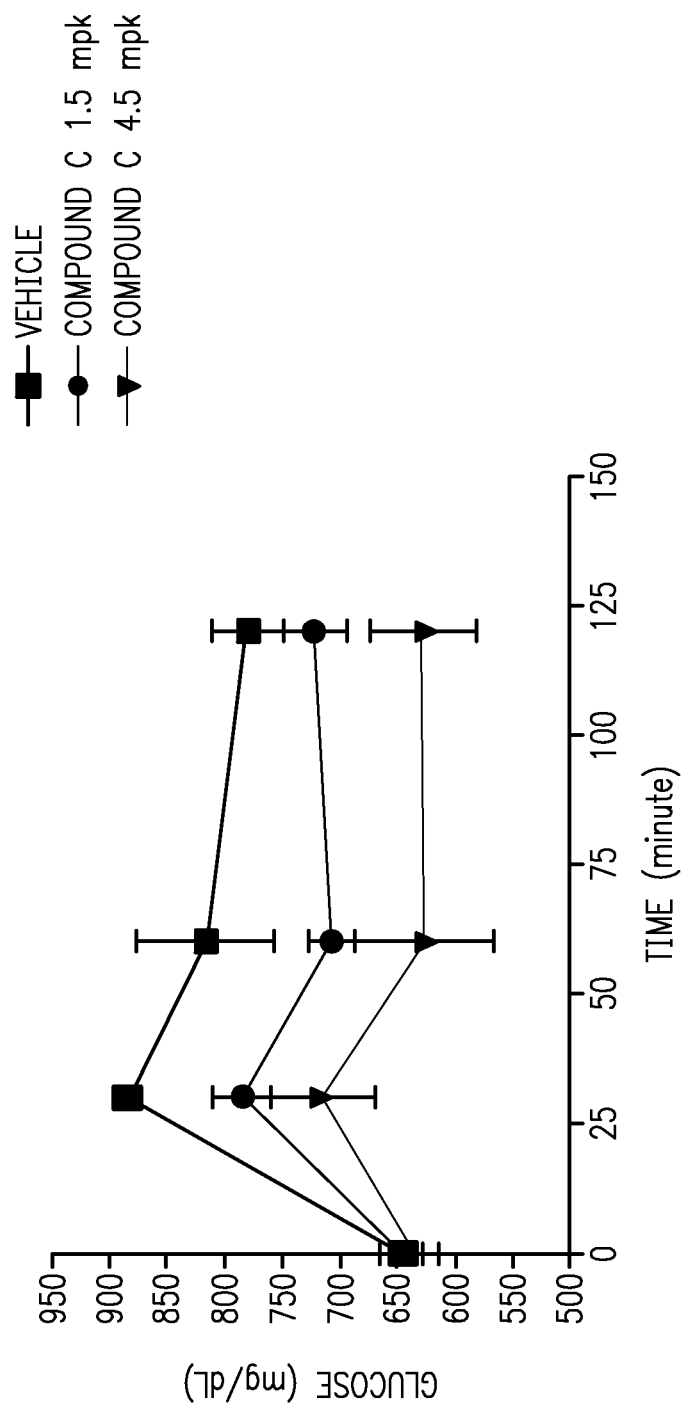
FIG. 4 shows the dose-dependent decrease in glucose excursion upon receiving a glucose challenge administered 15 hours after dosing a compound of the invention. The compound had been administered daily for 22 days to 12 week-old male KKay mice maintained on a 45% high fat diet.

Mice received either vehicle or Compound C once daily at 5:00 μm for 36 days. Body weight and food consumption were monitored daily. On day 22, blood was collected before glucose challenge for baseline glucose. Mice were then given a bolus dose of glucose (2 g/kg, 10 mL/kg). Blood was collected at 30, 60 and 120 minutes after glucose challenge to estimate the glucose excursion. Blood glucose was analyzed by Cobas Integra 400 Autoanalyzer (Roche Diagnostics). FIG. 4 shows the dose-dependent decrease in glucose excursion at 15 hours after dosing Compound C, where time t=0 is the time the glucose bolus was administered.

On day 26 after dosing, blood was collected for HbA1c. HbA1c was measured using a meter manufactured by Bayer according to the protocol recommended by Bayer. As shown in FIG. 5A, mice treated with Compound C exhibited a significant, dose-dependent reduction in HbA1c. FIG. 5B shows the change in the mice's HbA1c between days 0 and 27.

On day 29, the mice again received a glucose bolus (2 g/kg, 10 mL/kg). Blood was collected at 60 minutes after glucose challenge and analyzed for tGLP-1. Plasma was prepared by centrifuging blood samples at 1000 rpm for 10 minutes at 4° C. tGPL-1 was analyzed by ELISA (Glucagon-Like Peptide-1 Total ELISA Kit, catalog #EZGLP1T-36K, Millipore, St. Charles, Mo.) according to the protocol recommended by Millipore. As shown in FIG. 6, a significant increase in postprandial tGLP-1 was observed in the 4.5 mpk group (p<0.5).

All publications (e.g., patents and patent applications) cited above are incorporated herein by reference in their entireties.

What is claimed is:

1. A compound, which is N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide:

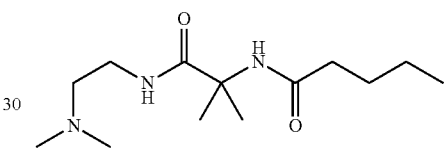

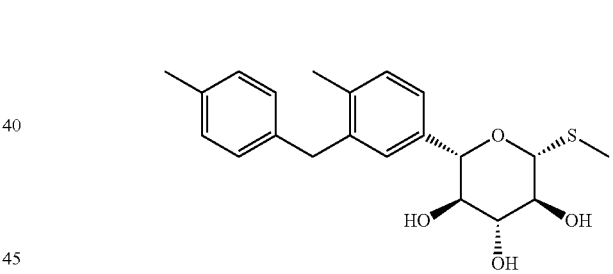

or a pharmaceutically acceptable salt thereof.

2. A pharmaceutical composition comprising the compound of claim 1 and a pharmaceutically acceptable excipient or diluent.

3. A solid oral dosage form comprising the pharmaceutical composition of claim 2.

4. The solid oral dosage form of claim 3, which is a tablet.

5. The solid oral dosage form of claim 3, which is a capsule.

6. A method of treating or managing diabetes, which comprises administering to a patient in need thereof a therapeutically effective amount of N-(1-((2-(dimethylamino)ethyl)amino)-2-methyl-1-oxopropan-2-yl)-4-(4-(2-methyl-5-((2S,3R,4R,5S,6R)-3,4,5-trihydroxy-6-(methylthio)tetrahydro-2H-pyran-2-yl)benzyl)phenyl)butanamide:

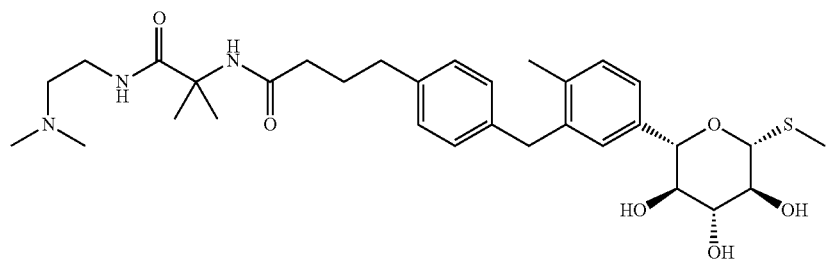
or a pharmaceutically acceptable salt thereof.
7. The method of claim 6, wherein the diabetes is type 1 diabetes.
8. The method of claim 6, wherein the diabetes is type 2 diabetes.
* * * * *